US009169442B2

(12) United States Patent
Huber et al.

(10) Patent No.: US 9,169,442 B2
(45) Date of Patent: *Oct. 27, 2015

(54) SYSTEMS AND PROCESSES FOR CATALYTIC PYROLYSIS OF BIOMASS AND HYDROCARBONACEOUS MATERIALS FOR PRODUCTION OF AROMATICS WITH OPTIONAL OLEFIN RECYCLE, AND CATALYSTS HAVING SELECTED PARTICLE SIZE FOR CATALYTIC PYROLYSIS

(75) Inventors: George W. Huber, Belchertown, MA (US); Anne Mae Gaffney, West Chester, PA (US); Jungho Jae, Amherst, MA (US); Yu-Ting Cheng, Amherst, MA (US)

(73) Assignee: University of Massachusetts, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/394,559

(22) PCT Filed: Sep. 9, 2010

(86) PCT No.: PCT/US2010/002472
§ 371 (c)(1),
(2), (4) Date: Apr. 30, 2012

(87) PCT Pub. No.: WO2011/031320
PCT Pub. Date: Mar. 17, 2011

(65) Prior Publication Data
US 2012/0203042 A1 Aug. 9, 2012

Related U.S. Application Data

(60) Provisional application No. 61/241,018, filed on Sep. 9, 2009.

(51) Int. Cl.
*C10G 1/00* (2006.01)
*C10G 1/10* (2006.01)
(Continued)

(52) U.S. Cl.
CPC . *C10G 1/10* (2013.01); *C10B 49/22* (2013.01); *C10B 53/02* (2013.01); *C10B 57/06* (2013.01);
(Continued)

(58) Field of Classification Search
USPC .......................................................... 585/315
See application file for complete search history.

(56) References Cited

U.S. PATENT DOCUMENTS

| | | | |
|---|---|---|---|
| 3,931,349 A | 1/1976 | Kuo | |
| 3,936,353 A | 2/1976 | Chen | |

(Continued)

FOREIGN PATENT DOCUMENTS

| | | |
|---|---|---|
| EP | 1 852 491 | 11/2007 |
| EP | 1 892 280 A1 | 2/2008 |

(Continued)

OTHER PUBLICATIONS

Lee, K-H. et al. (2003). J. Ind. Eng. Chem., 9(5), 584-589.*

(Continued)

*Primary Examiner* — In Suk Bullock
*Assistant Examiner* — Philip Louie
(74) *Attorney, Agent, or Firm* — Renner, Otto, Boisselle & Sklar, LLP

(57) ABSTRACT

This invention relates to compositions and methods for fluid hydrocarbon product, and more specifically, to compositions and methods for fluid hydrocarbon product via catalytic pyrolysis. Some embodiments relate to methods for the production of specific aromatic products (e.g., benzene, toluene, naphthalene, xylene, etc.) via catalytic pyrolysis. Some such methods may involve the use of a composition comprising a mixture of a solid hydrocarbonaceous material and a heterogeneous pyrolytic catalyst component. In some embodiments, an olefin compound may be co-fed to the reactor and/or separated from a product stream and recycled to the reactor to improve yield and/or selectivity of certain products. The methods described herein may also involve the use of specialized catalysts. For example, in some cases, zeolite catalysts may be used. In some instances, the catalysts are characterized by particle sizes in certain identified ranges that can lead to improve yield and/or selectivity of certain products.

73 Claims, 34 Drawing Sheets

(51) Int. Cl.

| | | |
|---|---|---|
| *C10B 49/22* | (2006.01) | |
| *C10B 53/02* | (2006.01) | |
| *C10B 57/06* | (2006.01) | |
| *C10G 3/00* | (2006.01) | |
| *C10G 11/18* | (2006.01) | |
| *C10G 1/02* | (2006.01) | |
| *B01J 29/40* | (2006.01) | |
| *B01J 29/44* | (2006.01) | |
| *B01J 29/46* | (2006.01) | |
| *B01J 29/48* | (2006.01) | |
| *B01J 29/87* | (2006.01) | |

(52) U.S. Cl.
CPC ........ *C10G 1/002* (2013.01); *C10G 1/02* (2013.01); *C10G 3/00* (2013.01); *C10G 11/18* (2013.01); *B01J 29/40* (2013.01); *B01J 29/405* (2013.01); *B01J 29/44* (2013.01); *B01J 29/46* (2013.01); *B01J 29/48* (2013.01); *B01J 29/87* (2013.01); *C10G 2300/1003* (2013.01); *C10G 2300/1014* (2013.01); *C10G 2300/4018* (2013.01); *C10G 2300/4081* (2013.01); *C10G 2300/70* (2013.01); *C10G 2400/20* (2013.01); *C10G 2400/30* (2013.01); *Y02E 50/14* (2013.01)

(56) References Cited

U.S. PATENT DOCUMENTS

| | | | |
|---|---|---|---|
| 3,998,898 A | 12/1976 | Chang et al. | |
| 4,035,430 A | 7/1977 | Dwyer et al. | |
| 4,058,576 A | 11/1977 | Chang et al. | |
| 4,300,009 A | 11/1981 | Haag et al. | |
| 4,483,764 A | 11/1984 | Hensley et al. | |
| 4,503,278 A | 3/1985 | Chen et al. | |
| 4,549,031 A | 10/1985 | Chen et al. | |
| 4,687,654 A | 8/1987 | Taramasso et al. | |
| 4,933,283 A | 6/1990 | Chen et al. | |
| 5,502,259 A | 3/1996 | Zakoshansky et al. | |
| 5,504,259 A | 4/1996 | Diebold et al. | |
| 6,359,186 B1 | 3/2002 | Hotier et al. | |
| 6,369,287 B1 | 4/2002 | Magne-Drisch | |
| 6,429,346 B2 | 8/2002 | Hotier et al. | |
| 6,495,723 B1 | 12/2002 | DeVera et al. | |
| 6,814,940 B1* | 11/2004 | Hiltunen et al. .............. | 422/141 |
| 6,822,126 B2* | 11/2004 | Miller ........................... | 585/241 |
| 2006/0173225 A1* | 8/2006 | Das et al. ..................... | 585/467 |
| 2008/0076945 A1 | 3/2008 | Marker et al. | |
| 2008/0228021 A1 | 9/2008 | Joensen et al. | |
| 2009/0090046 A1 | 4/2009 | O'Connor et al. | |
| 2009/0165378 A1* | 7/2009 | Agblevor ..................... | 48/127.7 |
| 2009/0227823 A1 | 9/2009 | Huber et al. | |
| 2014/0323784 A1 | 10/2014 | Joshi et al. | |

FOREIGN PATENT DOCUMENTS

| | | | | |
|---|---|---|---|---|
| JP | | 7256228 | | 10/1995 |
| JP | | 200095894 | | 4/2000 |
| JP | | 2000095894 | | 4/2000 |
| JP | | 2001316517 | | 11/2001 |
| JP | | 2001316517 A | * | 11/2001 |
| JP | | 2002088375 | | 3/2002 |
| JP | | 2004-339360 | | 12/2004 |
| JP | | 2004339360 | | 12/2004 |
| JP | | 2007-153925 | | 6/2007 |
| JP | | 2007153925 | | 6/2007 |
| KR | 10-2006-0102778 | | | 9/2006 |
| WO | | 9410107 | | 5/1994 |
| WO | WO 2007/064014 | | | 6/2007 |
| WO | WO 2007/128799 | | | 11/2007 |
| WO | | 2008009643 | | 1/2008 |
| WO | WO 2008/006904 A1 | | | 1/2008 |
| WO | WO 2008/009644 | | | 1/2008 |
| WO | | 2008020047 | | 2/2008 |
| WO | WO 2008/020047 A2 | | | 2/2008 |
| WO | | 2008101949 | | 8/2008 |

OTHER PUBLICATIONS

Demirbas et al., Biomass pyrolysis for liquid fuels and chemicals: A review, Journal of Scientific & Industrial Research, vol. 66, Oct. 2007. pp. 797-804.*
International Search Report, Application No. PCT/US2010/002472, mailed May 26, 2011.
Supplemental European Search Report, Application No. 09718012.9, dated Jul. 28, 2011.
Park et al.; "Conversion of the Pyrolytic Vapor of Radiata Pine over Zeolites"; J. Ind. Eng. Chem., vol. 13, No. 2, (2007) 182-189.
Olazar et al.; "Pyrolysis of Sawdust in Conical Spouted-Bed Reactor with a HZSm-5 Catalyst"; AIChE Journal, May 2000, vol. 46, No. 5, pp. 1025-1033.
Nokkosmaki et al.; "Catalytic conversion of biomass pyrolysis vapours with zinc oxide"; Journal of Analytical and Applied Pyrolysis, 55 (2000) 119-131.
Gobin et al.; "Polymer degradation to fuels over microporous catalysts as a novel tertiary plastic recycling method"; Polymer Degradation and Stability 83 (2004) 267-279.
U.S. Appl. No. 12/397,303, filed Mar. 3, 2009.
Lappas; Catalytic Biomass Pyrolysis for Producing Promising Liquid Bio-Fuels (Biocat); Bio-Energy Enlarged Perspectives; Budapest; Oct. 16-17, 2003.
Sharma et al.; "Upgrading of pyrolytic lignin fraction of fast pyrolysis oil to hydrocarbon fuels over HZSM-5 in a dual reactor system"; Fuel Processing Technology, 25 (1993) 201-218.
Fabbri et al.; "Pyrolysis of cellulose catalysed by nanopowder metal oxides: production and characterization of chiral hydroxylactone and its role as building block"; Green Chem., 2007, 9, 1374-1379.
Notice of Allowance, U.S. Appl. No. 12/397,303, mailed Jul. 3, 2012.
Supplemental Amendment, U.S. Appl. No. 12/397,303, dated May 8, 2012.
Response to Office Action, U.S. Appl. No. 12/397,303, dated Apr. 16, 2012.
US Office Action, U.S. Appl. No. 12/397,303, mailed Dec. 15, 2011.
International Search Report and Written Opinion from PCT/US2009/001382, mailed Oct. 26, 2009.
Huber, "Career: Selective Thermal Processing of Biomass-derived Oxygenates by Catalytic Fast Pyrolysis", NSF Grant Proposal, Submitted to NSF in Aug. 2007, Funded with a start date of Feb. 1, 2008.
Huber, et al, "Acquisition of Instrumentation for a Biofuels Research Laboratory", Proposal to the NSF, NSF 07-510, Funding started on Sep. 1, 2007.
Huber, G., "Money Doesn't Grow on Trees, But Gasoline Might", Press Release 08-056, NSF Web Site, Apr. 7, 2008, www.nsf.gov/news/news_summ.jsp?cntn_id=111392.
Adam, J. et al., "In situ catalytic upgrading of biomass derived fast pyrolysis vapours in a fixed bed reactor using mesoporous materials," Microporous and Mesoporous Materials, 2006, 96, 93-101.
Aho, A., "Catalytic pyrolysis of biomass in a fluidized bed reactor: influence of the acidity of H-beta zeolite," IChemB, 2007, 85 (B5), 473-480.
Aho, A. et al., "Catalytic pyrolysis of woody biomass in a fluidized bed reactor: Influence of the zeolite structure," Fuel, Published online Mar. 14, 2008, 1-9.
Alferov, V. et al., "Catalytic activity of natural and synthetic zeolites . . . ," 2006, 6, 42-46.
Antal, Jr. M., "Effects of Reactor Severity on the Gas-Phase Pyrolysis of Celulose and Kraft Lignin-Derived Volatile Matter," Ind. Eng. Chem. Prod. Res. Dev. 1983, 22, 366-375.
Antal, Jr., M. et al., "Cellulose Pyrolysis Kinetics: The Current State of Knowledge," Ind. Eng. Chem. Res. 1995, 34, 703-717.
Antonakou, E. et al., "Evaluation of various types of Al-MCM-41 materials in catalysts in biomass pyrolysis for the production of bio-fuels and chemicals," Fuel, 2006, 85, 2202-2212.
Ates, F. et al., "Catalytic pyrolysis of perennial shrub, Euphorbia rigida in the water vapour atmosphere," J. Anal. Appl. Pyrolysis, 2005, 73, 299-304.

(56) References Cited

OTHER PUBLICATIONS

Atutxa, A. et al., "Kinetic Description of the Catalytic Pyrolysis of Biomass in a Conical Spouted Bed Reactor," Energy & Fuels, 2005, 19, 765-774.
Bagri, R. et al., "Catalytic pyrolysis of polyethylene," Journal of Analytical and Applied Pyrolysis, 2002, 63, 29-41.
Balat, M., "Mechanisms of Thermochemical Biomass Conversion Processes. Part 1: Reactions of Pyrolysis," Energy Sources, 2008, 30 (Part A), 620-635.
Balat, M., "Mechanisms of Thermochemical Biomass Conversion Processes. Part 2: Reactions of Gasification," Energy Sources, 2008, 30 (Part A), 636-648.
Bauer, F., "Mechanistic and tracer-kinetic studies on methanol conversion on HZSM-5 catalysts," ISOOCLC, 1990, 3-190.
Bauer, F. et al., "TG-FTIR and isotopic studies on coke formation during the MTG process," Microporous and Mesoporous Materials, 1999, 29, 109-115.
Bertarione, S. et al., "Furfuryl Alcohol Polymerization in H-Y Confined Spaces: Reaction Mechanism and Structure of Carbocationic Intermediates," J. Phys. Chem. B, 2008, 112, 2580-2589.
Bilba, K. et al., "Fourier transform infrared spectroscopic study of thermal degradation of sugar cane bagasse," Journal of Analytical and Applied Pyrolysis, 1996, 38, 61-73.
Blazso, M., "In situ modification of pyrolysis products of macromolecules in an analytical pyrolyser," J. Anal. Appl. Pyrolysis, 2005, 74, 344-352.
Blommel, P. et al., "Production of Conventional Liquid Fuels from Sugars," http://www.virent.com/BioForming/Virent_Technology_Whitepaper.pdf., Published online Aug. 25, 2008.
Boateng, A., "Characterization and Thermal Conversion of Charcoal Derived from Fluidized-Bed Fast Pyrolysis Oil Production of Switchgrass," Ind. Eng. Chem. Res., 2007, 46, 8857-8862.
Boateng, A. et al., "Bench-Scale Fluidized-Bed Pyrolysis of Switchgrass for Bio-Oil Production," Ind. Eng. Chem. Res., 2007, 46, 1891-1897.
Boon, J. et al., "Structural Studies on Cellulose Pyrolysis and Cellulose Chars by PYMS, PYGCMS, FTIR, NMR and by Wed Chemical Techniques," Biomass and Bioenergy, 1994, 7 (1-6), 25-32.
Bridgwater A., "Fast pyrolysis of biomass: technical requirements for commercialization," Proceedings of an Expert Meeting, Strasbourg, France, 2002, vol. 2003, pp. 33-40.
Bridgwater, A., "Production of high grade fuels and chemicals from catalytic pyrolysis of biomass," Catalysis Today, 1996, 29, 285-295.
Bridgwater, A. et al., "Fast pyrolysis processes for biomass," Renewable and Sustainable Energy Reviews, 2000, 4, 1-73.
Bridgwater, A. et al., "Production Costs of Liquid Fuels From Biomass," International Journal of Energy Research, 1994,18, 79-95.
Cao, Q., "Influence of co-pyrolysis and catalysis of biomass with waste tire on pyrolytic oil properties," Journal of Chemical Industry and Engineering (China), 2007, 50 (5), 1283-1289.
Carlson, T. et al., "Aromatic Production from Catalytic Fast Pyrolysis of Biomass-Derived Feedstocks," Top Catal, 2009, 52, 241-252.
Carlson, T. et al., "Green Gasoline by Catalytic Fast Pyrolysis of Solid Biomass Derived Compounds," ChemSusChem, 2008, 1, 397-400.
Carlson, T. et al., "Mechanistic Insights from Isotopic Studies of Glucose Conversion to Aromatics Over ZSM-5," ChemCatChem, 2009, 1, 107-110.
Casu, B. et al., "Hydrogen-Deuterium Exchange of Glucose and Polyglucoses in Dimethyl Sulphoxide Solution," Solution Properties of Natural Polymers, Special Publication—Chemical Society, 1968, 217-226.
Chen, G. et al., "The Mathematical Modeling of Biomass Pyrolysis in a Fixed Bed and Experimental Verification," Section of Thermal Power Engineering, Department of Medical Engineering and Marine Technology, Delft University of Technology, 2001, 2, 1158-1170.
Chen, N.Y. et al., "Fluidized-Bed Upgrading of Wood Pyrolysis Liquids and Related Compounds," ACS Symposium Series, 1988, 376, 277-288.
Chen, N.Y. et al., "Liquid Fuel from Carbohydrates," Chemtech, 1986, 508-511.
Copeland, D., http://www.boston.com/business/articles/2009/07/13/the_greening_of_gasoline/. Published Jul. 13, 2009.
Corma, A. et. al., "Processing biomass-derived oxygenates in the oil refinery : Catalytic cracking (FCC) reaction pathways and role of catalyst," J. Catalysis, 2007, 247(2), 307-32.
Czernik, S. et al., "Overview of Applications of Biomass Fast Pyrolysis Oil," Energy & Fuels, 2004, 18, 590-598.
Dao, L.H. et al., "Direct Catalytic Thennoconversion of Biomass into Liquid Fuels and Chemical Feedstocks," Proceedings of the Fifth Canadian Bioenergy R&D Seminar, 1984, 460(4), pp. 460-464.
Dao, L.H. et al., "Reactions of Biomass Pyrolysis Oils Over ZSM-5 Zeolite Catalysts," Proceedings of National Meeting of American Chemical Society, Division of Fuel Chemistry, Denver, CO, 1987, 32:2, 308-316.
Dao, L.H. et al., "Reactions of Model Compounds of Biomass-Pyrolysis Oils over ZSM-5 Zeolite. Catalysts," American Chemical Society, ACS Symposium Series, 1988, 376, 328-341.
Degnan, T.F. et al., "History of ZSM-5 fluid catalytic cracking-additive development at Mobil," Microporous and Mesoporous Materials, 2000, 35-36, 245-252.
Demirbas, A., "Conversion of Biomass to a Pyrolytic Oil for Blending Gasoline as an Alternative Fuel in Internal Combustion Engines," Energy Sources, 2001, 23, 553-562.
Demirbas, A., "Production of Gasoline and Diesel Fuels from Bio-materials," Energy Sources, Part A, 2007, 29, 753-760.
Diebold, J. et al., "Biomass to Gasoline (BTG): Upgrading Pyrolysis Vapors to Aromatic Gasoline with Zeolite Catalysis at Atmospheric Pressure," Proceedings of National Meeting of American Chemical Society, Division of Fuel Chemistry, Denver, CO, 1987, 32:2, 297-307.
Dozeman, G. et al., "Production of Liquid Chemicals and Fuels From Cellulosics by Catalytic Conversion of Intermediate Sugars," Energy of Biomass and Wastes, 1991, 1063-1089.
Elordi, G. et al., "Catalytic Pyrolysis of High Density Polyethylene in a Conical Spouted Bed Reactor," J. Anal. Appl. Pyrolysis, 2007, 79, 450-455.
Elordi, G. et al., "Catalytic Pyrolysis of High Density Polyethylene on a HZSM-5 Zeolite Catalyst in a Conical Spouted Bed Reactor," International Journal of Chemical Reactor Engineering, 2007, 5, Article A72, 1-9.
Encinar, J., et al., "Catalyzed Pyrolysis of Grape and Olive Bagasse. Influence of Catalyst Type and Chemical Treatment," Ind. Eng. Chem. Res., 1997, 36, 4176-4183.
Evans, R. et al., "Molecular-Beam, Mass-Spectrometric Studies of Wood Vapor and Model Compounds over HZSM-5 Catalyst," Proceedings of National Meeting of American Chemical Society, Division of Fuel Chemistry, Denver, CO, 1987, 32:2, 287-296.
Fabbri, D. et al., "Effect of zeolites and nanopowder metal oxides on the distribution of chiral anhydrosugars evolved from pyrolysis of cellulose: An analytical study," J. Anal. Appl. Pyrolysis, 2007, 80, 24-29.
Fan, Y. et al., "Acidity Adjustment of HZSM-5 Zeolites by Dealumination and Realumination with Steaming and Citric Acid Treatments," J. Phys. Chem. B, 2006, 110, 15411-15416.
Froment, G., "Coke Formation in Catalytic Processes: Kinetics and Catalyst Deactivation," *Catalyst Deactivation*, Edited by C. Bartholomew et al., 1997, 53-68.
Gayubo, A.G. et al., "Deactivation of a HZSM-5 Zeolite Catalyst in the Transformation of the Aqueous Fraction of Biomass Pyrolysis Oil into Hydrocarbons," Energy & Fuels, 2004, 18, 1640-1647.
Gayubo, A.G. et al., "Transformation of Oxygenate Components of Biomass Pyrolysis Oil on a HZSM-5 Zeolite. II. Aldehydes, Ketones, and Acids," Ind. Eng. Hem. Res., 2004,43, 2619-2626.
Gayubo, A.G. et al., "Undesired Components in the Transformation of Biomass Pyrolysis Oil into Hydrocarbons on an HZSM-5 Zeolite Catalyst," J. Chem Technol. Biotechnol, 2005, 80, 1244-1251.
Gonzalez-Tejera, M.J., et al. "Polyfuran Conducting Polymers: Synthesis, properties, and applications," Synthetic Metals, 2008, 158, 165-189.

(56) References Cited

OTHER PUBLICATIONS

Goyal, H.B. et al., "Bio-fuels from Thermochemical Conversion of Renewable Resources: A Review," Renewable & Sustainable Energy Reviews, 2008, 12, 504-517.

Grandmaison, J. et al., "Conversion of Furanic Compounds over H-ZSM-5 Zeolite," Fuel, 1999, 69, 1058-1061.

Gullu, D. "Effect of Catalyst on Yield of Liquid Products from Biomass via Pyrolysis," Energy Sources, 2003, 25, 753-765.

Gutierrez-Alejandre, A. et al., "FT-IR evidence of the interaction of benzothiophene with the hydroxyl groups of H-MFI and H-MOR zeolites," Vibrational Spectroscopy, 2006, 41, 42-47.

Halpern, Y. et al., "Levoglucosenone (1,6-Anhydro-3,4-dideoxy-$\Delta^3$-$\beta$-D-Pyranonsen-2-one). A Major Product of the Acid-Catalyzed Pyrolysis of Cellulose and Related Carbohydrates," J. Org. Chem., 1973, 38 (2), 204-209.

Hanniff, I.M. et al., "Conversion of Biomass Carbohydrates into Hydrocarbon Products," Energy from Biomass and Wastes, 1987, 10, 831-843.

Herring, A.H. et al., "Separating Gas Phase from Solid Phase Chemistry and Identifying the Reactive Intermediates Involved in the Pyrolysis of Biomass Chars.," Prepr. Pap. Am. Soc., Div. Fuel Chem., 2005, 50 (1), 161-162.

Horne, P.A. et al., "Catalytic Coprocessing of Biomass-derived Pyrolysis Vapours and Methanol," Journal of Analytical and Applied Pyrolysis, 1995, 34, 87-108.

Horne, P.A. et al., "Premium Quality Fuels and Chemicals from the Fluidised Bed Pyrolysis of Biomass with Zeolite Catalyst Upgrading," Renewable Energy, 1994, 5, Part II, 810-812.

Horne, P.A. et al., "Reaction of Oxygenated Biomass Pyrolysis Model Compounds over a ZSM-5 Catalyst," Renewable Energy, 1996, 7 (2), 131-144.

Iliopoulou, E.F. et al., "Catalytic Conversion of Biomass Pyrolysis Products by Mesoporous Materials: Effect of Steam Stability and Acidity of Al-MCM-41 Catalysts," Chemical Engineering Journal, 2007, 134, 51-57.

Islam, M.N. et al., "Techno-economics of Rice Husk Pyrolysis, Conversion with Catalytic Treatment to Produce Liquid Fuel," Bioresource Technology, 2000, 73, 67-75.

Janssen, F., "Catalysis for Renewable Energy and Chemicals, The Thermal Conversion of Biomass," Chapter 2: *Environmental Catalysis*, Edited by F. Janssen et al., Imperial College Press, 1999, 15-36.

Karge, H.G. et al., "In-situ FTIR Measurements of Diffusion in Coking Zeolite Catalysts," Applied Catalysis A: General, 1996, 146, 339-349.

Kersten, S. et al., "Options for Catalysis in the Thermochemical Conversion of Biomass into Fuels," *Catalysis for Renewables: From Feedstock to Energy Production*, Edited by G. Centi et al., 2007, 119-145.

Kim, Y. et al., "A Technical and Economic Evaluation of the Pyrolysis of Sewage Sludge for the Production of Bio-oil," Bioresource Technology, 2008, 99, 1409-1416.

Kuroda, K. et al., "Thermal Behavior of $\beta$-1 Subunits in Lignin: Pyrolysis of 1,2-Diarylpropane-1,3-diol-type Lignin Model Compounds," J. Agric. Food Chem., 2007, 55, 2770-2778.

Langley, J.T. et al., "Pyrolysis and Combustion of Cellulose. VII. Thermal Analysis of the Phyosphorylation of Cellulose and Model Carbohydrates During Pyrolysis in the Presence of Aromatic Phosphates and Phosphoramides," Journal of Applied Polymer Science, 1980, 25, 243-262.

Lappas, A.A. et al., "Biomass Pyrolysis in a Circulating Fluid Bed Reactor for the Production of Fuels and Chemicals," Fuel, 2002, 81, 2087-2095.

Lauer, M., "Implementation of Biomass Fast Pyrolysis in Highly Competitive Markets," Proceedings of the 4th Biomass Conference of the Americas, 1999, 2, 1263-1268.

Lee, H.I. et al., "Synthesis of Highly Stable Mesoporous Aluminosilicates from Commercially Available Zeolites and their Application to the Pyrolysis of Woody Biomass," Catalysis Today, 2008, 132, 68-74.

Leung, A. et al., "Pathway for the Catalytic Conversion of Carboxylic Acids to Hydrocarbons over Activated Alumina," Energy & Fuels, 1995, 9, 913-920.

Li, J. et al., "Preparation of Nano-NiO Particles and Evaluation of their Catalytic Activity in Pyrolyzing Biomass Components," Energy & Fuels, 2008, 22, 16-23.

Li, L. et al., "Pyrolysis of Waste Paper. Characterization and Composition of Pyrolysis Oil," Energy Sources, 2005, 24, 867-873.

Li, X. et al., "Effects of Large Pore Zeolite Additions in the Catalytic Pyrolysis Catalyst on the Light Olefins Production," Catalysis Today, 2007, 125, 270-277.

Lima, D.G. et al., "Diesel-like Fuel Obtained by Pyrolysis of Vegetable Oils," Journal of Analytical and Applied Pyrolysis, 2004, 71, 987-996.

Lourvanij, K. et al., "Reaction Rates for the Partial Dehydration of Glucose to Organic Acids in Solid-Acid, Molecular-Sieving Catalyst Power," J. Chem. Tech. Biotechnol., 1997, 69, 35-44.

Lourvanij, K. at al., "Reactions of Aqueous Glucose Solutions over Solid-Acid Y-Zeolite Catalyst at 110-160 ° C.," Ind. Eng. Chem. Res., 1993, 32, 11-19.

LV, P. et al., "A Kinetic Study on Biomass Fast Catalytic Pyrolysis," Energy & Fuels, 2004, 18, 1865-1869.

Malherbe, R.R. et al., "Furfural Oligomerization with H-Fe-FAU Zeolite," Journal of Materials Science Letters, 1993, 12, 1037-1038.

Marcilla, A. et al., "Kinetic Study of Polypropylene Pyrolysis using ZSM-5 and an Equilibrium Fluid Catalytic Cracking Catalyst," Journal of Analytical and Applied Pyrolysis, 2003, 68-69, 467-480.

Matsuzawa, Y. et al., "Evaluation of Char Fuel Ratio in Municipal Pyrolysis Waste," Fuel, 2004, 83, 1675-1687.

McGrath, T. et al., "Low Temperature Mechanism for the Formation of Polycyclic Aromatic Hydrocarbons from the Pyrolysis of Cellulose," J. Anal. Apl. Prolysis, 2003, 66, 51-70.

Meier, D. et al., "State of the Art of Applied Fast Pyrolysis of Lignocellulosic Materials—a Review," Bioresource Technology, 1999, 68, 71-77.

Milne, T.A. et al., "Molecular Beam Mass Spectrometric Studies of HZSM-5 Activity During Wood Pyrolysis Product Conversion," International Conference on Research in Thermochemical Biomass Conversion, 1998, 910-926.

Morris, K., "Fast Pyrolysis of Bagasse to Produce BioOil Fuel for Power Generation," International Sugar Journal, 2001, 103, (1230), 259-263.

Mullen, C. et al., "Chemical composition of Bio-oils Produced by Fast Pyrolysis of Two Energy Crops," Energy&Fuels, Published online Apr. 19, 2008.

Netrabukkana, R. et al., "Diffusion of Glucitol in Microporous and Mesoporous Silicate/Aluminoslicate Catalysts," Ind. Eng. Chem. Res., 1996, 35, 458-464.

Nokkosmäki, M.I. et al., "Catalytic Conversion of Biomass Pyrolysis Vapours with Zinc Oxide;" Journal of Analytical and Applied Pyrolysis, 2000, 55, 119-131.

Nováková, J. et al., "Effect of Heat Treatment on the Character of Coke Deposited on HZSM-5 and HY Zeolites in Acetone Conversion," Zeolites, 1991, 11, 135-141.

Oasmaa, A. et al., "Norms and Standards for Pyrolysis Liquids. End-User Requirements and Specifications," Energy & Fuels, 2005, 19, 2155-2163.

Olazar, M. et al., "Pyrolysis of Sawdust in a conical spouted-bed reactor with a HZSM-5 catalyst," AIChE Journal, 2000, 45, 1025-1033.

Onay, O., "Fast and Catalytic Pyrolysis of Pistacia Khinjuk Seed in a Well Swept Fixed Bed Reactor," Fuel, 2007, 86, 1452-1460.

Paine III, J.B. et al., "Carbohydrates Pyrolysis Mechanisms From Isotopic Labeling Part 1: The Pyrolysis of Glycerin; Discovery of competing fragmentation mechanisms affording acetaldehyde and formaldehyde and the implications for carbohydrates pyrolysis," J. Anal. Appl. Pyrolysis, 2007, 80, 297-311.

Pakdel, H. et al., "Analysis of Wood Vacuum Pyrolysis Solid Residues by Diffuse Reflectant Infrared Fourier Transform Spectrometry," Can. J. Chem., 1989, 67, 310-314.

Pakdel, H. et al., "Chemical Characterization of Wood Pyrolysis Oils Obtained in a Vacuum-Pyrolysis Multiple-Hearth Reactor," American Chemical Society Symposium Series, 1988, 376, 203-219.

(56) References Cited

OTHER PUBLICATIONS

Park, H.J. et al., "Conversion of the Pyrolytic Vapor of Radiata Pine over Zeolites," J. Ind. Eng. Chem., 2007, 13 (2), 182-189.
Pasel, C. et al., "Experimental Investigations on reactor Scale-up and Optimisation of Product Quality in Pyrolysis of Shredder Waste," Fuel Processing Technology, 2003, 80, 47-67.
Pattiya, A. et al., "Catalytic Pyrolysis of Cassava Rhizome," 2nd Joint International Conference on Sustainable Energy and Environment Technology and Policy Innovations, Bangkok, Thailand, 2006, 1-6.
Pattiya, A. et al., "Fast Pyrolysis of Cassava Rhizome in the Presence of Catalysts," J. Anal. Appl. Pyrolysis, 2008, 81, 72-79.
Pavlath, A.E. et al., "Carbohydrate Pyrolysis, II. Formation of Furfural and Furfuryl Alcohol During the Pyrolysis of Section Carbohydrates with Acidic and Basic Catalysts," Proceedings of International Conference on Research in Thermochemical Biomass Conversion, Phoenix, AZ, 1988, 155-163.
Piskorz, J., "Fast Pyrolysis of Pretreated Wood," Proceedings, Second Biomass Conference of The Americas, Portland, OR, 1995, 1151-1160.
Putuin, E. et al., "Fixed-bed Catalytic Pyrolysis of Cotton-seed Cake: Effects of Pyrolysis Temperature Nature Zeolite Content and Sweeping Gas Flow Rate," Bioresource Technology, 2006, 97, 701-710.
Qi, W.Y. et al., "Catalytic Pyrolysis of Several Kinds of Bamboos over Zeolite NaY," Green Chem., 2006, 8, 183-190.
Renaud, M. et al., "Conversion of Vacuum Paralytic Oils from Populus Deltoides over H-ZSM-5," Proceedings of National Meeting of American Chemical Society, Division of Fuel Chemistry, Denver, CO, 1987, 32:2, 276-286.
Ritter, S., "A Fast Track to Crreen Gasoline," Chemical and Engineering News, 2008, 10.
Sahoo, S.K. et al., "Studies on Acidity, Activity and Coke Deactivation of ZSM-5 during $n$-heptane Aromatization," Applied Catalysis A: General, 2005, 205, 1-10.
Samolada, M.C. et al. "Catalyst Evaluation for Catalytic Biomass Pyrolysis," Energy & Fuels, 2000, 14, 1161-1167.
Samolada, M.C. et al., "Catalytic Cracking of Biomass Flash Pyrolysis Liquids," Developments in Thermochemical Biomass Conversion, 1997, 1, 657-671.
Samolada, M.C. et al., "Production of a Bio-Gasoline by Upgrading BFPLS via Hydrogen Processing and. Catalytic Cracking," Fuel, 1998, 77, (14), 1667-1675.
Sanchez, R. et al., "Structural Characterization of the Polymeric Lattice of Furfuraldehyde Resins," Polymer Testing, 1998, 17, 395-401.
Sanders, E.B. et al., "A Model that Distinguishes the Pyrolysis of D-glucose, D-fructose, and sucrose from that of Cellulose. Application to the understanding of cigarette smoke formation," J. Anal. Appl. Pyrolysis, 2003, 66, 29-50.
Sarbak, Z., "Fourier-Transform Infrared Studies on Coke Formation over Alumina Silica-Alumina and Zeolites," React. Kinet. Catal. Lett., 2000, 69 (1),177-181.
Scahill, J. et al., "Engineering Aspects of Upgrading Pyrolysis Oil Using Zeolites," *Research in Thermochemical Biomass Converstion*., Edited by Bridgwater et al., 1988, 927-40.
Scott, D.S. et al., "Feasibility Study for a Biomass Refinery Concept," Making a business from biomass in energy, environment, chemicals, fibers, and materials; Proceedings of the $3^{rd}$ Biomass Conference of the Americas, M, 1997, 2, 933-944.
Serio, M.A. et al., "Measurement and Modeling of Lignin Pyrolysis," Biomass and Bioenergy, 1994, 7 (1-6), 107-124.
Sharma, R.K. et al., "Catalytic Upgrading of Fast Pyrolysis Oil Over HZSM-5," The Canadian Journal of Chemical Engineering, 1993, 71, 383-391.
Sharma, R.K. et al., "Catalytic Upgrading of Pyrolysis Oil," Energy & Fuels, 1993, 7, 306-314.
Spath, P. et al., "Options for Thermochemical Processing of Biomass," Proceedings of the Second Biomass Conference of the Americas, 1995, Issue 607, 607-613.
Stocker, M., Methanol-to-hydrocarbons: catalytic materials and their behavior Microporous and Mesoporous Materials, 1999, 29, 3-48.

Sulman, E. et al., "Catalysis in Energy-saving Technologies for Fuel Production on the . . . ," Kataliz V Promyshlennosti, 2004, 5, 43-49.
Sulman, E.M. et al., "The Development of the Method of Low-Temperature Peat Pyrolysis on the Basis of Altunosilicate Catalytic System," Chemical Engineering Journal, 2007, 134, 162-167.
Telysheva, G. et al., "Characterization of the Transformations of Lignocellulosic Structures Upon Degradation in Planted Soil," J. Anal. Appl. Pyrolysis, 2007, 79, 52-60.
Toft, A.J. et al., "An Evaluation of Alternative Systems for Electricity Generation from Biomass," The 1996 ICHEME Research Event, 1996, 2, 552-554.
Torre, I. et al., "Catalytic Cracking of Plastic Pyrolysis Waxes with Vacuum Gasoil: Effect of HZSM-5 Zeolite in the FCC Catalyst," International Journal of Chemical Reactors Engineering, 2006, 4, Article A31, 1-17.
Van Santen, R.A., "Renewable Catalytic Technologies—a Perspective," *Catalysis for Renewables; from Feedstock to Energy Production*, 2007, 1-20.
Venderbosch, R. et al., "Flash Pyrolysis of Wood for Energy and Chemicals," NPT Procestechnologies, 2000, 7 (1),16-19.
Wang, X., "Biomass Fast Pyrolysis in a Fluidized Bed—Product cleaning by in-situ filtration," PhD Thesis, University of Twente, 2006, 1-191.
Weisz, P.B. et al., "Catalytic Production of High-Grade Fuel (Gasoline) from Biomass Compounds by Shape-Selective Catalysis," Science, 1979, 206 (5), 57-58.
Westerhof, R. et al., "Controlling the Water Content of Biomass Fast Pyrolysis Oil," Ind. Eng. Chem. Res, 2007, 46, 9238-9247.
Williams, P.T. et al., "Comparison of Products from the Pyrolysis and Catalytic Pyrolysis of Rice Husks," Energy, 2000, 25, 493-513.
Williams, P.T. et al., "Fluidised Bed Pyrolysis and Catalytic Pyrolysis of Scrap Tyres," Environmental Technology, 2003, 24, 921-929.
Williams, P.T. et al., "The Influence of Catalyst Regeneration on the Composition of Zeolite-upgraded Biomass Pyrolysis Oils," Fuel, 1995, 74 (12), 1839-1851.
Williams, P.T. et al., "The influence of Catalyst Type on the Composition of upgraded Biomass Pyrolysis Oils," Journal of Analytical and Applied Pyrolysis, 1995, 31, 39.61.
Wooten J.B. et al., "Observation and Characterization of Cellulose Pyrolysis Intermediates by $^{13}C$ CPMAS NMR. A New Mechanistic Model," Energy&Fuels—An American Chemical Society Journal, 2004, 18(1), 1-15.
Xiao, B. et al., "Chemical, Structural, and Thermal Characterizations of Alkali-soluble Lignins and Hemicelluloses, and Cellulose from Maize Stems, Rye Straw, and Rice Straw," Polymer Degradation and Stability, 2001, 74, 307-319.
Yaman, S., "Pyrolysis of Biomass to Produce Fuels and Chemical Feedstocks," Energy Conversion and Management, 2004, 45, 651-671.
Zabaniotou, A. et al., "Experimental Study of Pyrolysis for Potential Energy, Hydrogen and Carbon Material Production from Lignocellulosic Biomass," International Journal of Hydrogen Energy, 2008, 33, 2433-2444.
Zawadzki, J., "Infrared Spectroscopy Studies on Surface functional Groups of Carbons. II. Carbonization of Poly(furfuryl alcohol)," Chemia Stosowana, 1997, 23, (2), 229-240.
Zhang, J. et al., "Product Analysis and Thermodynamic Simulations from the Pyrolysis of Several Biomass Feedstocks," Energy & Fuels, 2007, 21, 2373-2385.
Zhenyi, C. et al., "Thermodynamics Calculation of the Pyrolysis of Vegetable Oils," Energy Sources, 2004, 26, 849-856.
Ringer et al.; "Large-Scale Pyrolysis Oil Production: A Technology Assessment and Economic Analysis"; NREL National Renewable Energy Laboratory; Technical Report, NREL/TP-510-37779, Nov. 2006.
Japanese Office Action, Application No. 2012-528792, mailed Sep. 2, 2014, English Translation.
Chinese Office Action, Application No. 201080050229.6, issued Apr. 23, 2015.

* cited by examiner

| Zeolite | Norman Radii Adjusted Pore Size (Å) |
|---|---|
| MCM-22 | 6.2 |
| ZSM-23 | 5.9 |
| ZSM-57 | 6.1 |
| Ferrierite | 6.1 |
| SUZ-4 | 5.9 |
| EU-1 | 6.1 |
| ZSM-11 | 6.1 |
| (S)AlPO-31 | 6.1 |
| SSZ-23 | 6 |

FIG. 17 ns (e.g., ~500° C./sec) to intermediate temperatures (e.g., ~400-500° C.) followed by rapid cooling (e.g., residence times 1-2 s). (See, A. V. Bridgwater, Fast Pyrolysis of Biomass: A Handbook Volume 2, CPL Press, Newbury, UK, 2002.) Conventional fast pyrolysis often produces a thermally unstable liquid product mixture called bio-oils, an acidic combustible liquid mixture of more than 300 compounds that degrades with time. However, bio-oils are not compatible with existing liquid transportation fuels, such as gasoline and diesel, and yields are low.

SYSTEMS AND PROCESSES FOR CATALYTIC PYROLYSIS OF BIOMASS AND HYDROCARBONACEOUS MATERIALS FOR PRODUCTION OF AROMATICS WITH OPTIONAL OLEFIN RECYCLE, AND CATALYSTS HAVING SELECTED PARTICLE SIZE FOR CATALYTIC PYROLYSIS

RELATED APPLICATIONS

This application claims priority under 35 U.S.C. §119(e) to U.S. Provisional Patent Application No. 61/241,018, filed Sep. 9, 2009, and entitled "Systems and Processes for Catalytic Pyrolysis of Biomass and Hydrocarbonaceous Materials for Production of Aromatics with Optional Olefin Recycle, and Catalysts Having Selected Particle Size for Catalytic Pyrolysis," which is incorporated herein by reference in its entirety for all purposes.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. CBET-0747996 awarded by the National Science Foundation.

FIELD OF INVENTION

This invention relates to compositions and methods for the production of biochemicals such as biofuel, aromatic, and olefin compounds, and more specifically, to compositions and methods for biochemical production via catalytic pyrolysis.

BACKGROUND

With its low cost and wide availability, lignocellulosic biomass has been under worldwide-study as a feedstock for renewable liquid biofuels. One impetus, in particular, is that biomass derived fuels have zero net $CO_2$ emissions if produced without the use of fossil fuels. However, lignocellulosic biomass is not currently commonly used as a liquid fuel source because typical current conversion processes are not considered to be economically feasible. Several routes are being examined to convert solid biomass to a liquid fuel. At low temperatures (e.g., 200-260° C.) diesel range alkanes can be produced by a multi-step aqueous-phase processing (APP) of aqueous carbohydrate solutions involving dehydration, aldol-condensation and dehydration/hydrogenation (G. W. Huber, J. A. Dumesic, Catalysis Today 2006, 111, 119-132.). However, APP requires that solid lignocellulosic biomass first be converted into aqueous carbohydrates. At higher temperatures (~800° C.) solid biomass can be reformed to produce synthesis gas through partial oxidation over catalysts in an auto thermal packed bed reactor. (P. J. Dauenhauer, J. D. Dreyer, N. J. Degenstein, L. D. Schnudt, Angew. Chem. Int. Ed. 2007, 46, 5864-5867.). The synthesis gas produced from the reaction can be fed to a secondary process to make fuels and chemicals. For certain applications, an ideal process for solid biomass conversion may involve the production of a liquid fuel that fits into existing infrastructure from solid biomass in a single step, at short residence times. Unfortunately, neither the APP nor syngas process meets such criteria.

Another approach for biofuel production is fast pyrolysis, which can involve, for example, rapidly heating biomass Accordingly, there remains an on-going search in the art for an economical, efficient route for the production of useful biofuels and related compounds from solid biomass.

SUMMARY OF THE INVENTION

This invention relates generally to compositions and methods for the production of biochemicals such as biofuel, aromatic, and olefin compounds. The subject matter of this invention involves, in some cases, interrelated products, alternative solutions to a particular problem, and/or a plurality of different uses of one or more systems and/or articles.

In one aspect, a method for producing one or more fluid hydrocarbon products from a hydrocarbonaceous material is provided. The method may comprise feeding a hydrocarbonaceous material to a reactor, and pyrolyzing within the reactor at least a portion of the hydrocarbonaceous material under reaction conditions sufficient to produce one or more pyrolysis products. In some embodiments, the method may comprise catalytically reacting within the reactor at least a portion of the one or more pyrolysis products under reaction conditions sufficient to produce one or more fluid hydrocarbon products comprising olefins and aromatics, separating at least a portion of the olefins in the fluid hydrocarbon products to produce a recycle stream comprising at least the separated olefins, and a product stream, and feeding at least a portion of the recycle stream to the reactor.

In some embodiments, the method may comprise feeding a solid hydrocarbonaceous material to a reactor, pyrolyzing within the reactor at least a portion of the solid hydrocarbonaceous material under reaction conditions sufficient to produce one or more pyrolysis products, and catalytically reacting at least a portion of the one or more pyrolysis products under reaction conditions sufficient to produce one or more fluid hydrocarbon products comprising olefins and aromatics. In some cases, the method may further comprise separating at least a portion of the olefins in the one or more fluid hydrocarbon products to produce a recycle stream comprising at least the separated olefins and a product stream, and feeding at least a portion of the recycle stream to the reactor.

In some instances, the method may comprise providing a hydrocarbonaceous material and one or more catalysts comprising a plurality of particles having maximum cross-sectional dimensions of less than about 1 micron, and pyrolyzing at least a portion of the hydrocarbonaceous material under reaction conditions sufficient to produce one or more pyrolysis products. In some cases, the method may further comprise catalytically reacting at least a portion of the pyrolysis products with the catalysts to produce one or more hydrocarbon products.

The method can comprise, in some embodiments, providing a hydrocarbonaceous material and a zeolite catalyst comprising gallium, pyrolyzing at least a portion of the hydrocarbonaceous material under reaction conditions sufficient to produce one or more pyrolysis products, and catalytically reacting at least a portion of the pyrolysis products with the catalysts to produce the one or more hydrocarbon products Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of this invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 17 includes a table of exemplary Norman radii adjusted pore sizes of zeolite catalysts, according to one set of embodiments;

DETAILED DESCRIPTION

Figure 1:
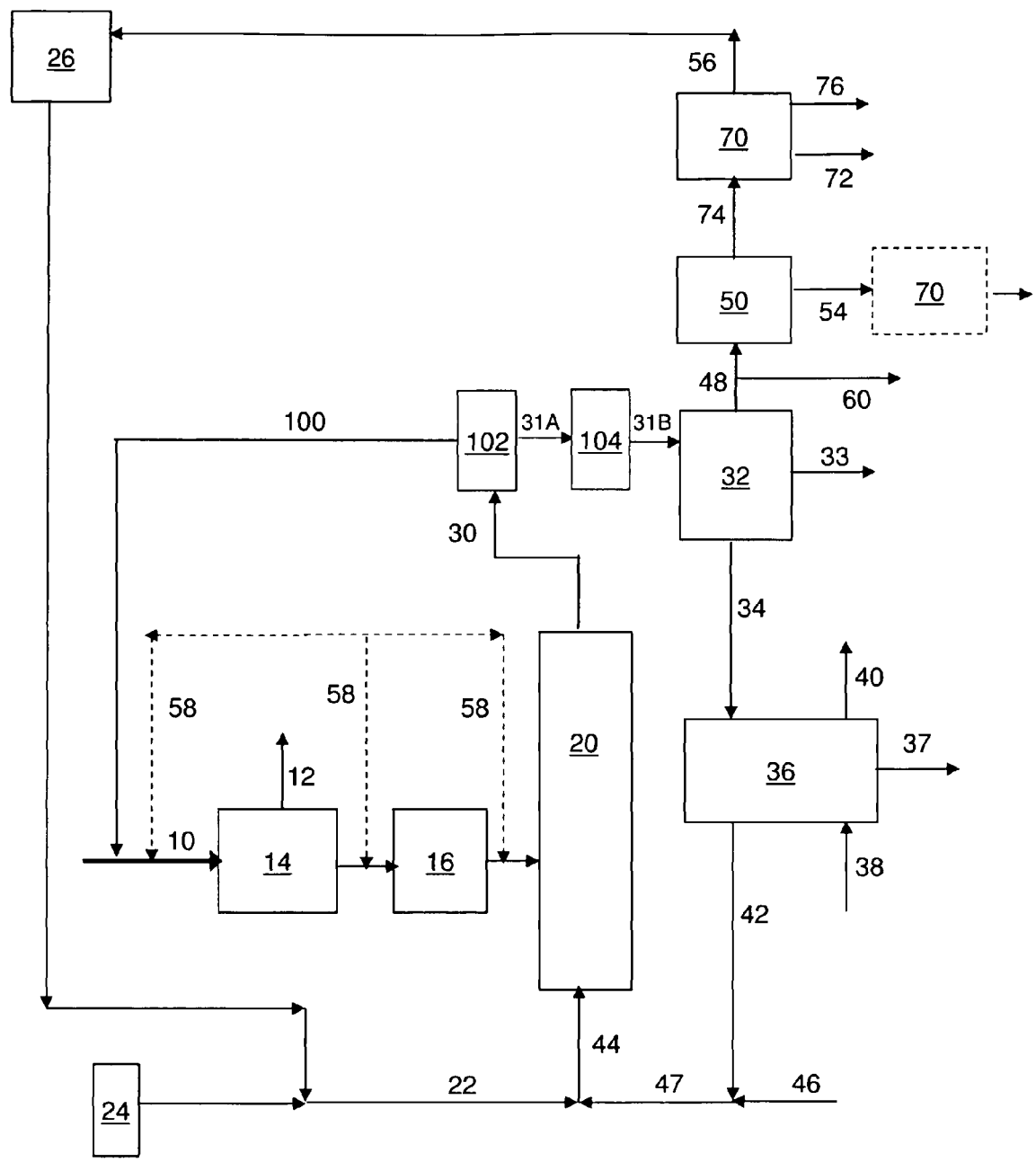
FIG. 1 is a schematic diagram of a catalytic pyrolysis process, according to one set of embodiments.

The specification discloses inventive compositions and methods for the production of biochemicals such as biofuel, aromatic, and olefin compounds, and more specifically, compositions and methods for the production of biochemicals via catalytic pyrolysis. Some embodiments relate to methods for the production of fluid (e.g., a liquid, a supercritical fluid, and/or a gas) hydrocarbon products such as aromatic compounds (e.g., benzene, toluene, naphthalene, xylene, etc.) and olefins (e.g., ethene, propene, butene, etc.) via catalytic pyrolysis processes (e.g., catalytic fast pyrolysis). In certain embodiments, the hydrocarbon products or a portion thereof are liquids at standard ambient temperature and pressure (SATP—i.e. 25 degrees C. and 100 kPa absolute pressure). Some such methods may involve the use of a composition comprising a mixture of a hydrocarbonaceous material, for example a liquid, gaseous and/or solid hydrocarbonaceous material, and a heterogeneous pyrolytic catalyst component. In some embodiments, hydrocarbonaceous material can be fed to a reactor, undergo catalytic pyrolysis, and a portion the product stream can be recycled to the feed stream comprising the hydrocarbonaceous material. In one particular embodiment, a portion of the olefins in the product stream are selectively recycled to the feed stream. Such embodiments may be useful, for example, in increasing the amount of aromatic compounds present in the product stream, relative to the amount of aromatic compounds that would be present in the product stream in the absence of recycling (e.g. olefin recycling) but under essentially identical conditions.

In some embodiments, the mixture may be pyrolyzed at high temperatures (e.g., between 500° C. and 1000° C.). The pyrolysis may be conducted for an amount of time at least partially sufficient for production of discrete, identifiable fluid hydrocarbon products. Some embodiments involve heating the mixture of catalyst and hydrocarbonaceous material at relatively high heating rates (e.g., from about 400° C. per second to about 1000° C. per second). The methods described herein may also involve the use of specialized catalysts. For example, in some cases, zeolite catalysts are used; optionally, the catalysts used herein may have high silica to alumina molar ratios. The catalyst can, in some cases, be formed of or comprise relatively small particles, which may be agglomerated. In some instances, the composition fed to the pyrolysis reactor has a relatively high catalyst to hydrocarbonaceous material mass ratio (e.g., from about 5:1 to about 20:1).

Some embodiments can be directed to a single-stage method for the pyrolysis of biomass. Such a method can comprise providing or using a single-stage pyrolysis apparatus. A single-stage pyrolysis apparatus is one in which pyrolysis and subsequent catalytic reactions are carried out in a single vessel. In some embodiments, the single-stage pyrolysis apparatus comprises a fluidized bed reactor. Multi-stage apparatuses can also be used for the production of fluid hydrocarbon products, as described in more detail below.

As used herein, the terms "pyrolysis" and "pyrolyzing" are given their conventional meaning in the art and are used to refer to the transformation of a compound, e.g., hydrocarbonaceous material, into one or more other substances, e.g., volatile organic compounds, gases and coke, by heat alone without oxidation, which may take place with or without the use of a catalyst. "Catalytic pyrolysis" refers to pyrolysis performed in the presence of a catalyst, and may involve steps as described in more detail below. Example of catalytic pyrolysis processes are outlined, for example, in Huber, G. W. et al, "Synthesis of Transportation Fuels from Biomass: Chemistry, Catalysts, and Engineering," *Chem. Rev.* 106, (2006), pp. 4044-4098, which is incorporated herein by reference in its entirety.

As used herein, the term "biomass" is given its conventional meaning in the art and is used to refer to any organic source of energy or chemicals that is renewable. Its major components can be (1) trees (wood) and all other vegetation; (2) agricultural products and wastes (corn, fruit, garbage ensilage, etc.); (3) algae and other marine plants; (4) metabolic wastes (manure, sewage); and (5) cellulosic urban waste. Examples of biomass materials are described, for example, in Huber, G. W. et al, "Synthesis of Transportation Fuels from Biomass: Chemistry, Catalysts, and Engineering," *Chem. Rev.* 106, (2006), pp. 4044-4098.

The inventors have discovered within the context of the invention that for some reactions, certain changes in reaction conditions and combinations of such changes can produce favorable products and/or yields, lower yields of coke formation and/or more controlled product formation (e.g., higher production of aromatics and/or olefins relative to other fuels) that may not otherwise be obtained but for the changes in reaction conditions. For example, the incorporation of a recycle stream comprising olefins can produce a relatively high amount of aromatic compounds and/or low amount of coke in the product stream, relative to an amount of aromatic compounds and/or coke that would be produced in the absence of the recycle stream. As another example, the use of elevated temperatures (e.g., in the reactor and/or the solids separator) may produce favorable products and/or yields from reactions that may not occur at lower temperatures. The inventors have also discovered within the context of the invention that it may be advantageous, in some cases, to heat the feed stream (e.g., a gaseous or liquid hydrocarbonaceous material, a solid hydrocarbonaceous material, a mixture of a solid hydrocarbonaceous material and a solid catalyst, etc.) at a relatively fast rate as it enters the reactor. Also, the inventors have found that providing a feed with a high mass ratio of catalyst to hydrocarbonaceous material may produce desirable yields of aromatic and/or olefin products. For example, without wishing to be bound by theory, the inventors currently believe that high heating rates and high catalyst-to-feed mass ratios may facilitate introduction of volatile organic compounds, formed from pyrolysis of the hydrocarbonaceous feed, into the catalyst before they thermally decompose, thus leading to high yields of aromatic and/or olefin compounds. Relatively low mass-normalized space velocities have also shown to produce desirable yields of aromatic and/or olefin compounds. In addition, the inventors have discovered that relatively long residence times of hydrocarbonaceous material in high-temperature components of the system (e.g., the reactor and/or the solids separator) may allow adequate time for additional chemical reactions to form desirable products.

The inventors have also discovered within the context of the invention that the use of catalysts with specific properties may be useful in forming a relatively large amount of aromatic and/or olefin products. For example, in some cases, the use of catalysts comprising particles of relatively small sizes may result in the production of a relatively high amount of aromatic compounds and/or a relatively low amount of coke. As another example, in certain embodiments, ZSM-5, in combination with certain reaction conditions, was found to preferentially produce aromatic and/or olefin compounds. Additionally, certain catalysts that include Bronstead acid sites and/or well-ordered pore structures were found to selectively produce aromatic and/or olefin compounds in some cases. Catalyst pore size may also be used, in some cases, to affect the amounts and types of product compounds produced.

The embodiments described herein also involve chemical process designs used to perform catalytic pyrolysis. In some cases, the processes may involve the use of one or more fluidized bed reactors (e.g., a circulating fluidized bed reactor, turbulent fluidized bed reactor, bubbling fluidized bed reactor, etc.). The process designs described herein may optionally involve specialized handling of the material fed to one or more reactors. For example, in some embodiments, the feed material may be dried, cooled, and/or ground prior to supplying the material to a reactor. Other aspects of the invention relate to product compositions produced using the process designs described herein.

Without being bound to a particular mode of action or order of steps of the overall thermal/catalytic conversion process, catalytic pyrolysis is believed to involve at least partial thermal pyrolysis of hydrocarbonaceous material (e.g., solid biomass such as cellulose) to produce one or more pyrolysis products (e.g., volatile organics, gases, solid coke, etc.) and catalytic reaction of at least a portion of the one or more pyrolysis products using a catalyst under reaction conditions sufficient to produce fluid hydrocarbon products. The catalytic reaction may involve volatile organics entering into a catalyst (e.g., a zeolite catalyst) where they are converted into, for example, hydrocarbons such as aromatics and olefins, in addition to carbon monoxide, carbon dioxide, water, and coke. Inside or upon contact with the catalyst, the biomass-derived species may undergo a series of dehydration, decarbonylation, decarboxylation, isomerization, oligomerization, and dehydrogenation reactions that lead to aromatics, olefins, CO, $CO_2$ and water. A challenge with selective aromatic and/or olefin production is minimizing coke formation. For instance, the overall stoichiometries for conversion of xylitol and glucose to toluene, CO, and $H_2O$ are shown in Equations 1 and 2, respectively.

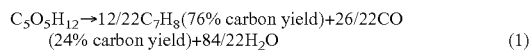

$$C_5O_5H_{12} \rightarrow 12/22 C_7H_8 (76\% \text{ carbon yield}) + 26/22 CO \\ (24\% \text{ carbon yield}) + 84/22 H_2O \quad (1)$$

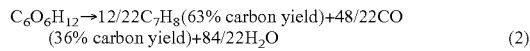

$$C_6O_6H_{12} \rightarrow 12/22 C_7H_8 (63\% \text{ carbon yield}) + 48/22 CO \\ (36\% \text{ carbon yield}) + 84/22 H_2O \quad (2)$$

Figure 9:
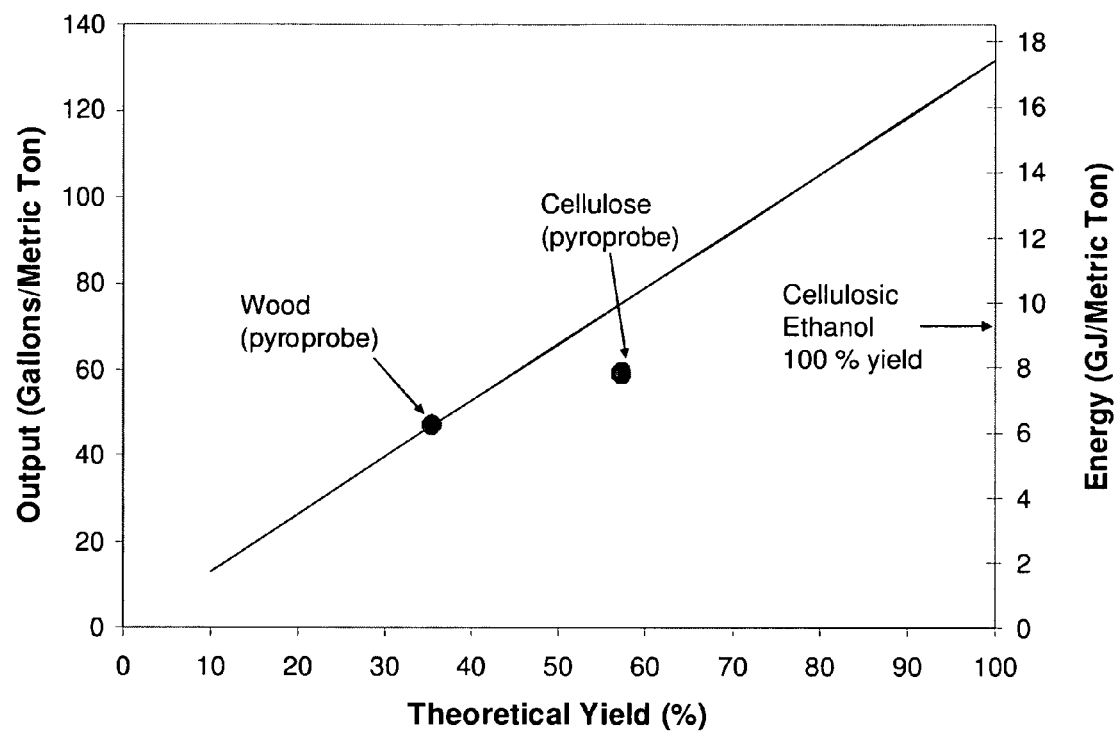
FIG. 9 includes a plot of the output of aromatics and the amount of energy per unit mass as a function of theoretical yield, according to one set of embodiments.

As shown in these equations, oxygen must be removed from the biomass-derived species as a combination of CO (or $CO_2$), and $H_2O$ when aromatics are produced. The maximum theoretical yields of toluene for xylitol and glucose are 76% and 63%, respectively. FIG. 9 includes a plot of the output of aromatics and the amount of energy per unit mass as a function of theoretical yield, according to one set of embodiments. In FIG. 9, the "Output" axis corresponds to the gallons of aromatics produced by the process per metric ton of biomass feed to the process. The "Energy" axis corresponds to the amount of energy (calculated using heats of combustion) in the aromatic products per metric ton of biomass fed to the process. The figure includes a curve showing the amount of aromatics produced divided by the amount of aromatics calculated from Equation 2, assuming that the feed biomass contains 75 wt % carbohydrates.

Other challenges associated with biomass conversion are the removal of oxygen and the enrichment of the hydrogen content of the hydrocarbon product. A factor, commonly referred to as the effective hydrogen to carbon molar ratio, $H/C_{eff}$, illustrates the chemistry required for efficient conversion of biomass-derived oxygenates.

$$\frac{H}{C_{eff}} = \frac{H - 2O}{C} \quad (3)$$

The $H/C_{eff}$ molar ratios of glucose, sorbitol and glycerol (all biomass-derived compounds) are 0, ⅓ and ⅔ respectively. By comparison, the $H/C_{eff}$ molar ratio of petroleum-derived feeds ranges from slightly larger than 2 (for liquid alkanes) to 1 (for benzene). In this respect, biomass can be viewed as hydrogen deficient, as compared to petroleum-based feedstocks.

Some such and other issues of fuel production can be addressed utilizing the methods and processes described herein. For instance, aromatics and/or olefins can be controllably produced from hydrocarbonaceous material feeds by controlling a variety of process parameters including, for example: catalyst selection (including type and physical properties (e.g., pore size, particle size, existence and degree of agglomeration, particle/agglomerate shape etc)), hydrocarbonaceous material selection, recycle ratios, recycle stream composition, heating rates, reaction temperature, catalyst to hydrocarbonaceous mass ratios (e.g., in the feed stream, in the reactor, etc.), catalyst silica to alumina molar ratios, mass-normalized space velocities, residence times in various processing components, among others. In some embodiments, process parameters may be selected such that coke formation rates are relatively low.

In one aspect, chemical processes for the reaction of hydrocarbonaceous material are described. The process may involve, in some embodiments, pyrolyzing within a reactor (e.g., a fluidized bed reactor) at least a portion of a hydrocarbonaceous material under reaction conditions sufficient to produce one or more pyrolysis products. In addition, the process may involve catalytically reacting at least a portion of the one or more pyrolysis products using a catalyst under reaction conditions sufficient to produce one or more fluid hydrocarbon products. In some embodiments, one or more fluid hydrocarbon products may be produced from said pyrolysis products by dehydration, decarbonylation, decarboxylation, isomerization, oligomerization, and dehydrogenation reactions. The pyrolysis and catalytic reaction processes may occur, in some cases, in a single reactor. The chemical processes may be used, in some cases, for specific fluid hydrocarbon product production (e.g., aromatics and/or olefins). In some cases, a portion of the olefins produced by the chemical process may be recycled into the feed stream via which the hydrocarbonaceous material is fed to the reactor (e.g., the pyrolysis reactor).

FIG. 1 includes a schematic illustration of an exemplary chemical process design used to perform catalytic pyrolysis, according to one set of embodiments. In some embodiments, such a process can be used to perform catalytic pyrolysis. As shown in the illustrative embodiment of FIG. 1, a feed stream 10 includes a feed composition comprising hydrocarbonaceous material that will be fed to a reactor 20. The hydrocarbonaceous material may generally comprise carbon and hydrogen, in which carbon is the most abundant component by mass, as well as minor proportions of other elements such as oxygen, nitrogen and sulfur. The hydrocarbonaceous material in the feed composition may comprise a solid, liquid, and/or gas. Specific examples of hydrocarbonaceous materials are provided below.

In some embodiments, the feed composition (e.g., in feed stream 10 of FIG. 1) comprises a mixture of hydrocarbonaceous material and a catalyst. The mixture may comprise, for example, solids, liquids, and/or gases. In certain embodiments, the mixture comprises a composition of a solid catalyst and a solid hydrocarbonaceous material. In other embodiments, a catalyst may be provided separately from the feed composition. A variety of catalysts can be used, as described in more detail below. For example, in some instances, zeolite catalysts with varying molar ratios of silica to alumina and/or varying pore sizes may be used.

One or more olefin compounds can be fed with the hydrocarbonaceous material and/or the catalyst, in some embodiments. The olefins may be of any suitable phase (e.g., solid, liquid, or gas). Examples of suitable olefin compounds that can be fed with the hydrocarbonaceous material include, but are not limited to, ethene, propene, butene, ethylene, butene, pentene, hexane, and the like. The olefins and the hydrocarbonaceous material can be fed as part of the same stream as the hydrocarbonaceous material and/or the catalyst, or the olefins can be fed separately from the hydrocarbonaceous material and/or the catalyst. In some embodiments, the olefins may originate from one or more product streams from the reactor and/or a downstream process, such as a separation process (i.e., the olefins may be part of a recycle stream). Olefins may be reacted with hydrocarbonaceous material in any suitable amount and proportion. A desired ratio of hydrocarbonaceous material to olefins can be achieved according to the invention, for example, by adjusting the flow rates of the hydrocarbonaceous material and the olefins, or by pre-mixing the appropriate amounts of hydrocarbonaceous material and olefins.

In some embodiments, for example when solid hydrocarbonaceous materials are used, moisture 12 may optionally be removed from the feed composition prior to being fed to the reactor, e.g., by an optional dryer 14. Removal of moisture from the feed stream may be advantageous for several reasons. For example, the moisture in the feed stream may require additional energy input in order to heat the feed to a temperature sufficiently high to achieve pyrolysis. Variations in the moisture content of the feed may lead to difficulties in controlling the temperature of the reactor. In addition, removal of moisture from the feed can reduce or eliminate the need to process the water during later processing steps.

In some embodiments, the feed composition may be dried until the feed composition comprises less than about 10%, less than about 5%, less than about 2%, or less than about 1% water by weight. Suitable equipment capable of removing water from the feed composition is known to those skilled in the art. As an example, in one set of embodiments, the dryer comprises an oven heated to a particular temperature (e.g., at least about 80° C., at least about 100° C., at least about 150° C., or higher) through which the feed composition is continuously, semi-continuously, or periodically passed. In some cases, the dryer may comprise a vacuum chamber into which the feed composition is processed as a batch. Other embodiments of the dryer may combine elevated temperatures with vacuum operation. The dryer may be integrally connected to the reactor or may be provided as a separate unit from the reactor.

In some instances, the particle size of the feed composition may be reduced in an optional grinding system 16 prior to passing the feed to the reactor. In some embodiments, the average diameter of the ground feed composition exiting the grinding system may comprise no more than about 50%, not more than about 25%, no more than about 10%, no more than about 5%, no more than about 2% of the average diameter of the feed composition fed to the grinding system. Large-particle feed material may be more easily transportable and less messy than small-particle feed material. On the other hand, in some cases it may be advantageous to feed small particles to the reactor (as discussed below). The use of a grinding system allows for the transport of large-particle feed between the source and the process, while enabling the feed of small particles to the reactor.

Suitable equipment capable of grinding the feed composition is known to those skilled in the art. For example, the grinding system may comprise an industrial mill (e.g., hammer mill, ball mill, etc.), a unit with blades (e.g., chipper, shredder, etc.), or any other suitable type of grinding system. In some embodiments, the grinding system may comprise a cooling system (e.g., an active cooling systems such as a pumped fluid heat exchanger, a passive cooling system such as one including fins, etc.), which may be used to maintain the feed composition at relatively low temperatures (e.g., ambient temperature) prior to introducing the feed composition to the reactor. The grinding system may be integrally connected to the reactor or may be provided as a separate unit from the reactor. While the grinding step is shown following the drying step in FIG. 1, the order of these operations may be reversed in some embodiments. In still other embodiments, the drying and grinding steps may be achieved using an integrated unit.

In some cases, grinding and cooling of the hydrocarbonaceous material may be achieved using separate units. Cooling of the hydrocarbonaceous material may be desirable, for example, to reduce or prevent unwanted decomposition of the feed material prior to passing it to the reactor. In one set of embodiments, the hydrocarbonaceous material may be passed to a grinding system to produce a ground hydrocarbonaceous material. The ground hydrocarbonaceous material may then be passed from the grinding system to a cooling system and cooled. The hydrocarbonaceous material may be cooled to a temperature of lower than about 300° C., lower than about 200° C., lower than about 100° C., lower than about 75° C., lower than about 50° C., lower than about 35° C., or lower than about 20° C. prior to introducing the hydrocarbonaceous material into the reactor. In embodiments that include the use of a cooling system, the cooling system includes an active cooling unit (e.g., a heat exchanger) capable of lowering the temperature of the biomass. In some embodiments, two or more of the drier, grinding system, and cooling system may be combined in a single unit. The cooling system may be, in some embodiments, directly integrated with one or more reactors.

As illustrated in FIG. 1, the feed composition may be transferred to reactor 20. The reactor may be used, in some instances, to perform catalytic pyrolysis of hydrocarbonaceous material. In the illustrative embodiment of FIG. 1, the reactor comprises any suitable reactor known to those skilled in the art. For example, in some instances, the reactor may comprise a continuously stirred tank reactor (CSTR), a batch reactor, a semi-batch reactor, or a fixed bed catalytic reactor, among others. In some cases, the reactor comprises a fluidized bed reactor, e.g., a circulating fluidized bed reactor. Fluidized bed reactors may, in some cases, provide improved mixing of the catalyst and/or hydrocarbonaceous material during pyrolysis and/or subsequent reactions, which may lead to enhanced control over the reaction products formed. The use of fluidized bed reactors may also lead to improved heat transfer within the reactor. In addition, improved mixing in a fluidized bed reactor may lead to a reduction of the amount of coke adhered to the catalyst, resulting in reduced deactivation of the catalyst in some cases.

As used herein, the term "fluidized bed reactor" is given its conventional meaning in the art and is used to refer to reactors comprising a vessel that can contain a granular solid material (e.g., silica particles, catalyst particles, etc.), in which a fluid (e.g., a gas or a liquid) is passed through the granular solid material at velocities sufficiently high as to suspend the solid material and cause it to behave as though it were a fluid. Examples of fluidized bed reactors are described in *Kirk-Othmer Encyclopedia of Chemical Technology* (online), Vol. 11, Hoboken, N.J.: Wiley-Interscience, c 2001-, pages 791-825, incorporated herein by reference. The term "circulating fluidized bed reactor" is also given its conventional meaning in the art and is used to refer to fluidized bed reactors in which the granular solid material is passed out of the reactor, circulated through a line in fluid communication with the reactor, and recycled back into the reactor. Examples of circulating fluidized bed reactors are described in *Kirk-Othmer Encyclopedia of Chemical Technology* (Online), Vol. 11, Hoboken, N.J.: Wiley-Interscience, c 2001-, pages 791-825.

Bubbling fluidized bed reactors and turbulent fluidized bed reactors are also known to those skilled in the art. In bubbling fluidized bed reactors, the fluid stream used to fluidize the granular solid material is operated at a sufficiently low flow rate such that bubbles and voids are observed within the volume of the fluidized bed during operation. In turbulent fluidized bed reactors, the flow rate of the fluidizing stream is higher than that employed in a bubbling fluidized bed reactor, and hence, bubbles and voids are not observed within the volume of the fluidized bed during operation. Examples of bubbling and turbulent fluidized bed reactors are described in *Kirk-Othmer Encyclopedia of Chemical Technology* (online), Vol. 11, Hoboken, N.J.: Wiley-Interscience, c 2001-, pages 791-825, incorporated herein by reference.

The reactor(s) may have any suitable size for performing the processes described herein. For example, the reactor may have a volume between 0.1-1 L, 1-50 L, 50-100 L, 100-250 L, 250-500 L, 500-1000 L, 1000-5000 L, 5000-10,000 L, or 10,000-50,000 L. In some instances, the reactor has a volume greater than about 1 L, or in other instances, greater than about 10 L, 50 L, 100 L, 250 L, 500 L, 1,000 L, or 10,000 L. Reactor volumes greater than 50,000 L are also possible. The reactor may be cylindrical, spherical, or any other suitable shape.

The inventors have discovered that higher yields of desired product production, lower yields of coke formation, and/or more controlled product formation (e.g., higher production of aromatics and/or olefins relative to other products) can be achieved when particular combinations of reactions conditions and system components are implemented in methods and systems described herein. For example, reaction conditions such as temperature of the reactor and/or solids separator, reactor pressure, heating rate of the feed stream, catalyst to hydrocarbonaceous material mass ratio, hydrocarbonaceous material to olefin (e.g., via a recycle stream) feed ratio, mass-normalized space velocities, residence time of the hydrocarbonaceous material in the reactor, residence time of the reaction products in the solids separator, and/or catalyst type (as well as silica to alumina molar ratio for zeolite catalysts) can be controlled to achieve beneficial results, as described below.

In some embodiments, olefins can be fed (e.g., via a recycle stream), in addition to hydrocarbonaceous material, to a vessel in which the hydrocarbonaceous material is to be reacted (e.g., via catalytic pyrolysis). In some cases, co-feeding olefins with the hydrocarbonaceous material can lead to an increase in the amount of aromatic compounds produced the reaction of the hydrocarbonaceous material. In some embodiments, co-feeding olefins to the reactor can result in an increase in aromatic compounds in the reaction product of at least about 5%, at least about 10%, or at least about 20%, relative to an amount of aromatic compounds that would be produced in the absence of the olefin co-feed. Olefins may be reacted with hydrocarbonaceous material in any suitable ratio. In some embodiments, the ratio of the mass of carbon within the hydrocarbonaceous material to the mass of carbon in the olefins in a mixture of hydrocarbonaceous material and olefins that is to be reacted is between about 2:1 and about 20:1, between about 3:1 and about 10:1, or between about 4:1 and about 5:1.

Figure 10:
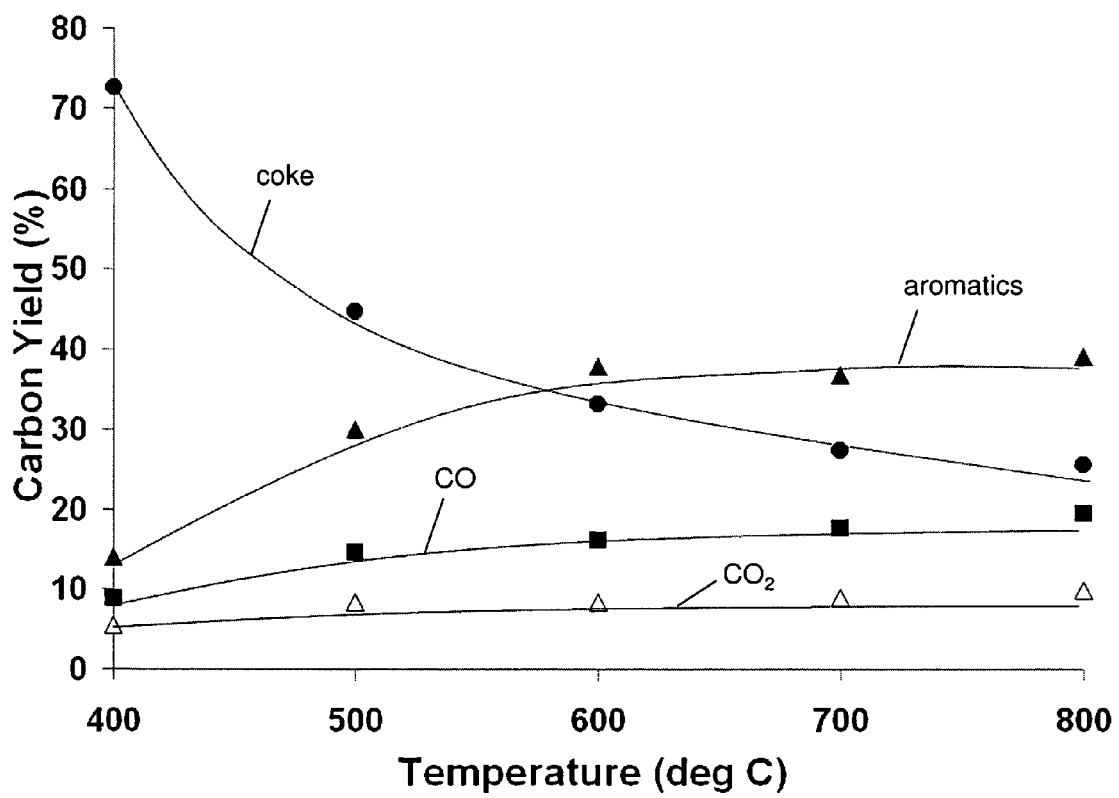
FIG. 10 is a plot of carbon yield of CO (■), aromatics (▲), $CO_2$ (Δ), and coke (•) as a function of reactor temperature for a catalytic pyrolysis of glucose with ZSM5, according to one set of embodiments.

The reactor(s) may be operated at any suitable temperature. In some instances, it may be desirable to operate the reactor at relatively high temperatures. For example, the reactor may be operated at temperatures of at least about 300° C., at least about 400° C., at least about 500° C., at least about 600° C., at least about 700° C., at least about 800° C., at least about 900° C., or at least about 1000° C. In some embodiments, the reactor may be operated at temperatures between about 500° C. and about 1000° C., between about 525° C. and about 800° C., between about 550° C. and about 700° C., or between about 575° C. and about 650° C. In other embodiments, the reactor may be operated between about 500° C. and about 600° C. Not wishing to be bound by any theory, relatively high operating temperatures may affect the kinetics of the reactions in such a way that desired reaction products are formed and/or undesired product formation is inhibited or reduced. FIG. 10 includes a plot of the carbon yield of various products as a function of reactor temperature for the catalytic pyrolysis of glucose with ZSM-5 catalyst in one particular embodiment. Note that in the exemplary embodiment of FIG. 10, the yield of aromatics (indicated by the solid triangles) increases with an increase in temperature from 400° C. to 800° C. In addition, the relative amount of coke produced decreases as the temperature is increased from 400° C. to 800° C. In other embodiments, however, lower temperatures can be used.

The reactor(s) may also be operated at any suitable pressure. In some embodiments, the reactor may be operated at pressures of between about 1-4 atm. In some embodiments, the reactor may be operated at a pressure of at least about 1 atm, at least about 2 atm, at least about 3 atm, or at least about 4 atm.

The inventors have discovered that in certain embodiments, it is advantageous to heat the feed stream (e.g., a gaseous hydrocarbonaceous material, a solid hydrocarbonaceous material, a mixture of a solid hydrocarbonaceous material and any supplemental olefins and/or a solid catalyst, etc.) at a relatively fast rate as it enters the reactor. High heating rates may be advantageous for a number of reasons. For instance, high heating rates may enhance the rate of mass transfer of the reactants from the bulk solid biomass to the catalytic reactant sites. This may, for example, facilitate introduction of volatile organic compounds formed during the pyrolysis of the hydrocarbonaceous material into the catalyst before completely thermally decomposing the hydrocarbonaceous material into generally undesired products (e.g., coke). In addition, high heating rates may reduce the amount of time the reactants are exposed to intermediate temperatures (i.e., temperatures between the temperature of the feed and the desired reaction temperature). Prolonged exposure of the reactants to intermediate temperatures may lead to the formation of undesirable products via undesirable decomposition and/or reaction pathways. Examples of suitable heating rates for heating the feed stream upon entering the reactor the feed stream include, for example, greater than about 50° C./s, greater than about 100° C./s, greater than about 200° C./s, greater than about 300° C./s, greater than about 400° C./s, greater than about 500° C./s, greater than about 600° C./s, greater than about 700° C./s, greater than about 800° C./s, greater than about 900° C./s, greater than about 1000° C./s, or greater. In some cases, the feed stream may be heated at a heating rate of between about 500° C./s and about 1000° C./s. In some embodiments, the heating rate for heating the feed stream upon entering the reactor may be between about 50° C./s and about 1000° C./s, or between about 50° C./s and about 400° C./s.

In some embodiments, the mass-normalized space velocity of the hydrocarbonaceous material may be selected to selectively produce a desired array of fluid hydrocarbon products. As used herein, the term "mass-normalized space velocity" is defined as the mass flow rate of the hydrocarbonaceous material into the reactor (e.g., as measured in g/hr) divided by the mass of catalyst in the reactor (e.g., as measured in g) and has units of inverse time. The mass-normalized space velocity of the hydrocarbonaceous material in a reactor may be calculated using different methods depending upon the type of reactor being used. For example, systems employing batch or semi-batch reactors, the hydrocarbonaceous material does not have a mass-normalized space velocity. For systems in which catalyst is fed to and/or extracted from the reactor during reaction (e.g., circulating fluidized bed reactors), the mass-normalized space velocity may be determined by calculating the average amount of catalyst within the volume of the reactor over a period of operation (e.g., steady-state operation).

Any suitable mass-normalized space velocity may be used in the embodiments described herein. In some instances, a mass-normalized space velocity of less than about 10 hour$^{-1}$, less than about 5 hour$^{-1}$, less than about 1 hour$^{-1}$, less than about 0.5 hour$^{-1}$, less than about 0.1 hour$^{-1}$, less than about 0.05 hour$^{-1}$, or less than about 0.01 hour$^{-1}$ may be employed. In some embodiments, a mass-normalized space velocity of between about 0.01 hour$^{-1}$ and about 10 hour$^{-1}$, between about 0.01 hour$^{-1}$ and about 5 hour$^{-1}$, between about 0.01 hour$^{-1}$ and about 0.1 hour$^{-1}$, between about 0.1 hour$^{-1}$ and about 1 hour$^{-1}$, or between about 1 hour$^{-1}$ and about 10 hour$^{-1}$ may be employed. It may also be advantageous, in some embodiments, to employ mass-normalized space velocities of less than about 1 hour$^{-1}$, less than about 0.5 hour$^{-1}$, less than about 0.1 hour$^{-1}$, less than about 0.05 hour$^{-1}$, less than about 0.01 hour$^{-1}$, between about 0.01 hour$^{-1}$ and 0.1 hour$^{-1}$, or between about 0.1 hour$^{-1}$ and 1 hour$^{-1}$ using a fluidized bed reactor.

Some embodiments comprise varying the mass-normalized space velocity of the hydrocarbonaceous material to selectively produce different fluid hydrocarbon products. For example, in some embodiments, varying the mass-normalized space velocity of the hydrocarbonaceous material may control the relative amounts of aromatic and olefin compounds in the reaction product. For example, relatively low mass-normalized space velocities may be used to produce a relatively larger amount of aromatics than olefins. Relatively high mass-normalized space velocities may be used to produce a relatively larger amount of olefins than aromatics. In some embodiments, solid hydrocarbonaceous material is provided in a fluidized bed reactor at a mass-normalized space velocity of between about 0.1 hour$^{-1}$ and about 10 hour$^{-1}$ to selectively produce olefin compounds, or between about 0.01 hour$^{-1}$ and 0.1 hour$^{-1}$ to selectively produce aromatic compounds.

In some instances, it is beneficial to control the residence time of the hydrocarbonaceous material (e.g., a solid hydrocarbonaceous material) in the reactor and/or under a defined set of reaction conditions (i.e. conditions under which the hydrocarbonaceous material can undergo pyrolysis in a given reactor system). In continuous flow systems, the residence time of the hydrocarbonaceous material in the reactor is defined as the amount of time the hydrocarbonaceous material and any reaction products formed therefrom (excluding products that accumulate in the reactor such as, for example, coke deposited on the catalyst) spend in the reactor. The residence time of the hydrocarbonaceous material in a reactor may be calculated using different methods depending upon the type of reactor being used. For example, in embodiments in which the reactor comprises a packed bed reactor into which only hydrocarbonaceous material is continuously fed (i.e. no carrier or fluidizing flow is utilized), the residence time of the hydrocarbonaceous material in the reactor as used herein can be determined by the volume of the reactor divided by the volumetric flow rate of the product gases exiting the reactor. In cases where the reaction takes place in a reactor that is closed to the flow of mass during operation (e.g., a batch reactor), the residence time of the hydrocarbonaceous material in such a reactor is defined as the amount of time elapsing between the time at which the temperature in the reactor containing the hydrocarbonaceous material reaches a level sufficient to commence a pyrolysis reaction (e.g. typically about 300° C. to about 1000° C. for many typical hydrocarbonaceous feed stock materials) and the time at which the reactor is quenched (e.g., cooled to a temperature below that sufficient to support further pyrolysis—e.g. typically about 300° C. to about 1000° C. for many typical hydrocarbonaceous feed stock materials).

In some cases, e.g. for certain fluidized bed reactors, the reactor feed stream(s) may include feed stream(s) comprising auxiliary materials (i.e., matter other than hydrocarbonaceous materials and/or olefins). For example, in certain cases where fluidized beds are used as reactors, the feed stream may comprise fluidization fluid(s). In cases where circulating fluidized beds are used, catalyst and fluidization fluid may both be fed/recycled to the reactor. In some cases, the auxiliary materials may comprise contaminants entrained in the hydrocarbonaceous material. In such cases, the residence time of the hydrocarbonaceous material in the reactor can be determined as the volume of the reactor divided by the volumetric flow rate of the hydrocarbonaceous material and reaction product gases exiting the reactor as with the packed bed situation described above; however, since the flow rate of the hydrocarbonaceous material and reaction product gases exiting the reactor may not be convenient to determine directly, the volumetric flow rate of the hydrocarbonaceous material and reaction product gases exiting the reactor may be estimated by subtracting the feed volumetric flow rate of the auxiliary materials (e.g., fluidization fluid, catalyst, contaminants, etc.) into the reactor from the total volumetric flow rate of the gas stream(s) exiting the reactor.

In some embodiments, the residence time of a material (e.g., a hydrocarbonaceous material or any other suitable feed material) in the reactor is at least about 2 seconds, at least about 5 seconds, at least about 10 seconds, at least about 30 seconds, at least about 60 seconds, at least about 120 seconds, at least about 240 seconds, or at least about 480 seconds. In some cases, the residence time of a material (e.g., a hydrocarbonaceous material or any other suitable feed material) in the reactor is less than about 5 minutes, between about 1 minute and about 4 minutes, or from about 2 seconds to about 480 seconds. Previous "fast pyrolysis" studies have, in many cases, employed systems with very short feed material (e.g., hydrocarbonaceous material) residence times (e.g., less than 2 seconds). The inventors have discovered, however, that in some cases, the use of relatively longer residence times allows adequate time for additional chemical reactions to form desirable products. Long residence times can be achieved by, for example, increasing the volume of the reactor and/or reducing the volumetric flow rate of the hydrocarbonaceous materials. It should be understood, however, that in some embodiments described herein, the residence time of the feed material (e.g., hydrocarbonaceous material) may be relatively shorter, e.g., less than about 2 seconds or less than about 1 second.

In certain cases where fluidized bed reactors are used, the feed material (e.g., a solid hydrocarbonaceous material) in the reactor may be fluidized by flowing a fluid stream through the reactor. In the exemplary embodiment of FIG. 1, a fluid stream 44 is used to fluidize the feed material in reactor 20. Fluid may be supplied to the fluid stream from a fluid source 24 and/or from the product streams of the reactor via a compressor 26 (which will be described in more detail below). As used herein, the term "fluid" means a material generally in a liquid, supercritical, or gaseous state. Fluids, however, may also contain solids such as, for example, suspended or colloidal particles. In some embodiments, it may be advantageous to control the residence time of the fluidization fluid in the reactor. The residence time of the fluidization fluid is defined as the volume of the reactor divided by the volumetric flow rate of the fluidization fluid. In some cases, the residence time of the fluidization fluid may be at least about 5 seconds, at least about 10 seconds, at least about 30 seconds, at least about 60 seconds, at least about 120 seconds, at least about 240 seconds, or at least about 480 seconds. In some cases, the residence time of the fluidization fluid may be from about 2 seconds to about 480 seconds, from about 5 seconds to about 480 seconds, from about 10 seconds to about 480 seconds, from about 30 seconds to about 480 seconds, from about 60 seconds to about 480 seconds, from about 120 seconds to about 480 seconds, or from about 240 seconds to about 480 seconds.

Suitable fluidization fluids that may be used in this invention include, for example, inert gases (e.g., helium, argon, neon, etc.), hydrogen, nitrogen, carbon monoxide, and carbon dioxide, among others.

As shown in the illustrative embodiment of FIG. 1, the products (e.g., fluid hydrocarbon products) formed during the reaction of the hydrocarbonaceous material exit the reactor via a product stream 30. In addition to the reaction products, the product stream may, in some cases, comprise unreacted hydrocarbonaceous material, fluidization fluid, and/or catalyst. In one set of embodiments, the desired reaction product(s) (e.g., liquid aromatic hydrocarbons, olefin hydrocarbons, gaseous products, etc.) may be recovered from an effluent stream of the reactor.

In some embodiments, at least a portion of the olefins in the fluid hydrocarbon product stream 30 is separated from the rest of the product stream to produce a recycle stream 100, comprising at least a portion of the separated olefins, and product stream 31A. The separation of olefins from fluid hydrocarbon products can be accomplished by an olefin recycler 102. While the olefin recycler is shown as being positioned directly downstream of reactor 20 in FIG. 1, it should be understood that the olefin recycler can be positioned at any point downstream of the reactor, and the separation of olefins from other fluid hydrocarbon products can potentially be performed at any of a variety of points after the fluid hydrocarbon products are produced. In addition, while recycle stream 100 is illustrated in FIG. 1 as being combined with feed stream 10 upstream of dryer 14, it should be understood that recycle stream 100 could alternatively be combined with feed stream 10 downstream of dryer 14 and/or grinder 16, fed directly to reactor 20, and/or combined with any of the catalyst streams (e.g., 34, 42, 44, 46, and/or 47) described in more detail below.

Suitable methods for separating olefins from other fluid hydrocarbon products are known to those of ordinary skill in the art. For example, olefins can be separated from other fluid hydrocarbon products by cooling product stream 30 to a temperature that lies between the boiling points of the olefins and the other fluid hydrocarbon products. Optionally, olefin recycler 102 can comprise a multi-stage separator. For example, the olefin recycler can comprise a first separator that directly separates the gaseous products (including olefins) from liquid products (e.g., high boiling point aromatics such as benzene, toluene, xylene, etc.), and a second separator that separates at least a portion of the olefins from other gaseous products (e.g., gaseous aromatics, $CO_2$, CO, etc.). The methods and/or conditions used to perform the separation can depend upon the relative amounts and types of compounds present in the fluid hydrocarbon product stream, and one of ordinary skill in the art will be capable of selecting a method and the conditions suitable to achieve a given separation given the guidance provided herein.

In some embodiments, optional product reactor 104 can be incorporated into the process. The product reactor can be used, for example, to convert one or more of the fluid hydrocarbon products (e.g., olefins, aromatics, etc.) in product stream 31A to one or more other products (output as stream 31B in FIG. 1). In some cases, the product reactor may contain a catalyst (e.g., a zeolite catalyst) which can be used to perform one or more catalytic reactions. For example, in some embodiments, the product reactor can be used to oligomerize (e.g., via use of a catalyst) one or more olefin products to produce one or more aromatic products. As another example, the product reactor can be used to perform a carbonylation reaction involving aromatic compounds (e.g., carbonylation of ethylene to acrylene via the addition of carbon monoxide and water). One of ordinary skill in the art is capable of selecting appropriate reactor types and/or conditions for performing such reactions. While optional product reactor 104 is shown located directly downstream of the olefin recycler 102 in FIG. 1, it should be understood that the olefin recycler can be positioned at any point downstream of the reactor (e.g., reactor 20 in FIG. 1), and the reaction of olefins, aromatics, or other fluid hydrocarbon products can potentially be performed at any of a variety of points after the fluid hydrocarbon products are produced.

As shown in the illustrative embodiment of FIG. 1, product stream 31B (or 31A) may be fed to an optional solids separator 32. The solids separator may be used, in some cases, to separate the reaction products from catalyst (e.g., at least partially deactivated catalyst) present in the product stream. In addition, the solids separator may be used, in some instances, to remove coke and/or ash from the catalyst. In some embodiments, the solids separator may comprise optional purge stream 33, which may be used to purge coke, ash, and/or catalyst from the solids separator.

The equipment required to achieve the solids separation and/or decoking steps can be readily designed by one of ordinary skill in the art. For example, in one set of the embodiments, the solids separator may comprise a vessel comprising a mesh material that defines a retaining portion and a permeate portion of the vessel. The mesh may serve to retain the catalyst within the retaining portion while allowing the reaction product to pass to the permeate portion. The catalyst may exit the solids separator through a port on the retaining side of the mesh while the reaction product may exit a port on the permeate side of the mesh. Other examples of solids separators and/or decokers are described in more detail in *Kirk-Othmer Encyclopedia of Chemical Technology* (Online), Vol. 11, Hoboken, N.J.: Wiley-Interscience, c2001-, pages 700-734; and C. D. Cooper and F. C. Alley. *Air Pollution Control, A Design Approach*. Second Ed. Prospect Heights, Ill.: Waveland Press, Inc. c1994, pages 127-149, incorporated herein by reference.

The solids separator may be operated at any suitable temperature. In some embodiments, the solids separator may be operated at elevated temperatures. The inventors have discovered that for certain reactions, the use of elevated temperatures in the solids separator can allow for additional reforming and/or reaction of the compounds from the reactor. This may allow for the increased formation of desirable products. Not wishing to be bound by any theory, elevated temperatures in the solids separator may provide enough energy to drive endothermic reforming reactions. The solids separator may be operated at a temperature of, for example, between about 25° C. and about 200° C., between about 200° C. and about 500° C., between about 500° C. and about 600° C., or between about 600° C. and about 800° C. In some cases, the solids separator may be operated at temperatures of at least about 500° C., at least about 600° C., at least 700° C., at least 800° C., or higher.

In some cases, it may be beneficial to control the residence time of the catalyst in the solids separator. The residence time of the catalyst in the solids separator is defined as the volume of the solids separator divided by the volumetric flow rate of the catalyst through the solids separator. In some cases, relatively long residence times of the catalyst in the solids separator may be desired in order to facilitate the removal of sufficient amounts of ash, coke, and/or other undesirable products from the catalyst. In addition, the inventors have discovered that by employing relatively long residence times of the catalyst in the solids separator, the pyrolysis products may be further reacted to produce desirable products. In some embodiments, the residence time and temperature in the solids separator are together selected such that a desired product stream is produced. In some embodiments, the residence time of the catalyst in the solids separator is at least about 1 second, at least about 5 seconds, at least about 10 seconds, at least about 30 seconds, at least about 60 seconds, at least about 120 seconds, at least about 240 seconds, at least about 300 seconds, at least about 600 seconds, or at least about 1200 seconds. Methods for controlling the residence time of the catalyst in the solids separator are known by those skilled in the art. For example, in some cases, the interior wall of the solids separator may comprise baffles that serve to restrict the flow of catalyst through the solids separator and/or increase the path length of fluid flow in the solids separator. Additionally or alternatively, the residence time of the catalyst in the solids separator may be controlled by controlling the flow rate of the catalyst through the solids separator (e.g., by controlling the flow rate of the fluidizing fluid through the reactor).

The solids separator may have any suitable size. For example, the solids separator may have a volume between 0.1-1 L, 1-50 L, 50-100 L, 100-250 L, 250-500 L, 500-1000 L, 1000-5000 L, 5000-10,000 L, or 10,000-50,000 L. In some instances, the solids separator has a volume greater than about 1 L, or in other instances, greater than about 10 L, 50 L, 100 L, 250 L, 500 L, 1,000 L, or 10,000 L. Solids separator volumes greater than 50,000 L are also possible. The solids separator may be cylindrical, spherical, or any other shape and may be circulating or non-circulating. In some embodiments, the solids separator may comprise a vessel or other unit operation similar to that used for one or more of the reactor(s) used in the process. The flow of the catalyst in the solids separator may comprise any suitable geometry. For example, the flow path may be substantially straight. In some cases, the solids separator may comprise a flow channel with a serpentine, meandering, helical, or any other suitable shape. The ratio of the length of the flow path of the solids separator (or, in certain embodiments, the path length of the catalyst through the solids separator) to the average diameter of the solids separator channel may comprise any suitable ratio. In some cases, the ratio may be at least 2:1, at least 5:1, at least 10:1, at least 50:1, at least 100:1, or greater.

The parameters outlined above may be used in any suitable combination to produce desirable reaction products (e.g., aromatic and/or olefin compounds) and/or favorable yields or particular components. For example, the use of long residence times may be combined with the use of a circulating or turbulent fluidized bed reactor to process solid hydrocarbonaceous material. In some embodiments, relatively high temperatures (e.g., at least 500° C.) and long residence times (e.g., at least about 1 second, at least about 5 seconds, at least about 10 seconds, at least about 30 seconds, at least about 60 seconds, at least about 120 seconds, at least about 240 seconds, at least about 300 seconds, at least about 600 seconds, or at least about 1200 seconds, etc.) may be used in the solids separator after pyrolyzing a solid hydrocarbonaceous material in the reactor. In other embodiments, relatively low mass-normalized space velocities (e.g., less than about 0.1 hour$^{-1}$, less than about 0.05 hour$^{-1}$, less than about 0.01 hour$^{-1}$, etc.) may be used to produce a relatively larger amount of aromatics than olefins in a fluidized bed reactor, e.g., at least about 6% aromatics or more. Relatively high mass-normalized space velocities (e.g., at least about 0.1 hour$^{-1}$, at least about 0.5 hour$^{-1}$) may be used to produce a relatively larger amount of olefins than aromatics in a fluidized bed reactor, e.g., at least about 3 wt %, at least about 6 wt %, at least about 10 wt %, at least about 15 wt %, or at least about 20 wt % olefins). In another set of embodiments, a solid hydrocarbonaceous material and a zeolite catalyst comprising a large silica to alumina molar ratio (e.g., at least about 30) may be heated in a reactor at a high rate (e.g., greater than about 500° C./s). In some cases, a catalyst and a solid hydrocarbonaceous material may be fed to a reactor in a mass ratio of at least about 0.5:1 and heated to a temperature of, for example, between 500° C. and 1000° C. In some instances, a catalyst and a solid hydrocarbonaceous material may be fed to a reactor in a mass ratio of at least about 0.5:1 such that the mixture has a relatively long residence time (e.g., at least about 5 seconds). In yet another set of embodiments, a relatively high fluidization fluid residence time (e.g., at least about 5 seconds) and a relatively high reactor temperature (e.g., between about 500° C. and about 1000° C.) may be used.

As previously mentioned, the solids separator may not be required in all embodiments. For example, for situations in which catalytic fixed bed reactors are employed, the catalyst may be retained within the reactor, and the reaction products may exit the reactor substantially free of catalyst, thus negating the need for a separate separation step.

In the set of embodiments illustrated in FIG. 1, separated catalyst may exit the solids separator via stream 34. In some cases, the catalyst exiting the separator may be at least partially deactivated. The separated catalyst may be fed, in some embodiments, to a regenerator 36 in which any catalyst that was at least partially deactivated may be re-activated. In some embodiments, the regenerator may comprise optional purge stream 37, which may be used to purge coke, ash, and/or catalyst from the regenerator. Methods for activating catalyst are well-known to those skilled in the art, for example, as described in *Kirk-Othmer Encyclopedia of Chemical Technology* (Online), Vol. 5, Hoboken, N.J.: Wiley-Interscience, c 2001-, pages 255-322, incorporated herein by reference.

In one set of embodiments, an oxidizing agent is fed to the regenerator via a stream 38, e.g., as shown in FIG. 1. The oxidizing agent may originate from any source including, for example, a tank of oxygen, atmospheric air, steam, among others. In the regenerator, the catalyst is re-activated by reacting the catalyst with the oxidizing agent. In some cases, the deactivated catalyst may comprise residual carbon and/or coke, which may be removed via reaction with the oxidizing agent in the regenerator. The regenerator in FIG. 1 comprises a vent stream 40 which may include regeneration reaction products, residual oxidizing agent, etc.

The regenerator may be of any suitable size mentioned above in connection with the reactor or the solids separator. In addition, the regenerator may be operated at elevated temperatures in some cases (e.g., at least about 300° C., 400° C., 500° C., 600° C., 700° C., 800° C., or higher). The residence time of the catalyst in the regenerator may also be controlled using methods known by those skilled in the art, including those outlined above. In some instances, the mass flow rate of the catalyst through the regenerator will be coupled to the flow rate(s) in the reactor and/or solids separator in order to preserve the mass balance in the system.

As shown in the illustrative embodiment of FIG. 1, the regenerated catalyst may exit the regenerator via stream 42. The regenerated catalyst may be recycled back to the reactor via recycle stream 47. In some cases, catalyst may be lost from the system during operation. In some such and other cases, additional "makeup" catalyst may be added to the system via a makeup stream 46. As shown illustratively in FIG. 1, the regenerated and makeup catalyst may be fed to the reactor with the fluidization fluid via recycle stream 47, although in other embodiments, the catalyst and fluidization fluid may be fed to the reactor via separate streams.

Referring back to solids separator 32 in FIG. 1, the reaction products (e.g., fluid hydrocarbon products) exit the solids separator via stream 48. In some cases, a fraction of stream 48 may be purged via purge stream 60. The contents of the purge stream may be fed to a combustor or a water-gas shift reactor, for example, to recuperate energy that would otherwise be lost from the system. In some cases, the reaction products in stream 48 may be fed to an optional condenser 50. The condenser may comprise a heat exchanger which condenses at least a portion of the reaction product from a gaseous to a liquid state. The condenser may be used to separate the reaction products into gaseous, liquid, and solid fractions. The operation of condensers is well known to those skilled in the art. Examples of condensers are described in more detail in *Perry's Chemical Engineers' Handbook*, Section 11: "Heat Transfer Equipment." 8th ed. New York: McGraw-Hill, c 2008, incorporated herein by reference.

The condenser may also, in some embodiments, make use of pressure change to condense portions of the product stream. In FIG. 1, stream 54 may comprise the liquid fraction of the reaction products (e.g., water, aromatic compounds, olefin compounds, etc.), and stream 74 may comprise the gaseous fraction of the reaction products (e.g., CO, $CO_2$, $H_2$, etc.). In some embodiments, the gaseous fraction may be fed to a vapor recovery system 70. The vapor recovery system may be used, for example, to recover any desirable vapors within stream 74 and transport them via stream 72. In addition, stream 76 may be used to transport CO, $CO_2$, and/or other non-recoverable gases from the vapor recovery system. It should be noted that, in some embodiments, the optional vapor recovery system may be placed in other locations. For example, in some embodiments, a vapor recovery system may be positioned downstream of purge stream 54. One skilled in the art can select an appropriate placement for a vapor recovery system.

Other products (e.g., excess gas) may be transported to optional compressor 26 via stream 56, where they may be compressed and used as fluidization gas in the reactor (stream 22) and/or where they may assist in transporting the hydrocarbonaceous material to the reactor (streams 58). In some instances, the liquid fraction may be further processed, for example, to separate the water phase from the organic phase, to separate individual compounds, etc.

It should be understood that, while the set of embodiments described by FIG. 1 includes a reactor, solids separator, regenerator, condenser, etc., not all embodiments will involve the use of these elements. For example, in some embodiments, the feed stream may be fed to a catalytic fixed bed reactor, reacted, and the reaction products may be collected directly from the reactor and cooled without the use of a dedicated condenser. In some instances, while a dryer, grinding system, solids separator, regenerator, condenser, and/or compressor may be used as part of the process, one or more of these elements may comprise separate units not fluidically and/or integrally connected to the reactor. In other embodiments one or more of the dryer, grinding system, solids separator, regenerator, condenser, and/or compressor may be absent. In some embodiments, the desired reaction product(s) (e.g., liquid aromatic hydrocarbons, olefin hydrocarbons, gaseous products, etc.) may be recovered at any point in the production process (e.g., after passage through the reactor, after separation, after condensation, etc.).

In some embodiments, a process of the invention may involve the use of more than one reactor. For instance, multiple reactors may be connected in fluid communication with each other, for example, to operate in series and/or in parallel, as shown in the exemplary embodiment of FIG. 7. In some embodiments, the process may comprise providing a hydrocarbonaceous material in a first reactor and pyrolyzing, within the first reactor, at least a portion of the hydrocarbonaceous material under reaction conditions sufficient to produce one or more pyrolysis products. In some embodiments, a catalyst may be provided to the first reactor, and at least a portion of the one or more pyrolysis products in the first reactor are catalytically reacted using the catalyst under reaction conditions sufficient to produce one or more fluid hydrocarbon products. The process may further comprise catalytically reacting at least a portion of the one or more pyrolysis products in a second reactor using a catalyst under reaction conditions sufficient to produce one or more fluid hydrocarbon products. In some cases, after catalytically reacting at least a portion of the one or more pyrolysis products in the second reactor, the process may comprise a step of further reacting within the second reactor at least a portion of the one or more fluid hydrocarbon products from the first reactor to produce one or more other hydrocarbon products.

Figure 7:
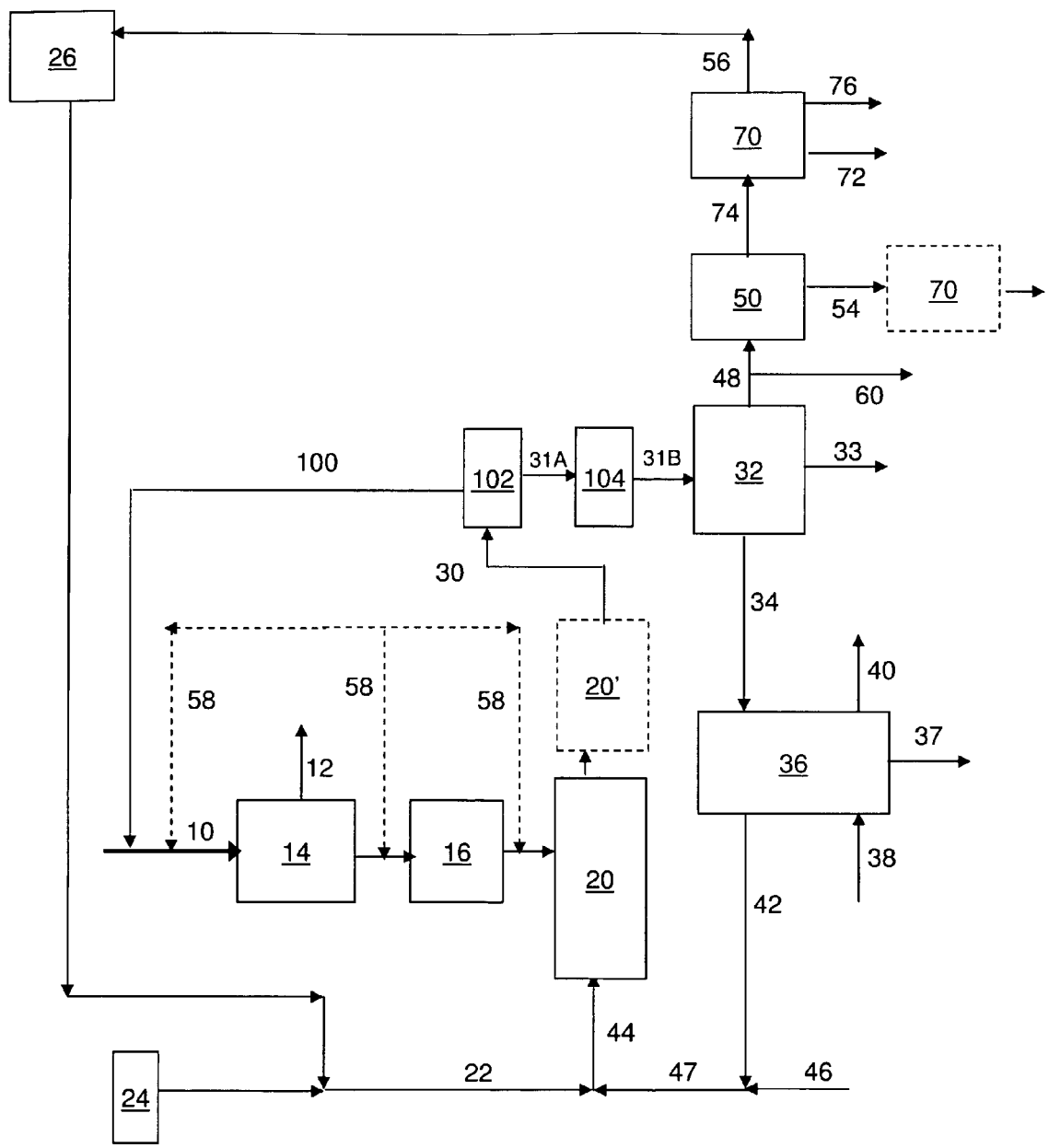
FIG. 7 is a schematic diagram of a two reactor catalytic pyrolysis process, according to one set of embodiments.

In FIG. 7, the reaction product from reactor 20 is transported to a second reactor 20'. Those skilled in the art are familiar with the use of multiple-reactor systems for the pyrolysis of organic material to produce organic products and such systems are known in the art. While FIG. 7 illustrates a set of embodiments in which the reactors are in fluid communication with each other, in some instances, the two reactors may not be in fluid communication. For example, a first reactor may be used to produce a first reaction product which may be transported to a separate facility for reaction in a second reactor. In some instances, a composition comprising hydrocarbonaceous material (with or without a catalyst) may be heated in a first reactor, and at least a portion of the hydrocarbonaceous material may be pyrolyzed to produce a pyrolysis product (and optionally at least partially deactivated catalyst). The first pyrolysis product may be in the form of a liquid and/or a gas. The composition comprising the first pyrolysis product may then be heated in a second reactor, which may or may not be in fluid communication with the first reactor. After the heating step in the second reactor, a second pyrolysis product from the second reactor may be collected. The second pyrolysis product may be in the form of a liquid and/or a gas. In some cases, the composition comprising hydrocarbonaceous material that is fed into the first reactor may comprise, for example, a mixture of a solid hydrocarbonaceous material and a solid catalyst. The first pyrolysis product produced from the first reactor may be different in chemical composition, amount, state (e.g., a fluid vs. a gas) than the second pyrolysis product. For example, the first pyrolysis product may substantially include a liquid, while the second pyrolysis product may substantially include a gas. In another example, the first pyrolysis product includes a fluid product (e.g., a bio-oil, sugar), and the second pyrolysis product comprises a relatively higher amount of aromatics than the first pyrolysis product. In some instances, the first pyrolysis product includes a fluid product (e.g., including aromatic compounds), and the second pyrolysis product comprises a relatively higher amount of olefins than the first pyrolysis product. In yet another example, the first pyrolysis product includes a fluid product (e.g., a bio-oil, sugar), and the second pyrolysis product comprises a relatively higher amount of oxygenated aromatic compounds than the first pyrolysis product.

One or more of the reactors in a multiple reactor configuration may comprise a fluidized bed reactor (e.g., a circulating fluidized bed reactor, a turbulent fluidized bed reactor, etc.) or, in other instances, any other type of reactor (e.g., any of the reactors mentioned above). For example, in one set of embodiments, the first reactor comprises a circulating fluidized bed reactor or a turbulent fluidized bed reactor, and the second reactor comprises a circulating fluidized bed reactor or a turbulent fluidized bed reactor in fluid communication with the first reactor. In addition, the multiple reactor configuration may include any of the additional processing steps and/or equipment mentioned herein (e.g., a solids separator, a regenerator, a condenser, etc.). The reactors and/or additional processing equipment may be operated using any of the processing parameters (e.g., temperatures, residence times, etc.) mentioned herein.

Figure 8A:
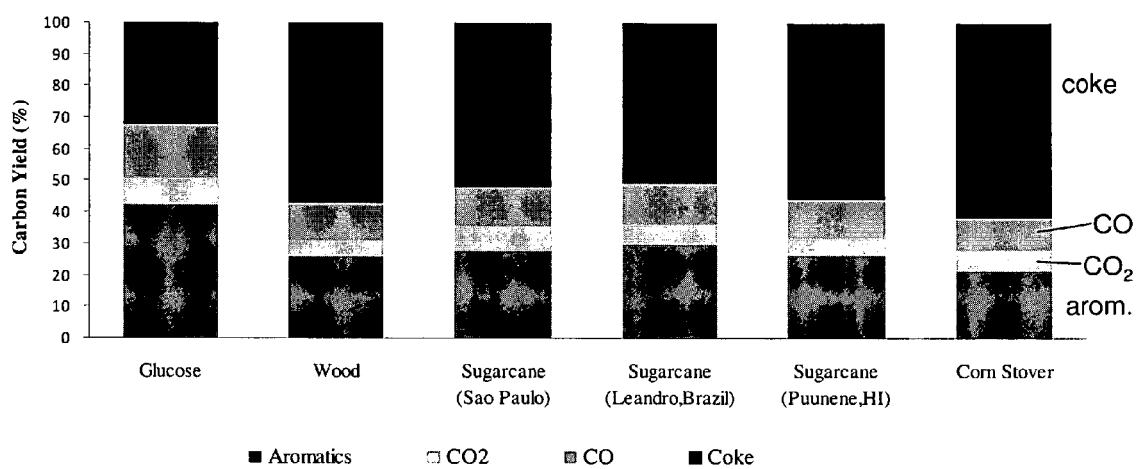
FIGS. 8A-8B are plots of (A) carbon yields for various hydrocarbonaceous feedstock material and (B) aromatic selectivity for feeds of benzene (Ben.), toluene (Tol.), ethyl-benzene and xylenes (E-Ben., Xyl.), methyl-ethyl-benzene and trimethyl-benzene (m,e-Ben., tmBen.), indanes (Ind.), and naphthalenes (Nap.) for various hydrocarbonaceous feedstock material, according to one set of embodiments.
Figure 8B:
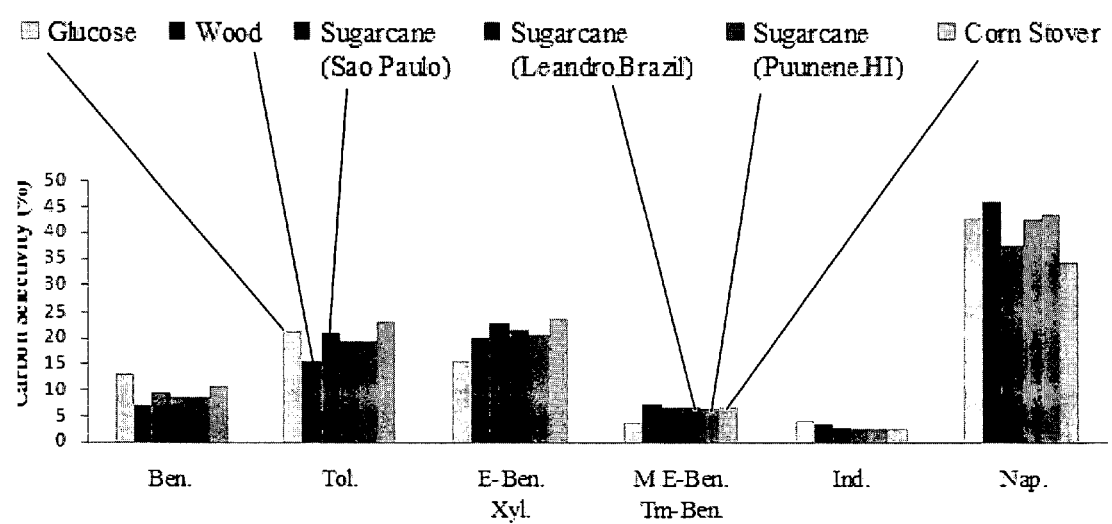

Hydrocarbonaceous material useful in the context of this invention may comprise, for example, a component such as xylitol, glucose (e.g., α-D-glucose, β-D-glucose), cellobiose, cellulose, hemi-cellulose, lignin, sugar cane bagasse, glucose, wood, and corn stover together with pyrolysis products thereof and combinations of such components and/or their pyrolysis products. Other examples of hydrocarbonaceous materials include, for example, plastic waste, recycled plastics, agricultural and municipal solid waste, food waste, animal waste, carbohydrates, lignocellulosic materials (e.g., wood chips or shavings, lignocellulosic biomass, etc.), or combinations thereof, among others. FIGS. 8A and 8B include plots of product distribution for various hydrocarbonaceous feeds including sugar cane bagasse, glucose, wood, and corn stover. In the embodiments illustrated in FIG. 8A, all of the feedstocks tested produced relatively high aromatic yields (e.g., greater than 20% carbon yields (equivalent to weight yields greater than approximately 8%)). Carbon yields greater than 40% (equivalent to weight yields greater than approximately 18.5%) were produced using a glucose feed in this set of embodiments. FIG. 8B includes a plot of aromatic selectivity for various hydrocarbonaceous feedstock materials. The aromatic species included in FIG. 8B are benzene, toluene, ethyl-benzene and xylenes, methyl-ethyl-benzene and trimethyl-benzene, indanes, and naphthalenes.

As demonstrated herein, choice of hydrocarbonaceous and catalyst materials can be used to vary the composition of the resulting fluid hydrocarbon product. For instance, a wide range of hydrocarbonaceous materials (e.g., without limitation, glucose, cellulose, cellobiose, xylitol, etc.) can be used for production of naphthalenes. In another example, certain hydrocarbonaceous materials (e.g., cellulose) can be used for selective production of toluene. Alternatively, without limitation, where a hydrocarbonaceous material comprises glucose, adjusting a catalyst to glucose mass ratio of the feed composition can be used to vary production of identifiable, oxygenated compounds (e.g., oxygenated aromatic compounds). The catalyst to glucose mass ratio in the feed composition may be adjusted by increasing or decreasing the amount of catalyst fed to the reactor relative to the amount of glucose fed to the reactor. Some such and other compounds may be isolated as specialty chemicals for further reaction or incorporated into subsequent biofuel processing. In certain other embodiments, a hydrocarbonaceous material can comprise a lignin pyrolysis product such as, for example, benzyl phenyl ether. Pyrolysis of this and other compounds can be used to produce a range of aromatic compounds for use as fuel additives or commodity chemicals. Regardless of initial hydrocarbonaceous materials or resulting pyrolysis products, processes described herein can optionally include hydrogenation of various unsaturated or aromatic compounds to produce hydrogenation products that can be used as biofuels, or incorporated into biofuel production.

As described above, the hydrocarbonaceous material in the feed composition may comprise a solid, liquid, and/or gas. In cases where the hydrocarbonaceous material includes solids, the solids may be of any suitable size. In some cases, it may be advantageous to use hydrocarbonaceous solids with relatively small particle sizes. Small-particle solids may, in some instances, react more quickly than larger solids due to their relatively higher surface area to volume ratios compared to larger solids. In addition, small particle sizes may allow for more efficient heat transfer within each particle and/or within the reactor volume. This may prevent or reduce the formation of undesired reaction products. Moreover, small particle sizes may provide for increased solid-gas and solid-solid contact, leading to improved heat and mass transfer. In some embodiments, the average size of the solid hydrocarbonaceous material is less than about 5 mm, less than about 2 mm, less than about 1 mm, less than about 500 microns, less than about 60 mesh (250 microns), less than about 100 mesh (149 microns), less than about 140 mesh (105 microns), less than about 170 mesh (88 microns), less than about 200 mesh (74 microns), less than about 270 mesh (53 microns), or less than about 400 mesh (37 microns), or smaller.

In some cases, it may be desirable to employ feed material with an average particle size above a minimum amount in order to reduce the pressure required to pass the hydrocarbonaceous feed material through the reactor. For example, in some cases, it may be desirable to use solid hydrocarbonaceous material with an average particle size of at least about 400 mesh (37 microns), at least about 270 mesh (53 microns), at least about 200 mesh (74 microns), at least about 170 mesh (88 microns), at least about 140 mesh (105 microns), at least about 100 mesh (149 microns), at least about 60 mesh (250 microns), at least about 500 microns, a least about 1 mm, at least about 2 mm, at least about 5 mm, or higher.

Catalyst components useful in the context of this invention can be selected from any catalyst known in the art, or as would be understood by those skilled in the art made aware of this invention. Functionally, catalysts may be limited only by the capability of any such material to promote and/or effect dehydration, dehydrogenation, isomerization, hydrogen transfer, aromatization, decarbonylation, decarboxylation, aldol condensation and/or any other reaction or process associated with or related to the pyrolysis of a hydrocarbonaceous material. Catalyst components can be considered acidic, neutral or basic, as would be understood by those skilled in the art.

The catalyst particles described herein can comprise polycrystalline solids (e.g., polycrystalline particles) in some cases. The catalyst particles can also comprise single crystals, in some embodiments. In certain cases, the particles may be distinct and separate physical objects that are stand-alone. In other cases, the particles may, at least at certain points in their preparation and/or use, comprise an agglomerate of a plurality of individual particles in intimate contact with each other.

A catalyst used in embodiments described herein (e.g., in the feed stream, in the reactor, etc.) may be of any suitable size. In some cases, it may be advantageous to use catalysts comprising relatively small catalyst particles, which may, as mentioned previously, in certain embodiments, be in the form of larger catalyst objects that may be comprised of a plurality of agglomerated catalyst particles. In some embodiments, for example, the use of small catalyst particles may increase the extent to which the hydrocarbonaceous material may contact the surface sites of the catalyst due to, for example, increased external catalytic surface area and decreased diffusion distances through the catalyst. In some cases, catalyst size and/or catalyst particle size may be chosen based at least in part on, for example, the type of fluid flow desired and the catalyst lifetime.

In some embodiments, the average diameter (as measured by conventional sieve analysis) of catalyst objects, which may in certain instances each comprise a single catalyst particle or in other instances comprise an agglomerate of a plurality of particles, may be less than about 5 mm, less than about 2 mm, less than about 1 mm, less than about 500 microns, less than about 60 mesh (250 microns), less than about 100 mesh (149 microns), less than about 140 mesh (105 microns), less than about 170 mesh (88 microns), less than about 200 mesh (74 microns), less than about 270 mesh (53 microns), or less than about 400 mesh (37 microns), or smaller.

In some embodiments, the catalyst objects can be or be formed of particles having a maximum cross-sectional dimension of less than about 5 microns, less than about 1 micron, less than about 500 nm, less than about 100 nm, between about 100 nm and about 5 microns, between about 500 nm and about 5 microns, between about 100 nm and about 1 micron, or between about 500 nm and about 1 micron. As noted previously, in certain cases, catalyst particles having the dimensions within the ranges noted immediately above may be agglomerated to form discrete catalyst objects having dimensions within the ranges noted in the previous paragraph. As used here, the "maximum cross-sectional dimension" of a particle refers to the largest dimension between two boundaries of a particle. One of ordinary skill in the art would be capable of measuring the maximum cross-sectional dimension of a particle by, for example, analyzing a scanning electron micrograph (SEM) of a catalyst preparation. In embodiments comprising agglomerated particles, the particles should be considered separately when determining the maximum cross-sectional dimensions. In such a case, the measurement would be performed by establishing imaginary boundaries between each of the agglomerated particles, and measuring the maximum cross-sectional dimension of the hypothetical, individuated particles that result from establishing such boundaries. In some embodiments, a relatively large number of the particles within a catalyst have maximum cross-sectional dimensions that lie within a given range. For example, in some embodiments, at least about 50%, at least about 75%, at least about 90%, at least about 95%, or at least about 99% of the particles within a catalyst have maximum cross-sectional dimensions of less than about 5 microns, less than about 1 micron, less than about 500 nm, less than about 100 nm, between about 100 nm and about 5 microns, between about 500 nm and about 5 microns, between about 100 nm and about 1 micron, or between about 500 nm and about 1 micron.

A relatively large percentage of the volume of the catalyst can be occupied by particles with maximum cross-sectional dimensions within a specific range, in some cases. For example, in some embodiments, at least about 50%, at least about 75%, at least about 90%, at least about 95%, or at least about 99% of the sum of the volumes of all the catalyst used is occupied by particles having maximum cross-sectional dimensions of less than about 5 microns, less than about 1 micron, less than about 500 nm, less than about 100 nm, between about 100 nm and about 5 microns, between about 500 nm and about 5 microns, between about 100 nm and about 1 micron, or between about 500 nm and about 1 micron.

In some embodiments, the particles within a catalyst may be substantially the same size. For example, the catalyst can comprise particles with a distribution of dimensions such that the standard deviation of the maximum cross-sectional dimensions of the particles is no more than about 50%, no more than about 25%, no more than about 10%, no more than about 5%, no more than about 2%, or no more than about 1% of the average maximum cross-sectional dimensions of the particles. Standard deviation (lower-case sigma) is given its normal meaning in the art, and may be calculated as:

$$\sigma = \sqrt{\frac{\sum_{i=1}^{n}(D_i - D_{avg})^2}{n-1}}$$

wherein $D_i$ is the maximum cross-sectional dimension of particle i, $D_{avg}$ is the average of the maximum cross-sectional dimensions of all the particles, and n is the number of particles within the catalyst. The percentage comparisons between the standard deviation and the average maximum cross-sectional dimensions of the particles outlined above can be obtained by dividing the standard deviation by the average and multiplying by 100%.

Using catalysts including particles within a chosen size distribution indicated above can lead to an increase in the yield and/or selectivity of aromatic compounds produced by the reaction of the hydrocarbonaceous material. For example, in some cases, using catalysts containing particles with a desired size range (e.g., any of the size distributions outlined above) can result in an increase in the amount of aromatic compounds in the reaction product of at least about 5%, at least about 10%, or at least about 20%, relative to an amount of aromatic compounds that would be produced using catalysts containing particles with a size distribution outside the desired range (e.g., with a large percentage of particles larger than 1 micron, larger than 5 microns. etc.).

Alternatively, alone or in conjunction with the considerations mentioned above, catalysts can be selected according to pore size (e.g., mesoporous and pore sizes typically associated with zeolites), e.g., average pore sizes of less than about 100 Angstroms, less than about 50 Angstroms, less than about 20 Angstroms, less than about 10 Angstroms, less than about 5 Angstroms, or smaller. In some embodiments, catalysts with average pore sizes of from about 5 Angstroms to about 100 Angstroms may be used. In some embodiments, catalysts with average pore sizes of between about 5.5 Angstroms and about 6.5 Angstroms, or between about 5.9 Angstroms and about 6.3 Angstroms may be used. In some cases, catalysts with average pore sizes of between about 7 Angstroms and about 8 Angstroms, or between about 7.2 Angstroms and about 7.8 Angstroms may be used.

As used herein, the term "pore size" is used to refer to the smallest cross-sectional diameter of a pore. The smallest cross-sectional diameter of a pore may correspond to the smallest cross-sectional dimension (e.g., a cross-sectional diameter) as measured perpendicularly to the length of the pore. In some embodiments, a catalyst with an "average pore size" or a "pore size distribution" of X refers to a catalyst in which the average of the smallest cross-sectional diameters of the pores within the catalyst is about X. It should be understood that "pore size" or "smallest cross sectional diameter" of a pore as used herein refers to the Norman radii adjusted pore size well known to those skilled in the art. Determination of Norman radii adjusted pore size is described, for example, in Cook, M.; Conner, W. C., "How big are the pores of zeolites?" Proceedings of the International Zeolite Conference, 12th, Baltimore, Jul. 5-10, 1998; (1999), 1, pp 409-414, which is incorporated herein by reference in its entirety. A list of exemplary Norman radii adjusted pore sizes are shown, for example, in FIG. 17. As a specific exemplary calculation, the atomic radii for ZSM-5 pores are about 5.5-5.6 Angstroms, as measured by x-ray diffraction. In order to adjust for the repulsive effects between the oxygen atoms in the catalyst, Cook and Conner have shown that the Norman adjusted radii are 0.7 Angstroms larger than the atomic radii (about 6.2-6.3 Angstroms).

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et al, "Fundamentals of Powder Diffraction and Structural Characterization of Materials," Springer Science+Business Media, Inc., New York, 2005, incorporated herein by reference in its entirety. Other techniques that may be useful in determining pore sizes (e.g., zeolite pore sizes) include, for example, helium pycnometry or low pressure argon adsorption techniques. These and other techniques are described in Magee, J. S. et al, "Fluid Catalytic Cracking: Science and Technology," Elsevier Publishing Company, Jul. 1, 1993, pp. 185-195, which is incorporated herein by reference in its entirety. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, 1998, both incorporated herein by reference in their entirety. Unless otherwise indicated, pore sizes referred to herein are those determined by x-ray diffraction corrected as described above to reflect their Norman radii adjusted pore sizes.

In some embodiments, a screening method is used to select catalysts with appropriate pore sizes for the conversion of specific pyrolysis product molecules. The screening method may comprise determining the size of pyrolysis product molecules desired to be catalytically reacted (e.g., the molecule kinetic diameters of the pyrolysis product molecules). One of ordinary skill in the art can calculate, for example, the kinetic diameter of a given molecule. The type of catalyst may then be chosen such that the pores of the catalyst (e.g., Norman adjusted minimum radii) are sufficiently large to allow the pyrolysis product molecules to diffuse into and/or react with the catalyst. In some embodiments, the catalysts are chosen such that their pore sizes are sufficiently small to prevent entry and/or reaction of pyrolysis products whose reaction would be undesirable.

Without limitation, some such and other catalysts can be selected from naturally-occurring zeolites, synthetic zeolites and combinations thereof. In certain embodiments, the catalyst may be a Mordenite Framework Inverted (MFI) type zeolite catalyst, such as a ZSM-5 zeolite catalyst, as would be understood by those skilled in the art. Optionally, such a catalyst can comprise acidic sites. Other types of zeolite catalysts include ferrierite, zeolite Y, zeolite beta, modernite, MCM-22, ZSM-23, ZSM-57, SUZ-4, EU-1, ZSM-11, (S)AlPO-31, SSZ-23, among others. In other embodiments, non-zeolite catalysts may be used. For example, $WO_x/ZrO_2$, aluminum phosphates, etc.

In some embodiments, the catalyst may comprise a metal and/or a metal oxide. Suitable metals and/or oxides include, for example, nickel, platinum, vanadium, palladium, manganese, cobalt, zinc, copper, chromium, gallium, and/or any of their oxides, among others. The metal and/or metal oxide can be impregnated into the catalyst (e.g., in the interstices of the lattice structure of the catalyst), in some embodiments. The metal and/or metal oxide might be incorporated into the lattice structure of the catalyst. For example, the metal and/or metal oxide might be included during the preparation of the catalyst, and the metal and/or metal oxide can occupy a lattice site of the resulting catalyst (e.g., a zeolite catalyst). As another example, the metal and/or metal oxide can react or otherwise interact with a zeolite such that the metal and/or metal oxide displaces an atom within the lattice structure of the zeolite.

In certain embodiments, a Mordenite Framework Inverted (MFI) zeolite catalyst comprising gallium can be used. For example, a galloaluminosilicate MFI (GaAlMFI) zeolite catalyst can be used. One of ordinary skill in the art would be familiar with GaAlMFI zeolites, which can be thought of as aluminosilicate MFI zeolites in which some of the Al atoms have been replaced with Ga atoms. In some instances, the zeolite catalyst can be in the hydrogen form (e.g., H—GaAlMFI). The galloaluminosilicate MFI catalyst can be a ZSM-5 zeolite catalyst in which some of the aluminum atoms have been replaced with gallium atoms, in some embodiments.

In some instances, the ratio of moles of Si in the galloaluminosilicate zeolite catalyst to the sum of the moles of Ga and Al (i.e., the molar ratio expressed as Si:(Ga+Al)) in the galloaluminosilicate zeolite catalyst can be at least about 15:1, at least about 20:1, at least about 25:1, at least about 35:1, at least about 50:1, at least about 75:1, or higher. In some embodiments, it may be advantageous to employ a catalyst with a ratio of moles of Si in the zeolite to the sum of the moles of Ga and Al of between about 15:1 and about 100:1, from about 15:1 to about 75:1, between about 25:1 and about 80:1, or between about 50:1 and about 75:1. In some instances, the ratio of moles of Si in the galloaluminosilicate zeolite catalyst to the moles of Ga in the galloaluminosilicate zeolite catalyst can be at least about 30:1, at least about 60:1, at least about 120:1, at least about 200:1, between about 30:1 and about 300:1, between about 30:1 and about 200:1, between about 30:1 and about 120:1, or between about 30:1 and about 75:1. The ratio of the moles of Si in the galloaluminosilicate zeolite catalyst to the moles of Al in the galloaluminosilicate zeolite catalyst can be at least about 10:1, at least about 20:1, at least about 30:1, at least about 40:1, at least about 50:1, at least about 75:1, between about 10:1 and about 100:1, between about 10:1 and about 75:1, between about 10:1 and about 50:1, between about 10:1 and about 40:1, or between about 10:1 and about 30:1.

In addition, in some cases, properties of the catalysts (e.g., pore structure, type and/or number of acid sites, etc.) may be chosen to selectively produce a desired product.

It may be desirable, in some embodiments, to employ one or more catalysts to establish a bimodal distribution of pore sizes. In some cases, a single catalyst with a bimodal distribution of pore sizes may be used (e.g., a single catalyst that contains predominantly 5.9-6.3 Angstrom pores and 7-8 Angstrom pores). In other cases, a mixture of two or more catalysts may be employed to establish the bimodal distribution (e.g., a mixture of two catalysts, each catalyst type including a distinct range of average pore sizes). In some embodiments, one of the one or more catalysts comprises a zeolite catalyst and another of the one or more catalysts comprises a non-zeolite catalyst (e.g., a mesoporous catalyst, a metal oxide catalyst, etc.).

For example, in some embodiments at least about 70%, at least about 80%, at least about 90%, at least about 95%, at least about 98%, or at least about 99% of the pores of the one or more catalysts (e.g., a zeolite catalyst, a mesoporous catalyst, etc.) have smallest cross-sectional diameters that lie within a first size distribution or a second size distribution. In some cases, at least about 2%, at least about 5%, or at least about 10% of the pores of the one or more catalysts have smallest cross-sectional diameters that lie within the first size distribution; and at least about 2%, at least about 5%, or at least about 10% of the pores of the one or more catalysts have smallest cross-sectional diameters that lie within the second size distribution. In some cases, the first and second size distributions are selected from the ranges provided above. In certain embodiments, the first and second size distributions are different from each other and do not overlap. An example of a non-overlapping range is 5.9-6.3 Angstroms and 6.9-8.0 Angstroms, and an example of an overlapping range is 5.9-6.3 Angstroms and 6.1-6.5 Angstroms. The first and second size distributions may be selected such that the range are not immediately adjacent one another, an example being pore sizes of 5.9-6.3 Angstroms and 6.9-8.0 Angstroms. An example of a range that is immediately adjacent one another is pore sizes of 5.9-6.3 Angstroms and 6.3-6.7 Angstroms.

As a specific example, in some embodiments one or more catalysts is used to provide a bimodal pore size distribution for the simultaneous production of aromatic and olefin compounds. That is, one pore size distribution may advantageously produce a relatively high amount of aromatic compounds, and the other pore size distribution may advantageously produce a relatively high amount of olefin compounds. In some embodiments, at least about 70%, at least about 80%, at least about 90%, at least about 95%, at least about 98%, or at least about 99% of the pores of the one or more catalysts have smallest cross-sectional diameters between about 5.9 Angstroms and about 6.3 Angstroms or between about 7 Angstroms and about 8 Angstroms. In addition, at least about 2%, at least about 5%, or at least about 10% of the pores of the one or more catalysts have smallest cross-sectional diameters between about 5.9 Angstroms and about 6.3 Angstroms; and at least about 2%, at least about 5%, or at least about 10% of the pores of the one or more catalysts have smallest cross-sectional diameters between about 7 Angstroms and about 8 Angstroms.

In some embodiments, at least about 70%, at least about 80%, at least about 90%, at least about 95%, at least about 98%, or at least about 99% of the pores of the one or more catalysts have smallest cross-sectional diameters between about 5.9 Angstroms and about 6.3 Angstroms or between about 7 Angstroms and about 200 Angstroms. In addition, at least about 2%, at least about 5%, or at least about 10% of the pores of the one or more catalysts have smallest cross-sectional diameters between about 5.9 Angstroms and about 6.3 Angstroms; and at least about 2%, at least about 5%, or at least about 10% of the pores of the one or more catalysts have smallest cross-sectional diameters between about 7 Angstroms and about 200 Angstroms.

In some embodiments, at least about 70%, at least about 80%, at least about 90%, at least about 95%, at least about 98%, or at least about 99% of the pores of the one or more catalysts have smallest cross-sectional diameters that lie within a first distribution and a second distribution, wherein the first distribution is between about 5.9 Angstroms and about 6.3 Angstroms and the second distribution is different from and does not overlap with the first distribution. In some embodiments, the second pore size distribution may be between about 7 Angstroms and about 200 Angstroms, between about 7 Angstroms and about 100 Angstroms, between about 7 Angstroms and about 50 Angstroms, or between about 100 Angstroms and about 200 Angstroms. In some embodiments, the second catalyst may be mesoporous (e.g., have a pore size distribution of between about 2 nm and about 50 nm).

In some embodiments, the bimodal distribution of pore sizes may be beneficial in reacting two or more hydrocarbonaceous feed material components. For example, some embodiments comprise providing a solid hydrocarbonaceous material comprising a first component and a second component in a reactor, wherein the first and second components are different. Examples of compounds that may be used as first or second components include any of the hydrocarbonaceous materials described herein (e.g., sugar cane bagasse, glucose, wood, corn stover, cellulose, hemi-cellulose, lignin, or any others). For example, the first component may comprise one of cellulose, hemi-cellulose and lignin, and the second component comprises one of cellulose, hemicellulose and lignin. The method may further comprise providing first and second catalysts in the reactor. In some embodiments, the first catalyst may have a first pore size distribution and the second catalyst may have a second pore size distribution, wherein the first and second pore size distributions are different and do not overlap. The first pore size distribution may be, for example, between about 5.9 Angstroms and about 6.3 Angstroms. The second pore size distribution may be, for example, between about 7 Angstroms and about 200 Angstroms, between about 7 Angstroms and about 100 Angstroms, between about 7 Angstroms and about 50 Angstroms, or between about 100 Angstroms and about 200 Angstroms. In some cases, the second catalyst may be mesoporous or non-porous.

The first catalyst may be selective for catalytically reacting the first component or a derivative thereof to produce a fluid hydrocarbon product. In addition, the second catalyst may be selective for catalytically reacting the second component or a derivative thereof to produce a fluid hydrocarbon product. The method may further comprise pyrolyzing within the reactor at least a portion of the hydrocarbonaceous material under reaction conditions sufficient to produce one or more pyrolysis products and catalytically reacting at least a portion of the pyrolysis products with the first and second catalysts to produce the one or more hydrocarbon products. In some instances, at least partially deactivated catalyst may also be produced.

In certain embodiments, a method used in combination with embodiments described herein includes increasing the catalyst to hydrocarbonaceous material mass ratio of a composition to increase production of identifiable aromatic compounds. As illustrated herein, representing but one distinction over certain prior catalytic pyrolysis methods, articles and methods described herein can be used to produce discrete, identifiable aromatic, biofuel compounds selected from but not limited to benzene, toluene, propylbenzene, ethylbenzene, methylbenzene, methylethylbenzene, trimethylbenzene, xylenes, indanes, naphthalene, methylnaphthelene, dimethylnaphthalene, ethylnaphthalene, hydrindene, methylhydrindene, and dimethylhydrindene and combinations thereof.

In some embodiments, the reaction chemistry of a catalyst may be affected by adding one or more additional compounds. For example, the addition of a metal to a catalyst may result in a shift in selective formation of specific compounds (e.g., addition of metal to alumina-silicate catalysts may result in the production of more CO). In addition, when the fluidization fluid comprises hydrogen, the amount of coke formed on the catalyst may be decreased.

In some embodiments, the catalyst may comprise both silica and alumina (e.g., a zeolite catalyst). The silica and alumina in the catalyst may be present in any suitable molar ratio. In some embodiments, it may be advantageous to employ catalysts with a larger number of moles of silica relative to the number of moles of alumina (i.e., a high silica to alumina molar ratio). The inventors have unexpectedly discovered that high silica to alumina molar ratios, e.g., in combination with embodiments described herein, may result in the formation of a relatively large amount of aromatic product. For example, in some cases, the feed composition may comprise a silica to alumina molar ratio of at least about 30:1, at least about 40:1, at least about 50:1, at least about 75:1, at least about 100:1, at least about 150:1, or higher. In some embodiments, it may be advantageous to employ a catalyst with a silica to alumina molar ratio of between about 30:1 and about 200:1, from about 30:1 to about 150:1, between about 50:1 and about 160:1, or between about 100:1 and about 150:1.

In some embodiments, catalyst and hydrocarbonaceous material may be present in any suitable ratio. For example, the catalyst and hydrocarbonaceous material may be present in any suitable mass ratio in cases where the feed composition (e.g., through one or more feed streams comprising catalyst and hydrocarbonaceous material or through separate catalyst and hydrocarbonaceous material feed streams), comprises catalyst and hydrocarbonaceous material (e.g., circulating fluidized bed reactors). As another example, in cases where the reactor is initially loaded with a mixture of catalyst and hydrocarbonaceous material (e.g., a batch reactor), the catalyst and hydrocarbonaceous material may be present in any suitable mass ratio. In some embodiments involving circulating fluidized bed reactors, the mass ratio of the catalyst to hydrocarbonaceous material in the feed stream—i.e., in a composition comprising a solid catalyst and a solid hydrocarbonaceous material provided to a reactor—may be at least about 0.5:1, at least about 1:1, at least about 2:1, at least about 5:1, at least about 10:1, at least about 15:1, at least about 20:1, or higher. In some embodiments involving circulating fluidized bed reactors, the mass ratio of the catalyst to hydrocarbonaceous material in the feed stream may be less than about 0.5:1, less than about 1:1, less than about 2:1, less than about 5:1, less than about 10:1, less than about 15:1, or less than about 20:1; or from about 0.5:1 to about 20:1, from about 1:1 to about 20:1, or from about 5:1 to about 20:1. Employing a relatively high catalyst to hydrocarbonaceous material mass ratio may facilitate introduction of the volatile organic compounds, formed from the pyrolysis of the feed material, into the catalyst before they thermally decompose to coke. Not wishing to be bound by any theory, this effect may be at least partially due to the presence of a stoichiometric excess of catalyst sites within the reactor.

In another aspect, a process product is described. In one set of embodiments, a product (e.g., a pyrolysis product) comprises a fluid composition comprising a portion of a reaction product of a solid hydrocarbonaceous material. Such products can be isolated for use as specialty chemicals (e.g., used as fuel directly or as high octane fuel additives) or, alternatively, hydrogenated for use as a biofuel. The products can also be further processed to make other useful compounds.

In some embodiments, the articles and methods described herein are configured to selectively produce aromatic compounds, e.g., in a single-stage, or alternatively, a multi-stage pyrolysis apparatus. A fluid hydrocarbon product may comprise, for example, an amount of aromatic compounds that comprises at least about 10 wt %, at least about 15 wt %, at least about 20 wt %, at least about 25 wt %, at least about 30 wt %, at least about 35 wt %, at least about 39 wt %, between about 10 wt % and about 40 wt %, between about 10 wt % and about 35 wt %, between about 15 wt % and about 40 wt %, between about 15 wt % and about 35 wt %, between about 20 wt % and about 40 wt %, between about 20 wt % and about 35 wt %, between about 25 wt % and about 40 wt %, between about 25 wt % and about 35 wt %, between about 30 wt % and about 40 wt %, or between about 30 wt % and about 35 wt % of the total reaction product of the solid hydrocarbonaceous material. In some cases, such amounts of aromatic compounds have an octane number greater than or equal to about 90, e.g., at least 92, 95, or 98. The amount of aromatic compounds that comprise a weight percentage of the total reaction product of the solid hydrocarbonaceous material is calculated as the weight of the aromatic compounds present in the fluid hydrocarbon product divided by the weight of the hydrocarbonaceous material used in forming the pyrolysis products. As used herein, the term "aromatic compound" is used to refer to a hydrocarbon compound comprising one or more aromatic groups such as, for example, single aromatic ring systems (e.g., benzyl, phenyl, etc.) and fused polycyclic aromatic ring systems (e.g. naphthyl, 1,2,3,4-tetrahydronaphthyl, etc.). Examples of aromatic compounds include, but are not limited to, benzene, toluene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, methylbenzene, propylbenzene, xylenes (e.g., p-xylene, m-xylene, o-xylene, etc.), naphthalene, methyl-naphthalene (e.g., 1-methyl naphthalene, anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, and dymethyl-hydrindene. Single ring and/or higher ring aromatics may be produced in some embodiments. The aromatic compounds may have carbon numbers from, for example, $C_5$-$C_{14}$, $C_6$-$C_8$, $C_6$-$C_{12}$, $C_8$-$C_{12}$, $C_{10}$-$C_{14}$.

In some embodiments, the articles and methods described herein are configured to selectively produce olefin compounds, e.g., in a single-stage, or alternatively, a multi-stage pyrolysis apparatus. A fluid composition (e.g., liquid and/or gaseous pyrolysis product) may comprise, for example, an amount of olefin compounds that includes at least about 3 wt %, at least about 7 wt %, at least about 10 wt %, at least about 12.5 wt %, at least about 15 wt %, at least about 20 wt % or more of the total reaction product of the solid hydrocarbonaceous material. The amount of olefin compounds that comprise a weight percentage of the total reaction product of the solid hydrocarbonaceous material is calculated as the weight of the olefin compounds present in the fluid hydrocarbon product divided by the weight of the hydrocarbonaceous material used in forming the pyrolysis products. As used herein, the terms "olefin" or "olefin compound" (a.k.a. "alkenes") are given their ordinary meaning in the art, and are used to refer to any unsaturated hydrocarbon containing one or more pairs of carbon atoms linked by a double bond.

Olefins include both cyclic and acyclinc (aliphatic) olefins, in which the double bond is located between carbon atoms forming part of a cyclic (closed-ring) or of an open-chain grouping, respectively. In addition, olefins may include any suitable number of double bonds (e.g., monoolefins, diolefins, triolefins, etc.). Examples of olefin compounds include, but are not limited to, ethene, propene, butene, butadiene, and isoprene, among others. The olefin compounds may have carbon numbers from, for example, $C_2$-$C_4$, $C_2$-$C_8$, $C_4$-$C_8$, or $C_2$-$C_{12}$.

Process conditions may be chosen, in some cases, such that aromatic and/or olefin compounds are selectively produced, e.g., in a single-stage, or alternatively, a multi-stage pyrolysis apparatus. For example, in some embodiments, aromatic and/or olefin compounds may be selectively produced when the reactor is operated at a temperature of about 600° C. (or higher, in some instances). In addition, certain heating rates (e.g., at least about 50° C./s, or at least about 400° C./s), high catalyst-to-feed mass ratios (e.g., at least about 5:1), and/or high silica to alumina molar ratios in the catalyst (e.g., at least about 30:1) may be used to facilitate selective production of aromatic and/or olefin compounds. Some such and other process conditions may be combined with a particular reactor type, such as a fluidized bed reactor (e.g., a circulating fluidized bed reactor), to selectively produce aromatic and/or olefin compounds.

Furthermore, in some embodiments, the catalyst may be chosen to facilitate selective production of aromatic and/or olefin products. For example, ZSM-5 may, in some cases, preferentially produce relatively higher amounts of aromatic and/or olefin compounds. In some cases, catalysts that include Bronstead acid sites may facilitate selective production aromatic compounds. In addition, catalysts with well-ordered pore structures may facilitate selective production of aromatic compounds. For example, in some embodiments, catalysts with average pore diameters between about 5.9 Angstroms and about 6.3 Angstroms may be particularly useful in producing aromatic compounds. In addition, catalysts with average pore diameters between about 7 Angstroms and about 8 Angstroms may be useful in producing olefins. In some embodiments, a combination of one or more of the above process parameters may be employed to facilitate selective production of aromatic and/or olefin compounds. The ratio of aromatics to olefins produced may be, for example, between about 0.1:1 and about 10:1, between about 0.2:1 and about 5:1, between about 0.5:1 and about 2:1, between about 0.1:1 and about 0.5:1, between about 0.5:1 and about 1:1, between about 1:1 and about 5:1, or between about 5:1 and about 10:1.

In some embodiments, the catalyst to hydrocarbonaceous material mass ratio in the feed is adjusted to produce desirable products and/or favorable yields. In some embodiments, oxygenated compounds may be produced, such as, for example, acetic acid, formic acid, hydroxyacetylaldehyde, furfural, 2-methyl furan, furan, 4-methyl furfural, furan-2-methanol, and levoglucosan, among others. For example, in some cases, increasing the catalyst to hydrocarbonaceous material mass ratio may result in an increase in the production of non-cyclic carbonyl oxygenated compounds. As a specific example, as the catalyst to feed (e.g., glucose) mass ratio in the feed is increased but maintained below a mass ratio of about 9, the relative amount of non-cyclic carbonyl oxygenated products (e.g., hydroxyacetaldehyde, acetic acid, etc.) may be increased. In some cases, decreasing the catalyst to hydrocarbonaceous material mass ratio may result in an increase in the production of cyclic oxygenated compounds. For example, in some cases, as the catalyst to feed (e.g., glucose) mass ratio in the feed is decreased (e.g., from about 19 to about 1), the relative amount of furan, furfural, methyl-furan, and/or 4-methyl furfural products is increased. In still further embodiments, as the catalyst to feed (e.g., glucose) mass ratio in the feed is decreased (e.g., from about 19 to about 2.3) the amount of furan-2-methanol product may be increased; and as the catalyst to feed (e.g., glucose) mass ratio in the feed is decreased further (e.g., from about 2.3 to about 1.5) the amount of furan-2-methanol product may be decreased. As such, the catalyst to hydrocarbonaceous material mass ratio may be, for example, at least about 0.5:1, at least about 1:1, at least about 2:1, at least about 5:1, at least about 10:1, at least about 15:1, at least about 20:1, or higher in some embodiments; or, less than about 0.5:1, less than about 1:1, less than about 2:1, less than about 5:1, less than about 10:1, less than about 15:1, or less than about 20:1 in other embodiments.

In some embodiments, the process product may also comprise a high-octane biofuel composition comprising a pyrolysis product of a hydrocarbonaceous biomass material. The pyrolysis product may be made using a single-stage pyrolysis apparatus, or alternatively, a multi-stage pyrolysis apparatus. In some cases, the hydrocarbonaceous material may be mixed with a catalyst (e.g., a zeolite catalyst) during the pyrolysis reaction. The composition may include, for example, discrete, identifiable aromatic compounds, one, more than one or each such compound characterized by an octane number greater than or equal to about 90, e.g., at least 92, 95, or 98. As distinguishable over some viscous tars and sludges of the prior art, such a biofuel composition can be characterized as soluble in petroleum-derived gasolines, diesel fuels and/or heating fuels. Such compounds can include, but are not limited to, benzene, toluene, ethylbenzene, methylethylbenzene, trimethylbenzene, xylenes, indanes naphthalene, methylnaphthelene, dimethylnaphthalene, ethylnaphthalene, hydrindene, methylhydrindene, and dimethylhydrindene and combinations thereof, the identity and/or relative amounts of which can vary depending upon choice of biomass composition, catalyst type, and/or any of the process parameters described herein.

In some embodiments, the process product may comprise a non-acidic biofuel compatible with existing gasoline and diesel fuel lines.

Furthermore, processes described herein may result in lower coke formation than certain existing methods. For example, in some embodiments, a pyrolysis product can be formed with less than about 30 wt %, less than about 25 wt %, less than about 20 wt %, than about 15 wt %, or less than about 10 wt % of the pyrolysis product being coke. The amount of coke formed is measured as the weight of coke formed in the system divided by the weight of hydrocarbonaceous material used in forming the pyrolysis product.

The following documents are incorporated herein by reference in their entireties for all purposes: U.S. Provisional Patent Application Ser. No. 61/068,001, filed Mar. 4, 2008, entitled "Catalytic Fast Pyrolysis of Solid Biomass and Related Biofuels and Aromatic Compounds," by Huber, et al.; U.S. Provisional Patent Application Ser. No. 61/098,284, filed Sep. 19, 2008, entitled "Catalytic Pyrolysis of Solid Biomass and Related Biofuels and Aromatic Compounds," by Huber, et al.; and U.S. patent application Ser. No. 12/397, 303. filed Mar. 3, 2009, entitled "Catalytic Pyrolysis of Solid Biomass and Related Biofuels, Aromatic, and Olefin Compounds," by Huber, et al.

EXAMPLES

The following non-limiting examples and data are intended to illustrate various aspects and features relating the methods and/or compositions of this invention, including the selective production of various aromatic and/or oxygenated compounds (e.g., oxygenated hydrocarbons), as available through the pyrolytic methodologies described herein, but do not exemplify the full scope of the invention. In comparison with the prior art, the methods and compositions of this invention provide results and data which are surprising, unexpected, and contrary thereto. While the utility of this invention is illustrated through the use of several catalyst materials and hydrocarbonaceous sources, it will be understood by those skilled in the art that comparable results are obtainable with various other catalyst materials and/or hydrocarbonaceous sources, as are commensurate with the scope of this invention.

Example 1

Figure 2A:
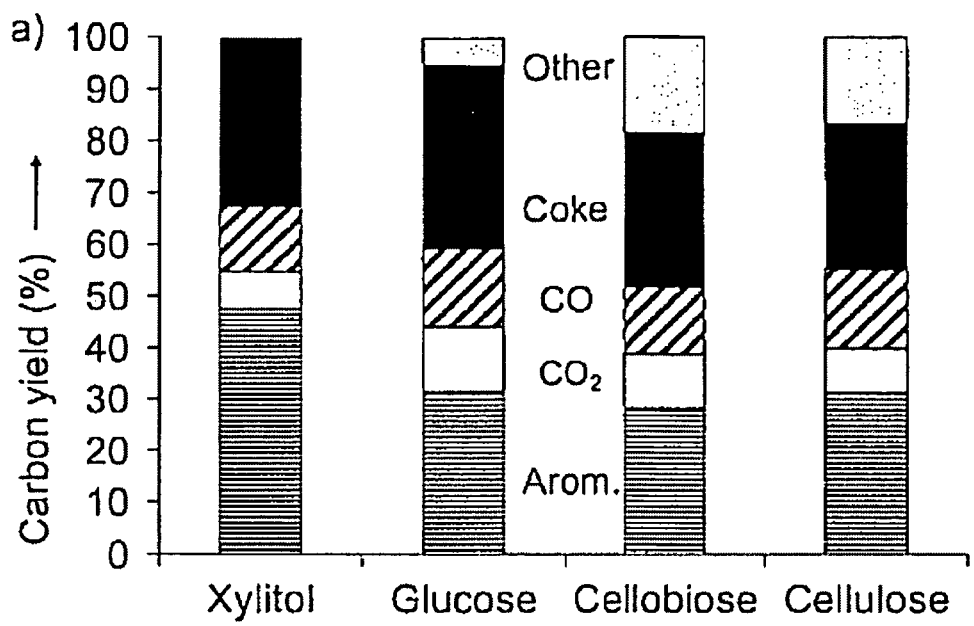
FIGS. 2A-2B are plots of (A) carbon yields for various biomass-derived feedstocks (aromatics: horizontal lines, $CO_2$: white, CO: diagonal lines, coke: black, and unidentified: grey) and (B) aromatic selectivity for feeds of benzene (Ben.), toluene (Tol.), ethyl-benzene and xylenes (E-Ben., Xyl.), methyl-ethyl-benzene and trimethyl-benzene (m,e-Ben., tmBen.), indanes (Ind.), and naphthalenes (Nap.) according to one set of embodiments.
Figure 2B:
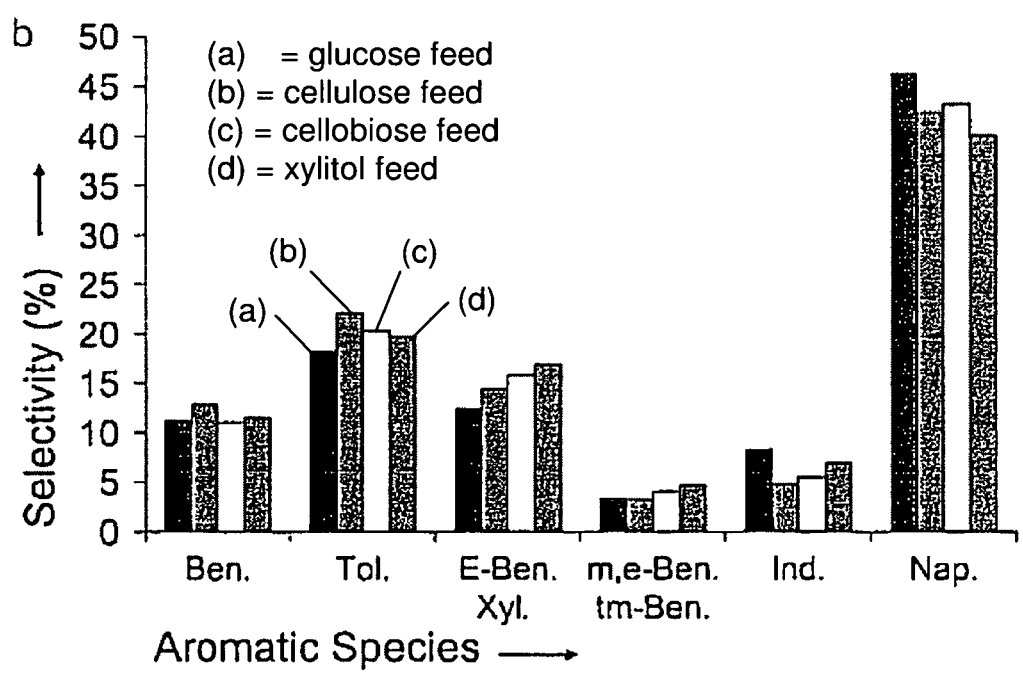

Representative of several embodiments, catalytic pyrolysis experiments described in Examples 1-9 below were conducted in a Pyroprobe 2000 batch pyrolysis reactor (CDS Analytical Inc.) with powdered catalyst and feed (<140 mesh size). Unless otherwise specified in this example, the reaction conditions for the experiments were: catalyst to feed weight ratio, 19; catalyst, ZSM5 ($SiO_2/Al_2O_3=30$); nominal heating rate, 1000° C. $s^{-1}$; reaction temperature, 600° C.; reaction time (residence time of feed), 240 s. FIGS. 2A-2B show the carbon yields and aromatic selectivity, respectively, for catalytic pyrolysis of xylitol, glucose, cellobiose and cellulose with HZSM-5 (i.e. protonated ZSM-5). The aromatic yields were calculated as carbon yields. Carbon yield was calculated by dividing the moles of carbon in the product by moles of carbon in the feed. The selectivity was calculated as the moles of carbon in a given product divided by the moles of carbon in all products (excluding CO, $CO_2$, and coke (e.g., solid coke remaining on the catalyst)). As can be seen from FIG. 2A, the major products included aromatics, CO, $CO_2$ and coke. Xylitol had a higher yield of aromatics than the other feeds. Xylitol also had a higher $H/C_{eff}$ molar ratio (2/5) than the other feeds (0 for cellulose, glucose, and cellobiose). Carbon monoxide and carbon dioxide were usually present as products when aromatics were desired. The aromatic yields of these reaction were about half of the theoretical yields given by Equations 1 and 2. Coke yield was about 30% for all catalysts tested, and in an industrial reactor could be burned to provide process heat for the catalytic pyrolysis.

It should be noted that one of ordinary skill in the art will be able to convert between weight percentages and carbon yield. The amount of carbon in a carbonaceous material feed may be determined, for example, via chemical analysis. In addition, the carbon percentage of each of the reaction products may be calculated using their molecular formulas. For example, 1 mole of benzene ($C_6H_6$) contains about 72 grams of carbon and about 6 grams of hydrogen, resulting in a weight percentage of carbon of about 92.3%. Similarly, methyl-benzene contains about 91.5 wt % carbon, and ethyl-benzene and xylene contain about 90.5 wt % carbon, etc. By dividing the mass of carbon in a particular product stream by the mass of carbon in the feed, carbon percentages may be determined from weight percentages.

In one specific example, toluene may be produced from a wood feed. Chemical analysis may be used to determine that the wood that is fed to the system is 44% carbon by mass (i.e., 44% carbon in the feed). The toluene produced is 91.25% carbon by mass (i.e., 91.25% carbon in the product). For a carbon yield (C %) of 5%, the weight percentage may be calculated as:

$$Wt\% = (5C\%)*(44\%)/(91.25\%) = 2.41 \text{ weight percent yield of toluene}$$

For a mixture of products (e.g. benzene, toluene, xylene and naphthalene) the sum of the individual product yields gives the total yield.

One of ordinary skill in the art will be able to determine the amount of carbon in a feed stream given available commercial technology. The feed composition or a hydrocarbonaceous material feed in terms of carbon and hydrogen percent can be determined, for example, by combustion analysis. In combustion analysis, a feed sample is weighed and subsequently burned in air (e.g., excess air) producing measurable combustion products such as carbon dioxide and water. The evolved carbon dioxide and water may be measured, for example, by trapping and weighing the gas or by gas chromatography. In this example, the moles of carbon dioxide ($CO_2$) measured would be equivalent to the moles of carbon (C) in the feed sample. In addition, the moles of water ($H_2O$) measured would be equal to ½ times the moles of hydrogen (H) in the feed sample.

When the reactor operates at steady-state, the mass exiting the reactor equals the mass fed to the reactor. In some instances, however, steady-state may not be achieved. For example, there may be accumulation of material (e.g., coke) within the reactor. In order to perform mass balance calculations, the amount of material that accumulates in the reactor must be determined. This can be accomplished, for example, by weighing the contents of the reactor before and after operation.

The aromatic distribution from catalytic pyrolysis of several representative biomass-derived oxygenates is shown in FIG. 2B. Interestingly, using the methods of this invention, the feedstocks tested yielded similar aromatic product distributions. The motor octane number (MON) of the aromatics was estimated to be 111. (For a complete list of the octane numbers (RON and MON) and boiling points of all the aromatics quantified, see the following examples.) Such and other aromatic products can be used as a fuel directly, as a high octane fuel additives, or may be further process to make different compounds. However, the naphthalenes produced had poor cold flow properties (i.e., low volatility) and current regulations limit levels in gasoline to 25% by volume. To alleviate these concerns, naphthalenes and other aromatics can be hydrogenated to alkanes in a secondary process, to enhance use as fuel additives.

Figure 3:
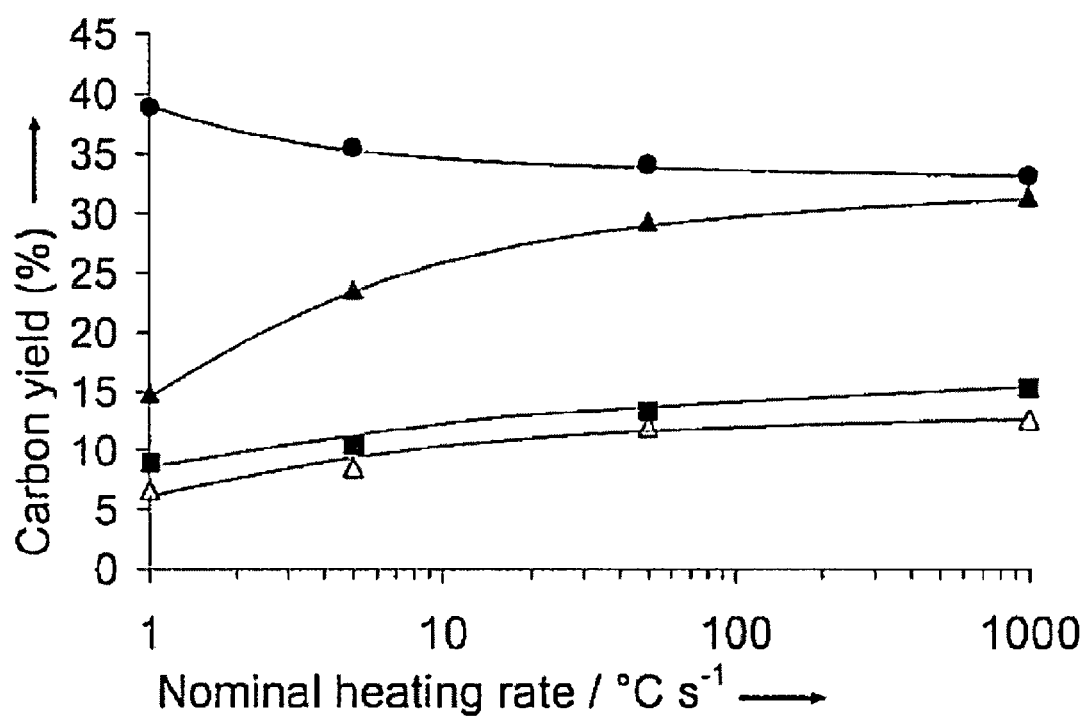
FIG. 3 is a plot of carbon yield of CO (■), aromatics (▲), $CO_2$ (Δ), and coke (•) as a function of nominal heating rate for a catalytic pyrolysis of glucose with ZSM5, according to one set of embodiments.

As can be seen from FIG. 3 the product yield for catalytic pyrolysis of glucose was a function of heating rate. The maximum aromatic yield and the lowest coke yield were obtained at a nominal heating rate of 1000° C. $s^{-1}$. When the heating rate was lowered by three orders of magnitude to 1° C. $s^{-1}$ the yield of aromatics decreased by half, and the yield of coke increased from 35 to 40%. Accordingly, it was determined that high rates of heating may be used to avoid undesired thermal decomposition reactions and coke formation.

Figure 4A:
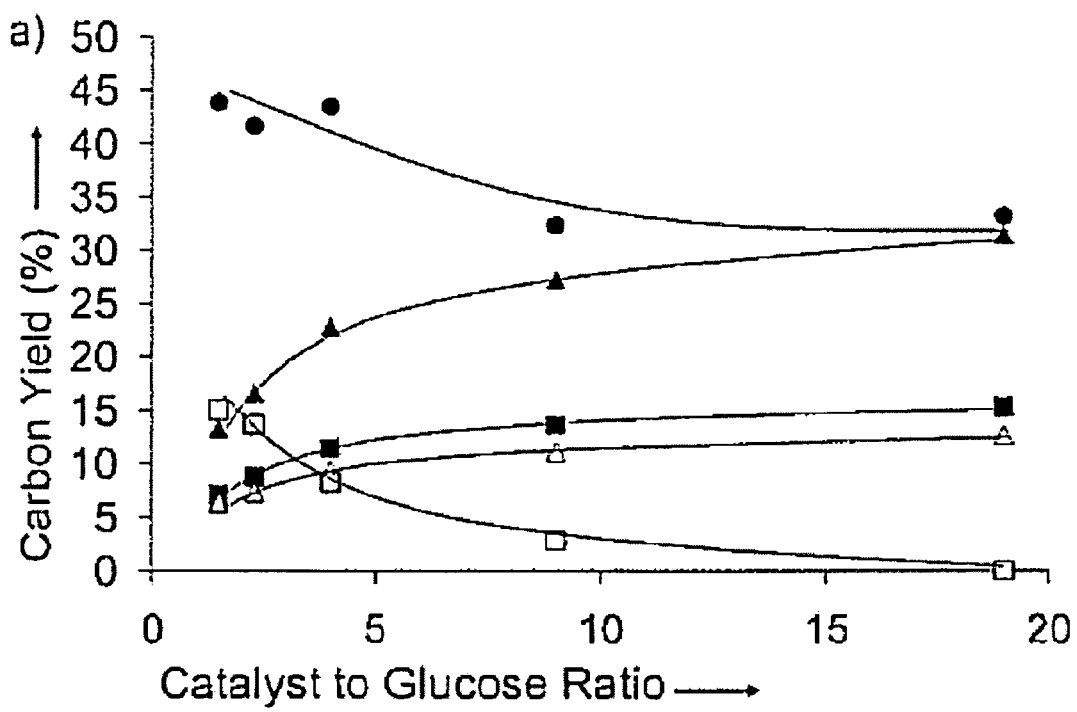
FIGS. 4A-4B are plots of (A) carbon yield of CO (■), aromatics (▲), $CO_2$ (Δ), partially deoxygenated species (□), and coke (•) as a function of catalyst to glucose mass ratio and (B) a distribution of partially deoxygenated species hydroxyacetylaldehyde (H.A.), acetic acid (A.A.), furan (Fur.), furfural (Furf), methyl furan (M-Fur), 4-methyl furfural (4-M-Furf), and furan-2-methanol (Fur-2-MeoH), according to one set of embodiments.
Figure 4B:
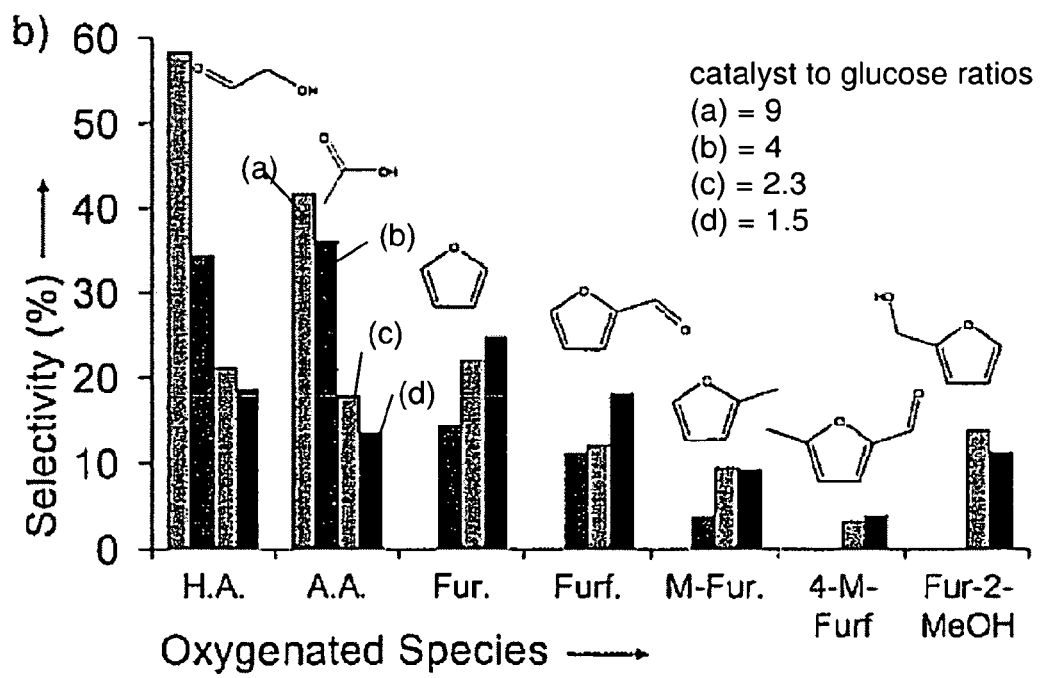

In addition to high heating rates, high mass ratios of catalyst to biomass can be utilized advantageously for aromatic production. FIGS. 4A-4B show the product selectivity for catalytic pyrolysis of glucose as a function of the catalyst to glucose mass ratio. The coke yield increased and the aromatic yield decreased as the catalyst to glucose mass ratio decreased. The yields of CO and $CO_2$ also decreased as the catalyst to glucose mass ratio decreased. In addition, at catalyst to glucose mass ratios lower than 19 thermally stable oxygenates were formed. The yield of these oxygenates decreased as the catalyst to glucose mass ratio increased. The oxygenates formed included furan, 2-methyl furan, furfural, 4-methylfurfaral, furan-2-methanol, hydroxyacetylaldehyde, and acetic acid, as shown in FIG. 4B. At higher catalyst to glucose mass ratios the major oxygenated products were hydroxyacetaldehyde and acetic acid. However the selectivity for furans increased as the catalyst to glucose mass ratio decreased. These results indicated that, in addition to aromatics, catalytic pyrolysis can be tuned to form oxygenates, which could be used as specialty chemicals or fuel precursors.

Figure 5:
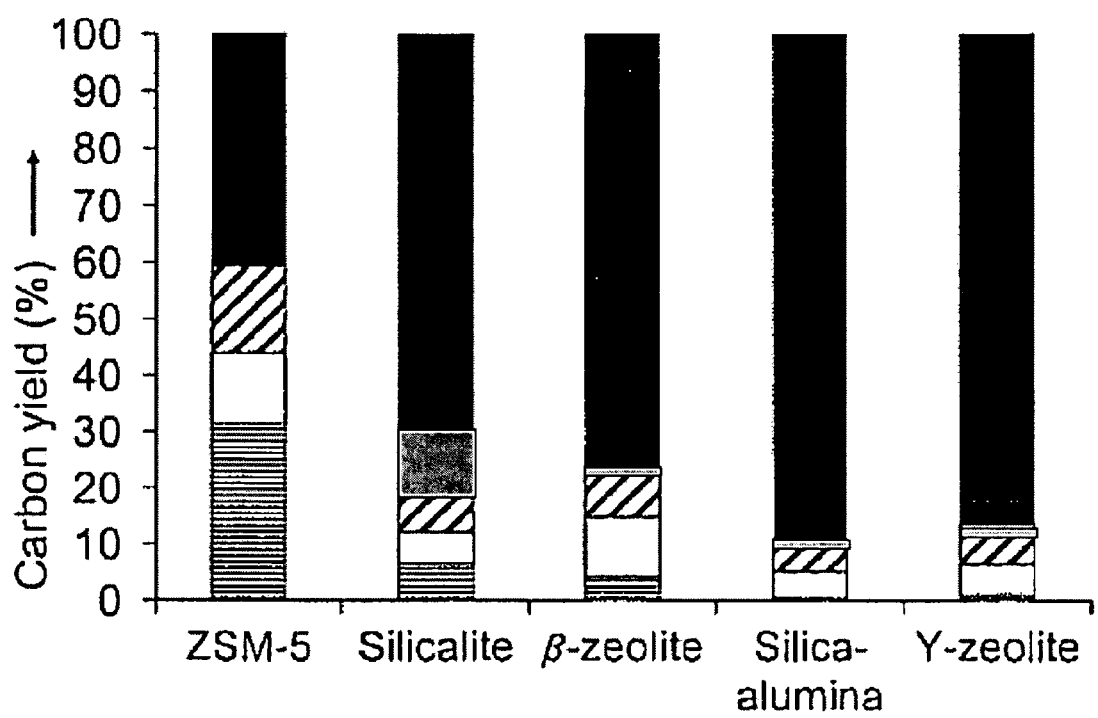
FIG. 5 is a plot of carbon yields after performing a catalytic pyrolysis of glucose with various catalysts (aromatics: horizontal lines, $CO_2$: white, CO: diagonal lines, partially deoxygenated species: grey, and coke: black) according to one set of embodiments.

Proper catalyst selection can also be used to selectively produce aromatics. FIG. 5 compares carbon yield from catalytic pyrolysis of glucose over several different catalysts. HZSM-5 had the highest aromatic yield of any catalyst tested. When no catalyst was used the primary product observed was coke. Two catalytic parameters that appeared to have an effect on product distribution were pore structure and the type of acid sites. The role of acid sites on catalytic activity, using representative ZSM-5, silicalite, and amorphous $SiO_2$—$Al_2O_3$ catalysts, was examined. Both silicalite and ZSM-5 have the same pore structure, but silicalite does not contain Bronstead acid sites. Silica-alumina contains Bronstead acid sites, but does not have a well-ordered pore structure. Silicalite produced primarily coke indicating that Bronstead acid sites may be useful for aromatic production. Silica alumna also produces primarily coke, indicating that the pore structure of the zeolite can be utilized to produce aromatics selectively. Also shown in FIG. 5 are β-Zeolite and Y-zeolite catalysts, which both also produce large amounts of coke. The results in FIG. 5 indicate that the method(s) of this invention may be varied by catalyst, type of active site, and the pore shape.

Experiments were conducted using a model 2000 pyro-probe analytical pyroliser (CDS Analytical Inc.). The probe was a computer controlled resistively heated element which held an open ended quartz tube. Powdered samples were held in the tube with loose quartz wool packing; during pyrolysis, vapors flowed from the open ends of the quartz tube into a larger cavity (the pyrolysis interface) with a helium carrier gas stream. The carrier gas stream was routed to a model 5890 gas chromatograph interfaced with a Hewlett Packard model 5972A mass selective detector. The pyrolysis interface was held at 100° C. and the GC injector temperature used was 275° C. Helium was used as the inert pyrolysis gas as well as the carrier gas for the GCMS system. A 0.5 ml min$^{-1}$ constant flow program was used for the GC capillary column. The GC oven was programmed with the following temperature regime: hold at 50° C. for 1 min, ramp to 200° C. at 10° C. min$^{-1}$, hold at 200° C. for 15 min.

Example 2

Powdered reactants were prepared by physically mixing the carbohydrate feed and the catalyst. Both the feed and the catalyst were sifted to <140 mesh before mixing. The physical mixtures of glucose tested were prepared with a D-glucose (Fisher) to HZSM-5 (Si/Al=30, WR Grace) mass ratio of 19, 9, 4, 2.3, and 1.5. Xyliol (Fisher)/ZSM-5, cellobiose (Acros)/ZSM-5, and cellulose (Whatnam)/ZSM-5 with a catalyst:feed mass ratio of 19 were also prepared. The HZSM-5 was calcined at 500° C. in air for 5 hours prior to reaction. Samples with a catalyst:glucose mass ratio of 19 were also prepared with the following catalysts: Silicalite, O-zeolite, Y-zeolite, and mesoporous $SiO_2/Al_2O_3$ ($SiO_2/Al_2O_3$=35). The reaction conditions, product yield, and product selectivities for all pyrolysis runs are summarized in Table 1. All runs were performed with a reaction temperature of 600° C. The yields are reported in terms of molar carbon yield where the moles of carbon in the product are divided by the moles of carbon in the reactant. The aromatic yields were calculated by dividing the moles of carbon in the aromatic product(s) by moles of carbon in the feed.

TABLE 1

Summary of pyrolysis experiments

| Feed | Catalyst | Catalyst to Feed Mass Ratio | Heating Rate (° C./s) | Reaction Time (s) | Aromatic Yield (%) | Oxygenated Yield (%) | $CO_2$ Yield (%) | CO Yield (%) | Coke Yield (%) | Total Carbon (%) | Unidentified (%) |
|---|---|---|---|---|---|---|---|---|---|---|---|
| glucose | ZSM-5 | 19 | 1000 | 240 | 31.4 | <1 | 12.6 | 15.3 | 33.2 | 92.5 | 7.5 |
| cellobiose | ZSM-5 | 19 | 1000 | 240 | 28.2 | <1 | 10.4 | 13.0 | 30.0 | 81.6 | 18.4 |
| cellulose | ZSM-5 | 19 | 1000 | 240 | 31.1 | <1 | 8.6 | 15.2 | 28.6 | 83.5 | 16.5 |
| xylitol | ZSM-5 | 19 | 1000 | 240 | 47.5 | <1 | 7.2 | 12.8 | 37.5 | 105.0 | 0.0 |
| glucose | ZSM-5 | 19 | 1 | 240 | 14.9 | <1 | 12.0 | 13.3 | 38.9 | 79.1 | 20.9 |
| glucose | ZSM-5 | 19 | 5 | 240 | 23.6 | <1 | 8.5 | 10.5 | 35.6 | 78.2 | 21.8. |
| glucose | ZSM-5 | 19 | 50 | 240 | 29.4 | <1 | 6.6 | 9.0 | 34.1 | 79.1 | 20.9 |
| glucose | ZSM-5 | 9 | 1000 | 240 | 27.2 | 2.8 | 11.0 | 13.6 | 32.3 | 86.9 | 13.1 |
| glucose | ZSM-5 | 4 | 1000 | 240 | 22.9 | 8.2 | 9.3 | 11.4 | 43.6 | 95.4 | 4.6 |
| glucose | ZSM-5 | 2.3 | 1000 | 240 | 16.5 | 13.6 | 7.3 | 8.7 | 41.7 | 87.8 | 12.2 |
| glucose | ZSM-5 | 1.5 | 1000 | 240 | 13.2 | 14.9 | 6.3 | 7.1 | 43.9 | 85.3 | 14.7 |
| glucose | Silicalite | 19 | 1000 | 240 | 6.5 | 12.3 | 5.6 | 6.1 | 69.4[a] | 30.6 | |
| glucose | $SiO_2$—$Al_2O_3$ | 19 | 1000 | 240 | 0.6 | 1.5 | 4.5 | 4.3 | 89.1[a] | 10.9 | |
| glucose | β-Zeolite | 19 | 1000 | 240 | 4.3 | 1.1 | 10.5 | 7.8 | 76.3[a] | 23.7 | |
| glucose | Y-Zeolite | 19 | 1000 | 240 | 1.1 | 1.8 | 5.3 | 5.3 | 86.5[a] | 13.5 | |

[a]Coke yield was estimated by mass balance

Example 3

In accordance with results summarized above, xylitol and xylose can be converted into thermally stable compounds by catalytic pyrolysis without significant coke formation (see Table 2). Catalyst addition to the pyrolysis process significantly decreases coke formation and increases the conversion to thermally stable products. Five different catalysts were tested for catalytic pyrolysis of xylitol including: silica alumina ($SiO_2$—$Al_2O_3$ Grace-Davison 3125), tungstated-zirconium ($WO_x/ZrO_2$ MEI X201251), sulfated-zirconium ($SO_x/ZrO_2$ MEI X20880), Pt-silica-alumina (Pt/$SiO_2$—$Al_2O_3$ prepared according to Huber et al) and ZSM-5 (silica to alumina molar ratio of 35 WR Grace). The catalyst structure greatly changes the product selectivity, and high yields (50%) of aromatic compounds (which could be used as gasoline fuel additives) can be produced with a ZSM-5 catalyst. The system employed detects thermally stable products versus thermally unstable compounds which decompose under GC conditions. Notably, xylose produces furfural with a higher selectivity (55%) than when xylitol is the feed.

Table 2 outlines the results for catalytic pyrolysis of xylitol in the pyroprobe-GCMS system. The reaction conditions for these experiments were as follows: Temperature, 600° C.; Ramping Rate, 1000° C./s; Reaction Time, 60 s, Xylitol to Catalyst Weight Ratio, 0.18; Xylitol added to catalyst as a physical mixture ground to Mesh Size between 60-120; Inert gas, 1 atm of He unless otherwise noted.

Example 5

Lignin and lignin-derived compounds can also be converted into fluid aromatic compounds by catalytic pyrolysis, in accordance with this invention (Tables 3 and 4). Pyrolysis of organosolv lignin primarily produces benzyl phenyl ether (BPE), ethanol, methanol, CO and $CO_2$. Catalyst pyrolysis increases the conversion to thermally stable products by 3 to 10 times (compared to pyrolysis without catalysts) with $SiO_2$—$Al_2O_3$ and ZSM-5 respectively. Organosolv lignin is a lignin product from the organosolv pulping process, and similar results can be anticipated from other solid compounds comprising lignin. These experiments show how catalysts can significantly change the products and reactivity of lignin-

TABLE 2

Catalytic pyrolysis of xylitol in the pyroprode-GCMS system.

| Catalyst | Conversion (wt %)[4] Liquid + Gas | Conversion (wt %)[4] Solid | Conversion (carb %)[5] Stable Comp. | Carbon Selectivity (%)[6] Furan | Carbon Selectivity (%)[6] Methyl Furan | Carbon Selectivity (%)[6] Furfural | Carbon Selectivity (%)[6] Acetald. | Carbon Selectivity (%)[6] $CO_2$ | Carbon Selectivity (%)[6] CO | Carbon Selectivity (%)[6] Arom.[7] |
|---|---|---|---|---|---|---|---|---|---|---|
| None[1] | 65 | 35 | 1 | 10 | 2 | 20 | 41 | 8 | 18 | <1 |
| $SiO_2$—$Al_2O_3$ | 95 | 5 | 12 | 27 | 7 | 7 | 25 | 22 | 13 | <1 |
| $SiO_2$—$Al_2O_3$[2] | | | — | 2 | 1 | 55 | 5 | 13 | 24 | <1 |
| Pt/$SiO_2$—$Al_2O_3$ | 67 | 33 | 25 | 12 | 3 | 1 | 15 | 18 | 50 | <1 |
| Pt/$SiO_2$—$Al_2O_3$ with $H_2$[3] | 86 | 13 | 32 | 27 | 13 | 2 | <1 | 14 | 45 | <1 |
| $WO_x$/$ZrO_2$ | 99 | 1 | 13 | 30 | 13 | 12 | 19 | 16 | 10 | <1 |
| $SO_x$/$ZrO_2$ | 92 | 8 | 11 | 30 | 12 | 7 | 7 | 34 | 9 | <1 |
| ZSM-5 | 67 | 33 | | <1 | <1 | <1 | <1 | 11 | 19 | 70 |

[1]1.08 mg of xylitol were used for this experiment. Xylitol was ground to mesh size of between 60-120.
[2]Xylose was the feed for this experiment
[3]This experiment was done in an atmosphere of hydrogen to see the effect of hydrogen.
[4]Conversion based on weight change.
[5]This conversion only reports the thermally stable compounds defined as products that can be analyzed with our current GCMS system.
[6]The selectivity is on a per carbon basis and only includes thermally stable compounds identified with GCMS.
[7]The aromatic products include: Benzene, Toluene, Ethyl Benzene, Xylenes, Naphthalene, Methyl-Naphthalene, Dimethyl-Naphthalene, Ethyl-Naphthalene, Hydrindene, Methyl-Hydrindene, and Dymethyl-Hydrindene.

Example 4

Metal addition to silica-alumina shifted the selectivity towards CO, showing that metals can influence the reaction chemistry. Such results suggest that by adding different amounts of metal to the catalysts the rate of hydrogen producing reactions and hydrogen transfer reactions can be increased. Catalytic hydropyrolysis (catalytic pyrolysis with hydrogen rather than He) decreased coke formation on the catalyst, illustrating yet another embodiment. These preliminary positive results show that catalytic pyrolysis can produce a range of products including aromatics which could be used as a gasoline or jet fuel blend. This aromatic blend can be produced from a variety of feedstocks over the ZSM-5 catalyst with similar product selectivity. (See, e.g., FIGS. 1A-1B.)

derived feeds in the pyrolysis process. A major product formed from organosolv lignin is BPE, and Table 3 shows results for catalytic pyrolysis of BPE: Benzene, phenol, toluene and other aromatic compounds. The catalytic pyrolysis process can be modified to produce benzene, phenol, toluene and other aromatic compounds directly from solid lignin streams. Benzene and Toluene can be added directly in gasoline, whereas phenol is a valuable commodity chemical.

Table 3 outlines the results from the catalytic pyrolysis of organosolv lignin (Aldrich) in the pyroprobe-GCMS system. The reaction conditions were as follows: Temperature, 600° C.; Ramping Rate, 1000° C./s; Reaction Time, 60 s; Lignin to Catalyst Weight Ratio, 0.18; Lignin added to catalyst as a physical mixture ground to Mesh Size between 60-120; Inert gas, 1 atm of He.

TABLE 3

Catalytic pyrolysis of organosolv lignin in pyroprobe-GCMS system

| | | Selectivity (%)[3] | | | | | | | |
|---|---|---|---|---|---|---|---|---|---|
| Catalyst | Conv. (% C)[1] | Ethanol | Methanol | CO | $CO_2$ | Methyl guaiacol | Benzyl phenyl ether | Xyl.[2] | Hydroxyphenyl) |
| None | 3.61 | 5.27 | 9.81 | 9.20 | 5.40 | 4.66 | 50.97 | 0.00 | — |
| $SiO_2$—$Al_2O_3$ | 9.04 | 10.73 | 13.49 | 16.85 | 7.82 | — | 43.48 | 0.00 | 3.03 |
| ZSM-5 | 37.41 | 0.21 | 0.36 | 9.06 | 2.42 | — | 72.91 | 6.06 | 6.19 |

[1]Conversion based on thermally stable compounds only.
[2]Xylene includes meta- and para-xylene.
[3]Other products observed in low selectivity, but not reported here include diphenylmethane, 1,2-diphenylethane, guaiacol, acetic acid, furfuraldehyde and toluene.

Table 4 outlines the results from the catalytic pyrolysis of benzyl-phenyl ether (BPE) in the Pyroprobe-GCMS system. The reaction conditions were as follows: Temperature, 600° C.; Ramping Rate, 1000° C./s; Reaction Time, 60 s; Lignin to Catalyst Weight Ratio, 0.18; Lignin added to catalyst as a physical mixture ground to Mesh Size between 60-120; Inert gas, 1 atin of He.

TABLE 4

Catalytic pyrolysis of benzyl-phenyl ether (BPE) in Pyroprobe-GCMS system.

| | | Selectivity (%)[3] | | | | | |
|---|---|---|---|---|---|---|---|
| Catalyst | Conv. (% C)[1] | Benzene | Phenol | Toluene | Biphenyl-methane[2] | 1,2-diphenyl ethane | Methyl phenol |
| None | 14.33 | 4.16 | 80.02 | 8.91 | 0.00 | 4.72 | 0.00 |
| $SiO_2$—$Al_2O_3$ | 63.57 | 37.88 | 36.19 | 10.60 | 4.85 | 6.08 | 3.77 |
| ZSM-5 | 53.34 | 38.62 | 42.87 | 6.48 | 4.88 | 3.79 | 2.51 |

[1]Conversion is based on thermally stable compounds only.
[2]Methyl phenol includes (2,3 and 4)-methylphenols
[3]Other products with low selectivity include benzyl alcohol and benzaldehyde.

Example 6

In accordance with certain embodiments and by comparison with the prior art, biomass was pyrolysed to condensable vapors which were converted over the catalyst (in situ) at the same temperature in the same reaction chamber. A second stage, as described in U.S. Pat. Nos. 7,241,323 and 5,504,259, was eliminated from the process. The benefit of a one stage process is two fold: less energy is used than when the fluid product is condensed and later upgraded (all chemistry happens at the same temperature), and the condensable vapors do not have the chance to polymerize or otherwise degrade during the transfer to a second upgrading stage.

Example 7

In general, fluid fuel product compositions of the prior art are not specified. While the literature reports lowered oxygen content, it does not disclose specific molecular fuel components. Illustrating a range of embodiments of the type described herein, a ZSM-5 catalyst in a fixed bed reactor produced a fluid consisting almost entirely of aromatic compounds. Oxygen was removed from the biomass in the form of water, CO, and $CO_2$. Specifically, aromatics quantified in the fuel included: benzene, toluene, xylenes, ethyl-benzene, ethyl-methyl-benzene, trimethyl-benzene, indane, methyl-indane, naphthalene, methyl-naphthalene, and dimethyl-naphthalene. Such a mix of aromatics could be used as a high octane fuel additive. All of the aromatics are above 100 octane with the exception of naphthalene (90 octane). See Table 5, below.

TABLE 5

Properties of the quantified aromatic species.

| Compound | Boiling Point (° C.) | Research octane number (RON) | Motor octane number (MON) |
|---|---|---|---|
| Benzene | 84.35 | 98 | 90 |
| Toluene | 112.29 | 124 | 112 |
| Ethyl-Benzene | 135.17 | 124 | 107 |
| o-Xylene | 140.15 | 120 | 102 |
| m-Xylene | 140.15 | 145 | 124 |
| p-Xylene | 140.15 | 146 | 126 |
| Ethyl-methyl Benzene | 163.03 | 126-155 | 112-138 |
| Tri-methyl Benzene | 168.01 | 118-170 | 104-136 |
| Indan | 174.44 | 161 | 140 |
| Naphthalene | 199.91 | not reported | 90 |
| Methyl-Naphthalene | 227.77 | 123-127 | 114-116 |

Source: Knocking characteristics of pure hydrocarbons (Research Project 45). American Society of Testing Materials (ASTM), Special Technical Publication No. 225. Philadelphia, PA, 1958

As demonstrated above, high quality aromatic fuel/additives can be produced directly from solid biomass feedstocks by catalytic pyrolysis in a single catalytic reactor at short residence times. Through an understanding of the reaction chemistry, catalyst, and apparatus/reactor design, catalytic pyrolysis can be used to efficiently generate fluid biofuels from a range of lignocellulosic biomass resources.

Example 8

Figure 6A:
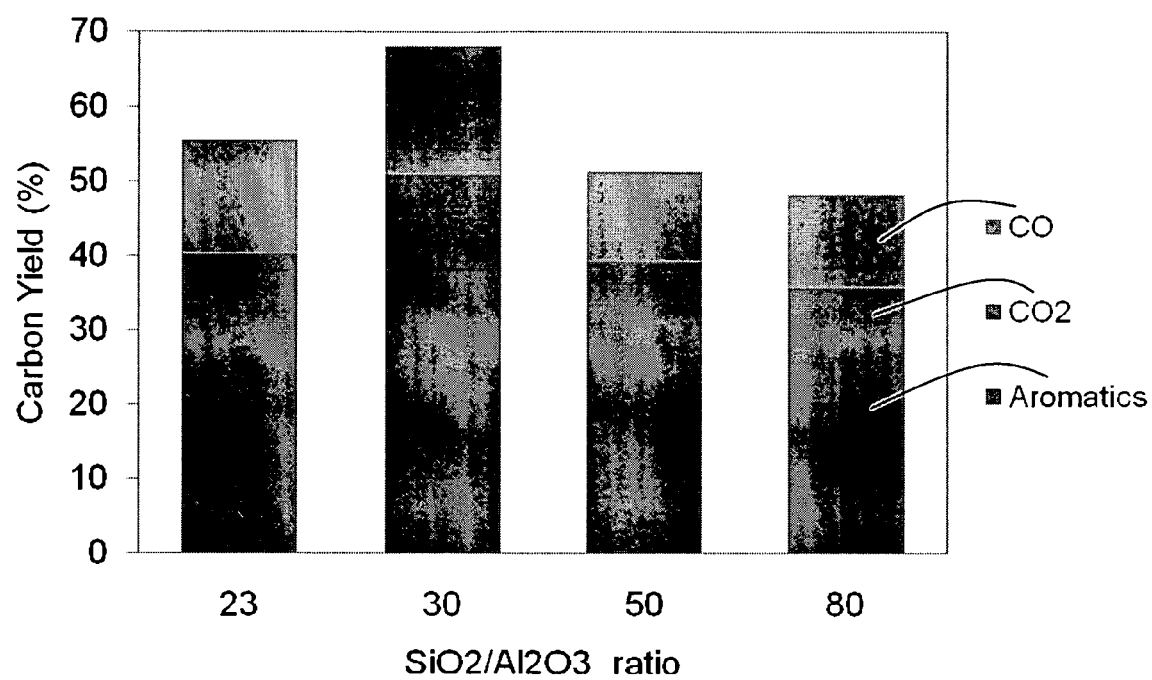
FIGS. 6A-6B are plots of (A) carbon yields for various silica to alumina molar ratios in the catalyst and (B) aromatic selectivity for feeds of benzene (Ben.), toluene (Tol.), ethyl-benzene and xylenes (E-Ben., Xyl.), methyl-ethyl-benzene and trimethyl-benzene (m,e-Ben., tmBen.), indanes (Ind.), and naphthalenes (Nap.) for various silica to alumina molar ratios in the catalyst according to one set of embodiments.
Figure 6B:
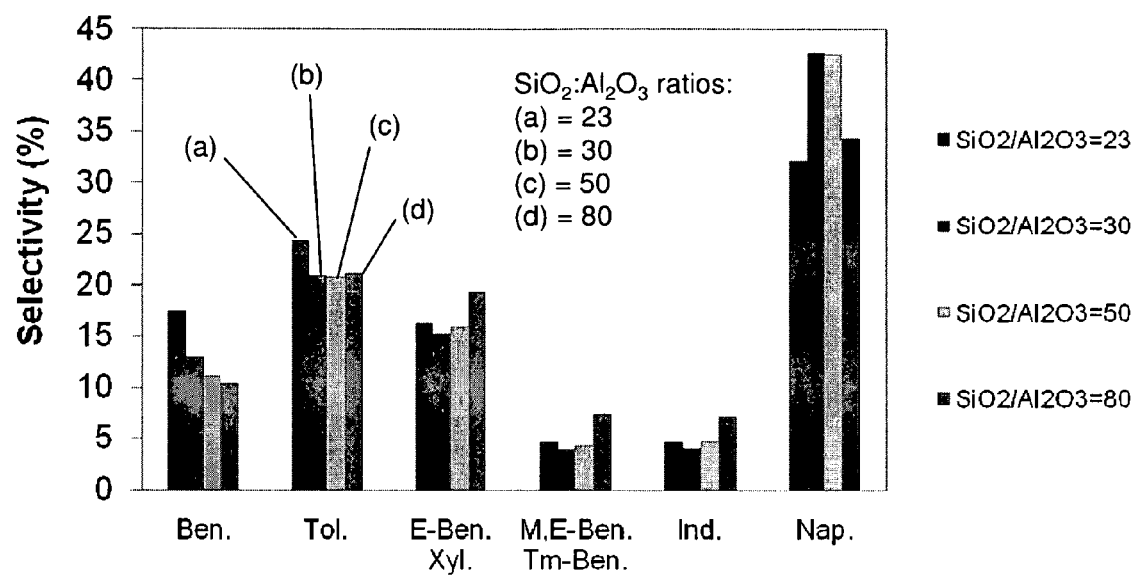

The effect of varying the silica to alumina molar ratio of the catalyst was also investigated. The conditions for these experiments were as follows: catalyst to feed mass ratio, 19; catalyst, ZSM5; nominal heating rate, 1000° C. s$^{-1}$; reaction temperature, 600° C.; reaction time (residence time of feed), 240 s. Glucose was used as the hydrocarbonaceous feed for these experiments. FIGS. 6A-6B show the product selectivity for catalytic pyrolysis of glucose as a function of silica to alumina molar ratio. As shown in FIG. 6A, the use of catalyst with a silica to alumina molar ratio of 30 produced the highest amount of aromatic product compared to the use of catalysts with silica to alumina molar ratios of 23, 55, or 80. As shown in FIG. 6B, use of catalysts having different molar ratios of silica to alumina can produce higher yields of selective compounds. For example, to produce higher yields of napthalenes, a silica to alumina molar ratio of about 30 or 50 can be used.

Example 9

This example illustrates the effect of metal impregnation in the catalyst on product yields. Impregnation of ZSM-5 (silica to alumina molar ratio of 30, Zeolyst) pores with metals shifted the product selectivity toward CO and $CO_2$, showing that metals can influence the reaction chemistry. Not wishing to be bound by any theory, the metals may increase decarbonylation and/or decarboxylation reaction rates. The following metals were tested: Cu, Mn, Fe, Co, Ni, Zn, Ga, and Pt. Table 6 summarizes the results obtained for the catalytic pyrolysis of glucose on metal incorporated ZSM-5 in the pyroprobe-GCMS system. Two different methods were employed for metal addition to ZSM-5: wet impregnation and ion exchange. Catalysts impregnated using the ion exchange method produced higher yields of aromatics and lower yields of coke compared to catalysts impregnated using the wet impregnation method.

TABLE 6

Summary of metal addition on ZSM-5

| Catalyst | Metal loadiing (wt %) | Preparation Method | Aromatic yield (C %) | Oxygenate yield (C %) | $CO_2$ yield (C %) | CO yield (C %) | Coke yield (C %) |
|---|---|---|---|---|---|---|---|
| Cu-ZSM-5 | 6.2 wt % | Solid state Ion Exchange | 8.1 | <1 | 24.1 | 33.6 | 31.4 |
| Mn-ZSM-5 | 5 wt % | Wet impregnation | 11.9 | <1 | 18.2 | 25.5 | 45.0 |
| Mn-ZSM-5 | 5 wt % | Ion Exchange | 23.0 | <1 | 5.8 | 22.5 | 34.1 |
| Fe-ZSM-5 | 5 wt % | Wet impregnation | 20.9 | <1 | 11.5 | 24.8 | 41.0 |
| Co-ZSM-5 | 5 wt % | Wet impregnation | 12.7 | <1 | 28.0 | 44.5 | 19.6 |
| Ni-ZSM-5 | 5 wt % | Wet impregnation | 7.2 | <1 | 34.7 | 47.1 | 12.0 |
| Zn-ZSM-5 | 5 wt % | Wet impregnation | 23.7 | <1 | 14.7 | 23.7 | 37.9 |
| Zn-ZSM-5 | 5 wt % | Ion Exchange | 32.9 | <1 | 9.9 | 29.2 | 30.7 |
| Ga-ZSM-5 | 5 wt % | Wet impregnation | 28.5 | <1 | 6.0 | 22.2 | 48.0 |
| Ga-ZSM-5 | 5 wt % | Ion Exchange | 33.3 | <1 | 7.6 | 30.4 | 23.2 |
| Pt-ZSM-5 | 5 wt % | Wet impregnation | 17.0 | <1 | 15.6 | 35.1 | 25.2 |

Catalyst pore sizes also affected aromatic yield. Table 7 includes carbon yield data from the catalytic pyrolysis of glucose over several different frameworks of zeolites. Not wishing to be bound by any theory, it may be desirable to use zeolite catalysts with pore sizes large enough to allow the diffusion of oxygenated intermediate molecules (e.g., methyl furfural, which has kinetic diameter of 5.9 Angstroms) into the zeolite framework. It may also be desirable to use zeolite catalysts with pore sizes sufficiently small to selectively produce aromatics (<6.3 Angstroms). Table 7 shows that ZK-5 produced no aromatics while Y-zeolite produced primarily coke. Catalysts with pore sizes closest to that of ZSM-5 (5.6 Å) produced the most aromatic yield.

TABLE 7

Summary of different frameworks on Catalytic pyrolysis

| Zeolite | IZA code | Structure | Dimension | Ring Size | Pore Size | Aromatic yield (C %) | Oxygenate yield (C %) | $CO_2$ yield (C %) | CO yield (C %) | Coke yield (C %) |
|---|---|---|---|---|---|---|---|---|---|---|
| SAPO-34 | CHA | rhombohedral | 3 | 8 | 3.8 × 3.8 | 0.3 | 8.6 | 9.5 | 21.7 | 68.8 |
| ZK-5 | KFI | cubic | 3 | 8, 8 | 3.9 × 3.9 | 0.0 | 1.8 | 18.1 | 25.2 | 46.4 |
| Ferrierite | FER | orthorhombic | 2 | 10, 8 | 4.2 × 5.4 3.5 × 4.8 | 0.0 | 3.4 | 8.8 | 27.7 | 34.6 |
| ZSM-23 | MTT | orthorhombic | 1 | 10 | 4.5 × 5.2 | 7.0 | 1.2 | 4.8 | 19.8 | 43.4 |
| SSZ-20 | TON | orthorhombic | 1 | 10 | 4.6 × 5.7 | 7.4 | 2.8 | 3.7 | 15.9 | 34.0 |
| SSZ-41 | VET | tetragonal | 1 | 12 | 5.9 × 5.9 | 5.2 | 0.6 | 2.6 | 7.7 | 65.5 |
| ZSM-12 | MTW | orthorhombic | 1 | 12 | 5.6 × 6.0 | 2.5 | 2.8 | 2.5 | 8.2 | 79.4 |
| SSZ-55 | ATS | orthorhombic | 1 | 12 | 6.5 × 7.5 | 3.4 | <1 | 5.6 | 21.4 | 83.7 |
| β-zeolite | BEA | tetragonal | 3 | 12, 12 | 6.6 × 6.7 5.6 × 5.6 | 4.3 | 1.1 | 10.5 | 7.8 | 67.0 |
| Y-zeolite | FAU | cubic | 3 | 12, 12 | 7.4 × 7.4 | 1.6 | <1 | 7.6 | 25.3 | 85.0 |

Figure 11:
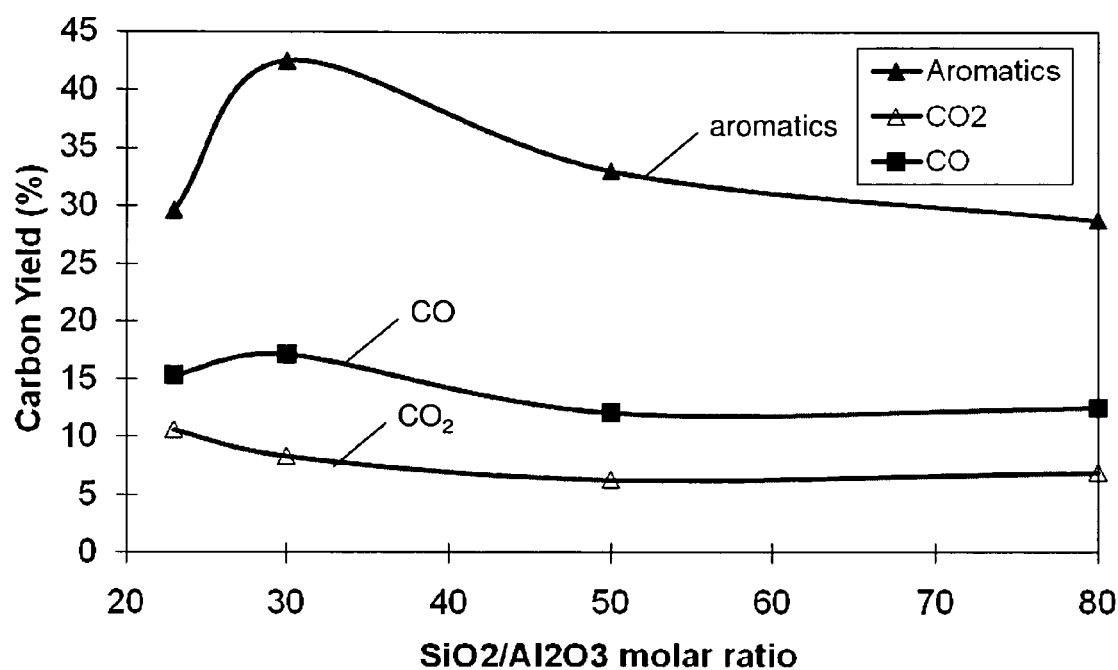
FIG. 11 is a plot of carbon yield of CO (■), aromatics (▲), and $CO_2$ (Δ) as a function of silica to alumina molar ratio for a catalytic pyrolysis of glucose with ZSM-5, according to one set of embodiments.

The density and strength of acid sites in the catalysts also had an effect on aromatic production. FIG. 11 is a plot of carbon yield from the pyrolysis of glucose using ZSM-5 catalysts with different silica to alumina molar ratios ($SiO_2/Al_2O_3$=23, 30, 50, and 80, Zeolyst). ZSM-5 ($SiO_2/Al_2O_3$=30) produced the maximum yield of aromatics at 600° C. with a 1000° C./s ramp rate.

Example 10

Naturally occurring biomass was also used as a feedstock in some experiments to produce fluid aromatics by catalytic pyrolysis. Table 8 outlines the results for catalytic pyrolysis of naturally occurring biomass in the pyroprobe-GCMS system. Pyrolysis of wood, sugarcane (Brazil and Hawaii) and corn stover over ZSM-5 (Si/Al=60 WR Grace) produced aromatics, CO and $CO_2$. The aromatic yields produced using these feedstocks were comparable to that of glucose and cellulose. Such results suggest that catalytic pyrolysis can be used with naturally occurring biomass feedstocks.

TABLE 8

Catalytic pyrolysis of naturally occurring biomass in the pyroprobe-GCMS system

| Feed | Catalyst | Catalyst to feed mass ratio | Heating rate (° C./s) | Reaction time (s) | Aromatic yield (%) | Oxygenate yield (%) | $CO_2$ yield (%) | CO yield (%) |
|---|---|---|---|---|---|---|---|---|
| Wood | ZSM-5 | 19 | 1000 | 240 | 26.4 | <1 | 4.9 | 11.7 |
| Sugarcane (Sao Paulo) | ZSM-5 | 19 | 1000 | 240 | 28.3 | <1 | 8.0 | 12.2 |
| Sugarcane (Leandro, Brazil) | ZSM-5 | 19 | 1000 | 240 | 29.9 | <1 | 6.6 | 12.9 |
| Sugarcane (Puunene, HI) | ZSM-5 | 19 | 1000 | 240 | 26.6 | <1 | 5.6 | 11.9 |
| Corn Stover | ZSM-5 | 19 | 1000 | 240 | 21.4 | <1 | 6.8 | 10.1 |

Example 11

This example describes the use of a fixed bed, flow reactor system. In this example, a 0.5-inch diameter quartz tubular reactor (approximately 2 inches long) was used. The reactor was loaded with 50 mg of ZSM-5 catalyst (ZEOLYST, CBV 3024E, $SiO_2/Al_2O_3$=30) to produce a fixed bed, which was supported by quartz wool and quartz beads. The quartz reactor was held in a temperature-controlled furnace (furnace: Lindberg, 55035A; temperature controller: Omega, CN96211TR) at 600° C. The temperature of the reactor was monitored by a thermocouple inserted through a quartz inner tube to the top surface of the packed bed.

The feedstock for this example was furan (Sigma-Aldrich, 99%). During operation, helium (ultra high purity, Airgas) was used as a carrier gas, and its flow rate was controlled by a mass flow controller (controller: Brooks, SLA5850SIBAB1-C2A1; controlling box: Brooks, 0154CFD2B31A). Liquid feedstock (furan) was introduced into the carrier gas by a syringe pump (KD Scientific, KDS 100) and was quickly vaporized. The vaporized feed was transported to the reactor. The temperature of the reactor was 600° C., under a He atmosphere with a furan partial pressure 5.7 torr.

Products flowed from the reactor to a condenser placed in a dry ice-acetone bath. The condenser was maintained at a temperature of around −55° C. and was used to condense products with relatively high boiling points. Gas products were collected in gas-sampling bags. Liquid and gas products were analyzed using GC-FID (Shimadzu 2010).

The amount of carbon on the catalyst was determined during catalyst regeneration. During regeneration, CO was converted to $CO_2$ by a copper converter. The $CO_2$ was trapped by ascarite (Sigma-Aldrich, 5-20 mesh). The amount of carbon on the partially deactivated catalyst was calculated by measuring the weight change of the $CO_2$ trap.

Figure 12:
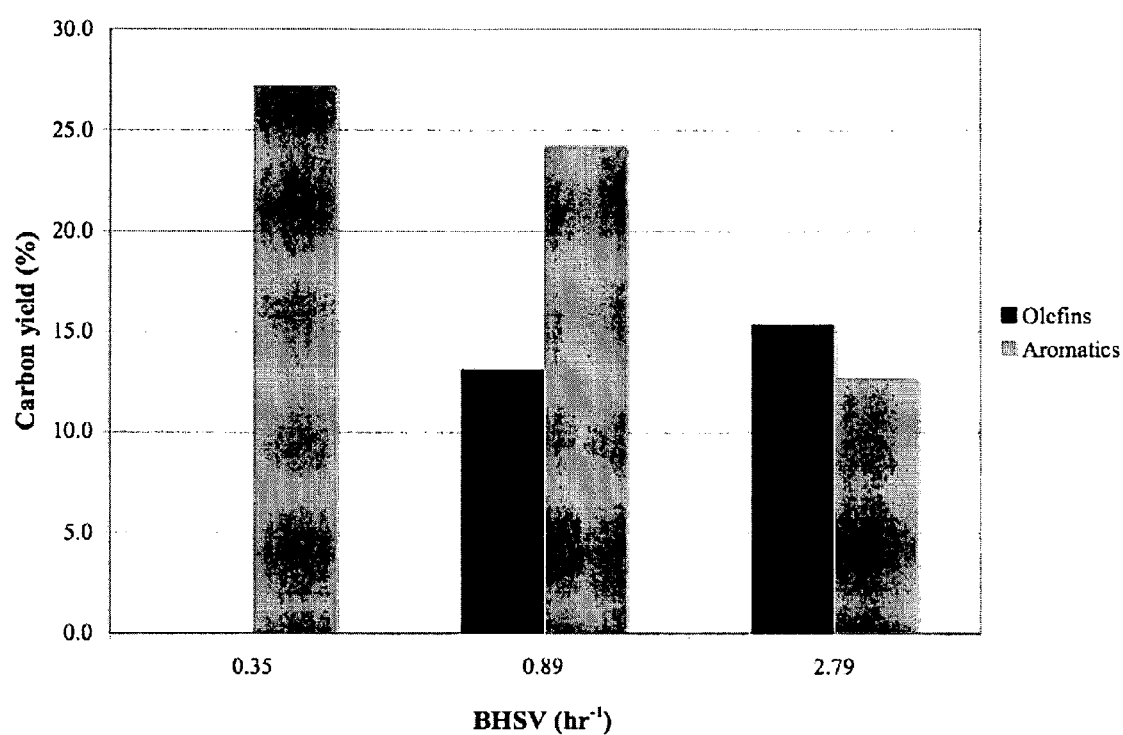
FIG. 12 is a graph outlining the carbon yields of olefins and aromatics as a function of space velocity for one set of embodiments.

As shown in FIG. 12, the yield of olefins was affected by the mass-normalized space velocity ($hr^{-1}$) of the furan. The mass-normalized space velocity was calculated as the mass flow rate of furan (g/hr) divided by mass of catalyst (g). The carbon yield was calculated by dividing the moles of the carbon in a product by the moles of carbon fed to the reactor. The types of olefins produced included ethene and propene, and a trace amount of butene was also detected. For a space velocity of 0.35 hr$^{-1}$, no olefins were detected. However, at a space velocity of 2.79 hr$^{-1}$, the yield of olefins rose to 15%. On the contrary, the yield of aromatics, which was the second most abundant product, decreased as the space velocity increased (and as the residence time decreased).

Figure 13:
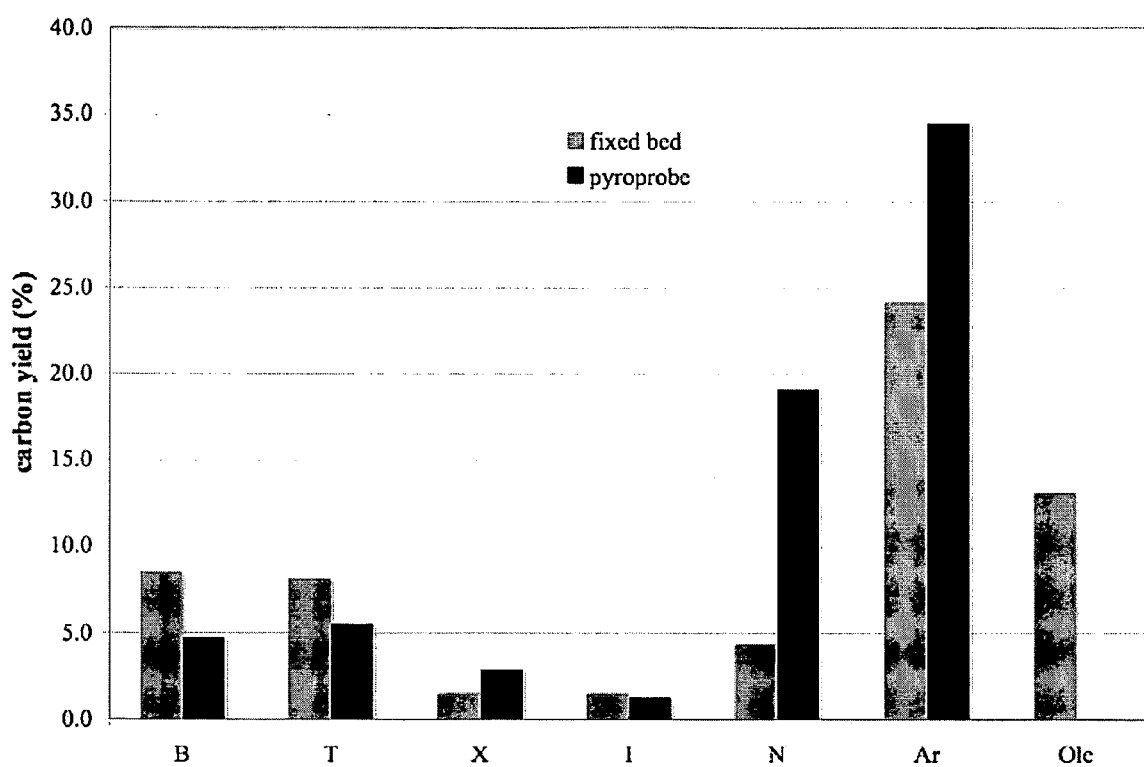
FIG. 13 is a graph illustrating the carbon yields of various compounds according to one set of embodiments.

FIG. 13 includes a plot comparing the carbon yields of each aromatic product and olefins obtained from furan conversion in the fixed-bed flow reactor and the pyroprobe. The reaction condition for the fixed-bed reactor were: reaction temperature, 600° C.; furan partial pressure, 5.7 torr; and space velocity 0.89 hr$^{-1}$. The reaction condition for the pyroprobe were: reaction temperature, 600° C.; catalyst to feed mass ratio, 19; and reaction time, 4 min. Both the fixed-bed and pyroprobe reactors used ZSM-5 catalyst. In the pyroprobe, olefins were not produced to a substantial degree. The pyroprobe experiments, however, yielded a large amount of naphthalene, and a relatively large amount of aromatics. The fixed bed reactor experiments yielded slightly higher amounts of valuable products (aromatics plus olefins). Benzene and toluene yields were also higher in the fixed bed reactor than in the pyroprobe. Ethylbenzene and trimethylbenzene (which are not shown in FIG. 13) were also detected in the pyroprobe experiments, but not to an appreciable extent in the flow reactor experiments.

Example 12

Figure 14:
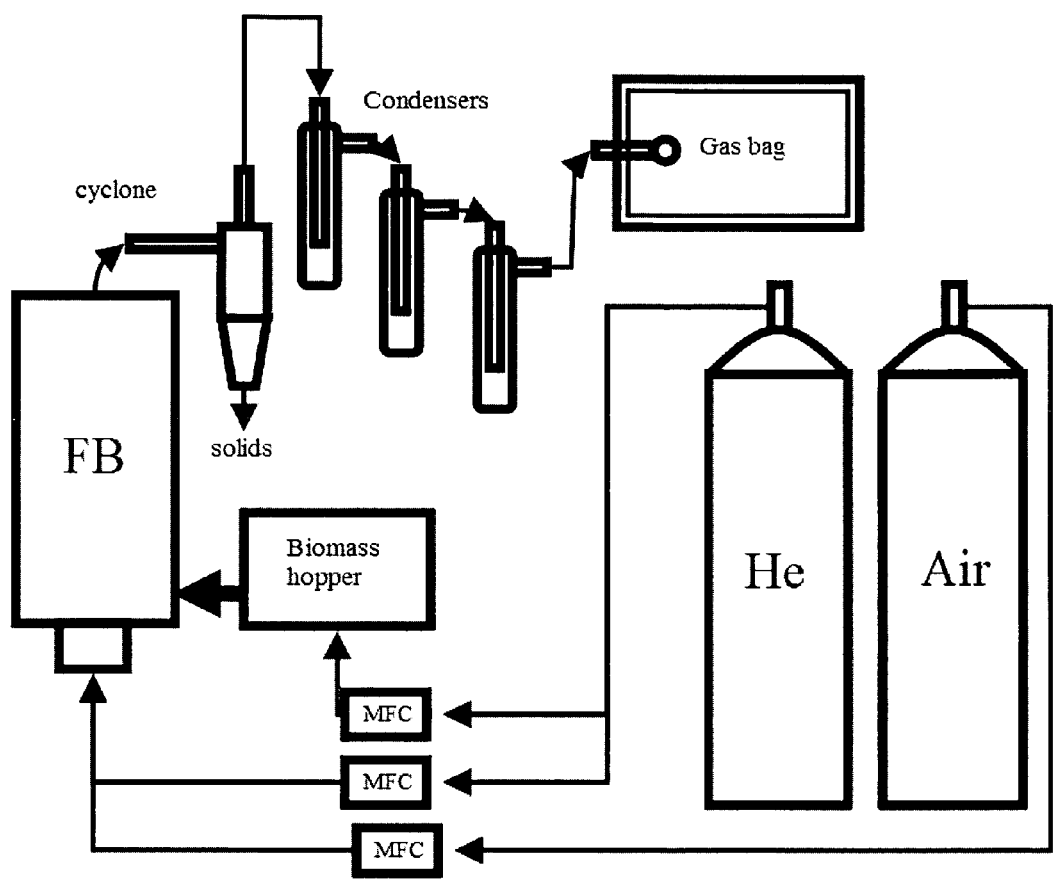
FIG. 14 is a schematic diagram of one set of embodiments in which a fluidized bed reactor is used.

In this example, a fluidized bed was used to convert solid biomass to hydrocarbons. FIG. 14 includes a schematic diagram of the fluidized bed system. The fluidized bed reactor was constructed using a 2 inch diameter, 316 stainless steel tube. The tube was 10 inches in length. A distributor plate made from a stacked 316 stainless steel mesh (300 mesh) was mounted within the reactor. The distributor plate served to support the catalyst bed. The reactor was loaded with 90 grams of ZSM-5 catalyst (Grace). Prior to operation, the catalyst was calcined in the reactor for 4 hr at 600° C. in 1200 mL min$^{-1}$ flowing air.

The catalyst was fluidized during operation of the reactor via a helium gas stream controlled by a mass flow controller. The fluidization gas flow rate was 1200 mL min$^{-1}$ at SATP. Solid biomass feedstocks of wood were injected by a stainless steel auger into the side of the reactor from a sealed feed hopper. The feed rate of the wood was 6 g hr$^{-1}$, yielding a mass-normalized space velocity of 0.07 hr$^{-1}$. To maintain an inert environment in the reactor, the hopper was swept with helium at a rate of 200 mL min$^{-1}$. Both the reactor and the fluidization gas were resistively heated to reaction temperature of 600° C.

During operation, product gases exited the top of the reactor and passed through a cyclone, operated at 450° C., where entrained solids were removed and collected. The vapor then passed through a condenser train. The first three condensers were operated at 0° C. in an ice bath, and the following three condensers were operated at −55° C. in a dry ice/acetone bath. The non-condensed vapors exiting the condenser train were collected in a tedlar gas sampling bag for GC/MS and GC/FID analysis. Liquids collected in the condensers were quantitatively removed after reaction with ethanol and analyzed with GC/MS and GC/FID.

Figure 15:
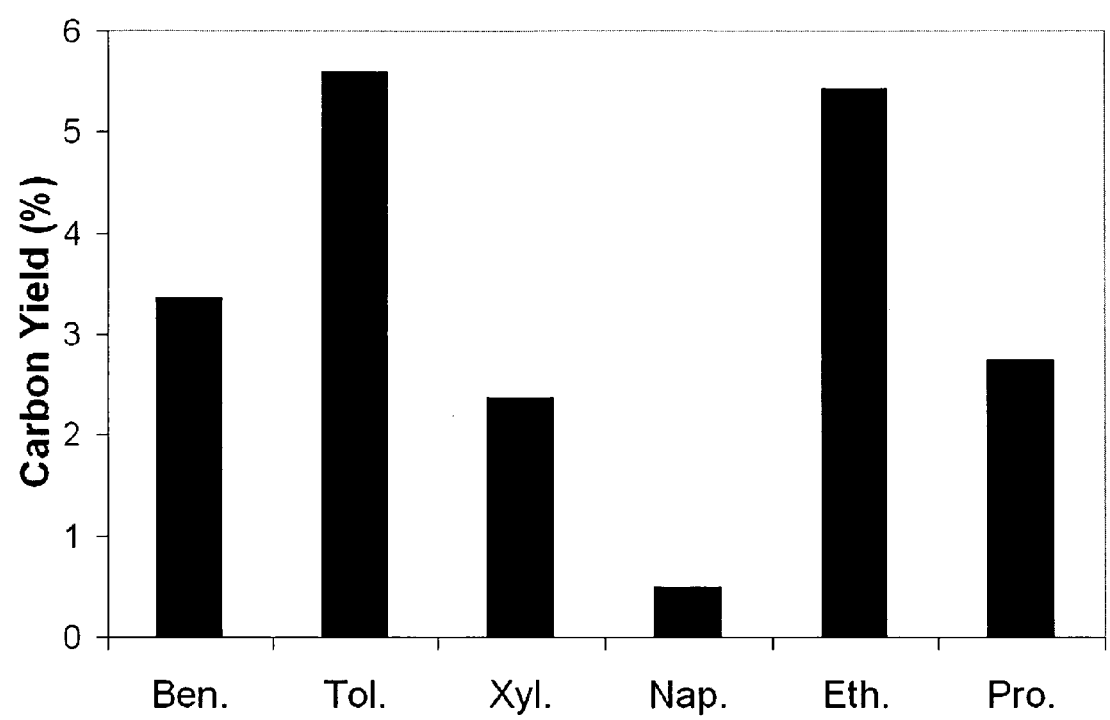
FIG. 15 is a plot outlining the product yield of aromatics and olefins for one set of embodiments.

The aromatic yields for the pyrolysis of wood with ZSM-5 catalyst in the fluidized bed reactor system are shown in FIG. 15. The quantified products in FIG. 15 include: benzene (Ben.), toluene (Tol.), xylene (Xyl.), naphthalene (Nap.), ethene (Eth.) and propene (Pro.). The yield of naphthalene was relatively low, and the primary products were benzene, toluene and xylene. In addition to aromatics, olefins such as ethene and propene were produced during catalytic pyrolysis in the fluidized bed reactor.

Figure 16A:
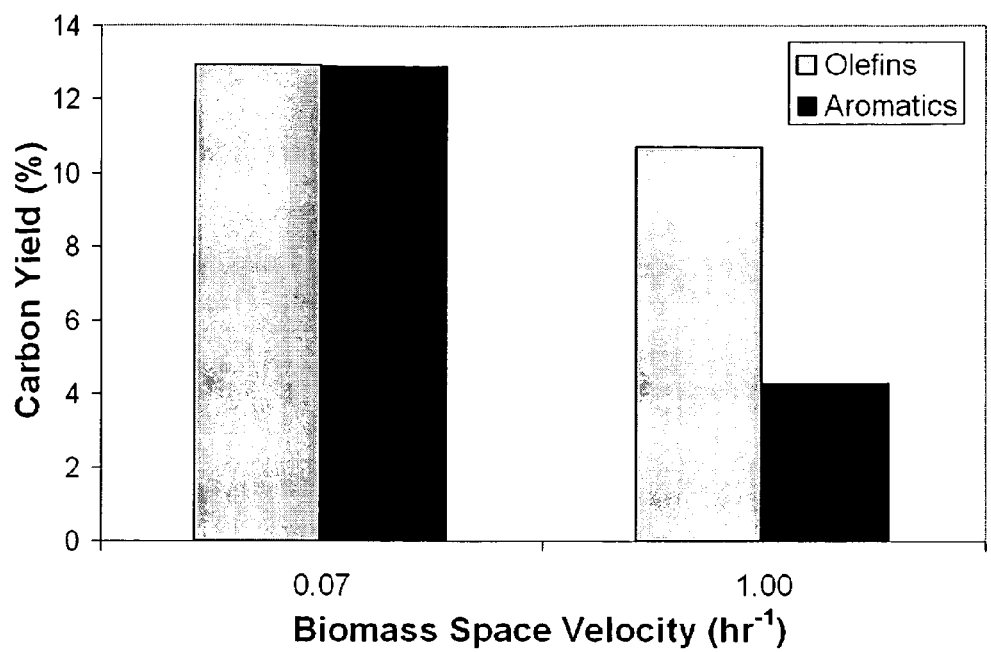
FIGS. 16A-16B include plots of olefin and aromatic yield and selectivity, respectively, as a function of space velocity, according to one set of embodiments.
Figure 16B:
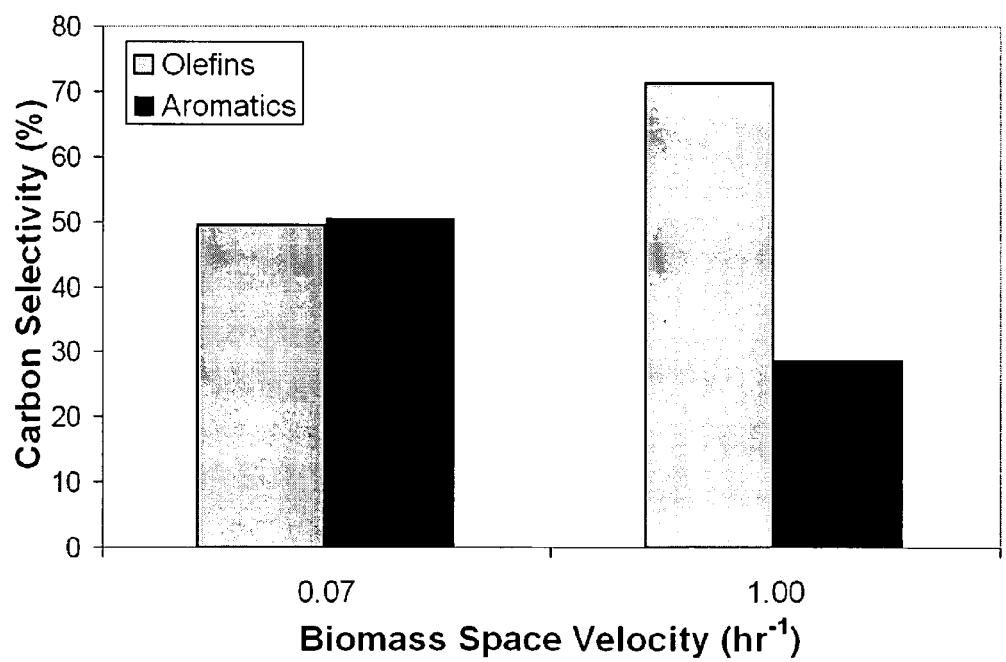

The selectivity for olefins and aromatics was adjusted by varying the mass-normalized space velocity of the biomass. Two different space velocities were tested in the fluidized bed reactor at a reactor temperature of 600° C. 30 g and 90 g charges of catalyst were used for the high and low biomass space velocity runs, respectively. Dry pine wood (80-120 mesh) feed was fed at 30 g hr$^{-1}$ and 6 g hr$^{-1}$ for the high and low biomass space velocity runs, respectively. The fluidization gas temperature was 600° C., with a fluidization gas flow rate of 12 mL min$^{-1}$ at SATP. The cyclone temperature was 450° C., and a ZSM-5 catalyst was used. As seen in FIGS. 16A-16B, the reaction is selective for olefin production at high space velocity while, at low space velocity, aromatic products are favored. The olefin products quantified included: ethene, propene, butane and butadiene. The aromatic products quantified included: benzene, toluene, xylene, ethyl-benzene, styrene and naphthalene.

Example 13

This example describes the use of a fixed bed reactor to test the effects of feeding olefins on the types and amounts of products formed during the catalytic pyrolysis of a hydrocarbonaceous feed material. A fixed bed, flow reactor system was built for biomass conversion. The flow rates of the carrier gases (described below) were controlled using mass flow controllers (controller: Brooks, SLA5850SIBAB1-C2A1; controlling box: Brooks, 0154CFD2B31A). Liquid feedstock was introduced into the carrier gas using a syringe pump (KD Scientific, KDS100) and was vaporized essentially immediately. The vapor feedstock was then carried into a quartz tubular reactor. The quartz reactor was held in a temperature-controlled furnace (furnace: Lindberg, 55035A; temperature controller: Omega, CN96211TR). The fixed catalyst bed in the reactor was supported by quartz wool and quartz beads. The temperature of the reactor was monitored using a thermocouple inserted through a quartz inner tube to the top surface of the packed bed. Products from the reactor were passed through a condenser placed in an ice-water bath to condense heavy liquid products. Gas products were collected in gas-sampling bags. Liquid and gas products were analyzed by gas chromatography (GC) employing a flame ionization detector (FID) using HP 7890 and Shimadzu 2014 instruments, respectively. Coke yield was determined by thermogravimetric analysis (TGA) (TA Instrument, SDT-Q600), assuming that weight loss was caused by removal of carbon.

Several experiments were conducted in which furan (Sigma-Aldrich, 99%) was reacted under He atmosphere in the flow reactor. ZSM-5 was used as the catalyst (ZEOLYST, CBV 3024E, SiO$_2$/Al$_2$O$_3$=30). Ethene (a.k.a. ethylene) and propene (a.k.a. propylene) were used as olefin sources, and were incorporated into the feed gas when tested. The following carrier gas compositions were tested: 100% helium, 98% helium/2% ethene, 99.8% helium/0.2% ethene, 98% helium/2% propene, and 99.8% helium/0.2% propene. Table 9 outlines the reaction conditions of each experimental test. During each test, the reaction temperature was kept at 600° C., the furan space velocity (WHSV) was 10.5 h$^{-1}$, the furan partial pressure was 6 torr, and the carrier gas flow rate was 200 mL/min.

TABLE 9

Reaction conditions

| Test | Feedstock | Carrier gas, 200 mL/min | Furan conversion (%) |
|---|---|---|---|
| 1 | Furan | He | 43 |
| 2 | Furan | 2% Ethene | 46 |
| 3 | Furan | 0.2% Ethene | 49 |
| 4 | Furan | 2% Propene | 49 |
| 5 | Furan | 0.2% Propene | 62 |

Figure 18:
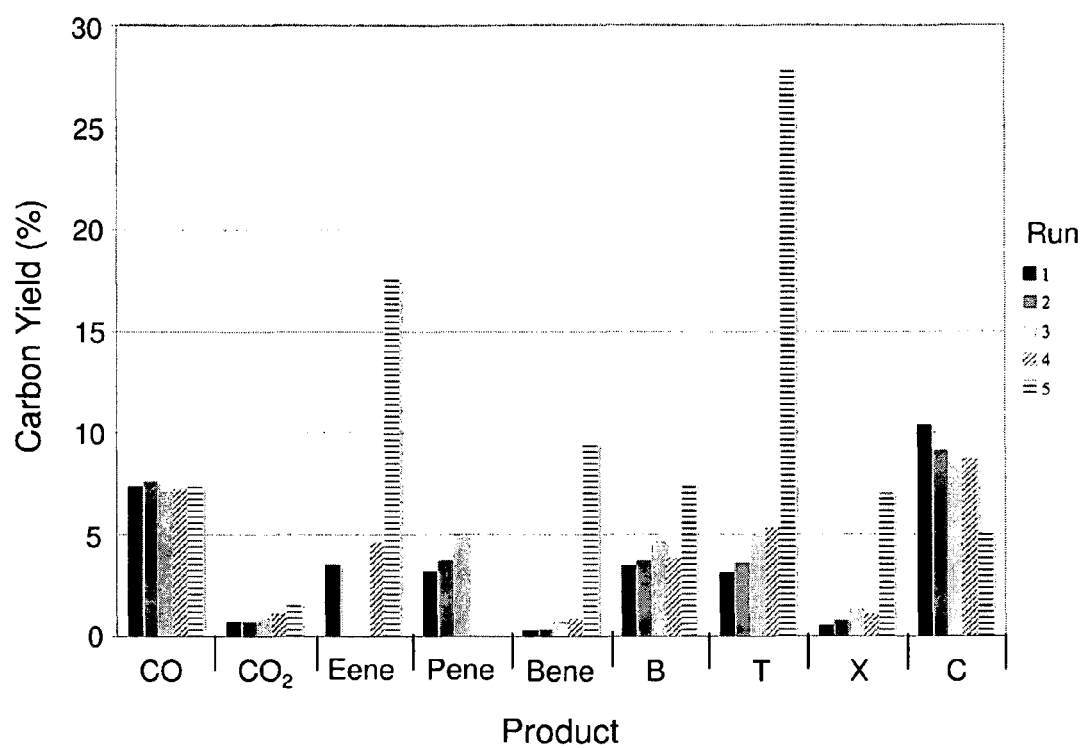
FIG. 18 includes a plot of carbon yield of various reaction products for multiple experimental runs, according to one set of embodiments.

FIG. 18 includes a plot of carbon yield (expressed as a percentage) for various products obtained from the catalytic conversion of biomass-derived feedstocks in the quartz tube flow reactor using ZSM-5 catalyst and the reaction conditions shown in Table 9. The following abbreviations are used in FIG. E1: Eene=Ethene, Pene=Propene, Bene=Butene, B=Benzene, T=Toluene, X=Xylene, C=coke. As shown in FIG. 18, aromatics and olefins were produced, and their carbon yields were affected by the composition of the feedstock. The carbon yield was defined as the moles of carbon in the product divided by the moles of carbon in the furan feed. The carbon yields of ethene and propene (in cases where mixtures were used as the carrier gas) are not shown in FIG. 18 because of their high values. Furan conversion is illustrated in Table 9.

Minor products (contributing less than 4% of the carbon yield) included styrene, benzofuran, indene, and naphthalene. With an increase in propene concentration in the carrier gas, the reaction was more selective for aromatics and light olefins, especially for ethene, butene, toluene, and xylene. Regarding Runs 2 and 3, the inclusion of ethene in the carrier gas also led to increased aromatics and light olefins production, although the effect was not as significant as that observed when propene was used. In addition, co-feeding ethene or propene increased the conversion of furan and decreased the amount of coke produced. Due to higher furan conversion, higher aromatic selectivity, and lower coke yield, it is evident that the incorporation of olefins in the feed stream (e.g., via recycle) can be beneficial for increasing the yield and selectivity of certain products in processes involving the conversion of biomass.

Example 14

Figure 19:
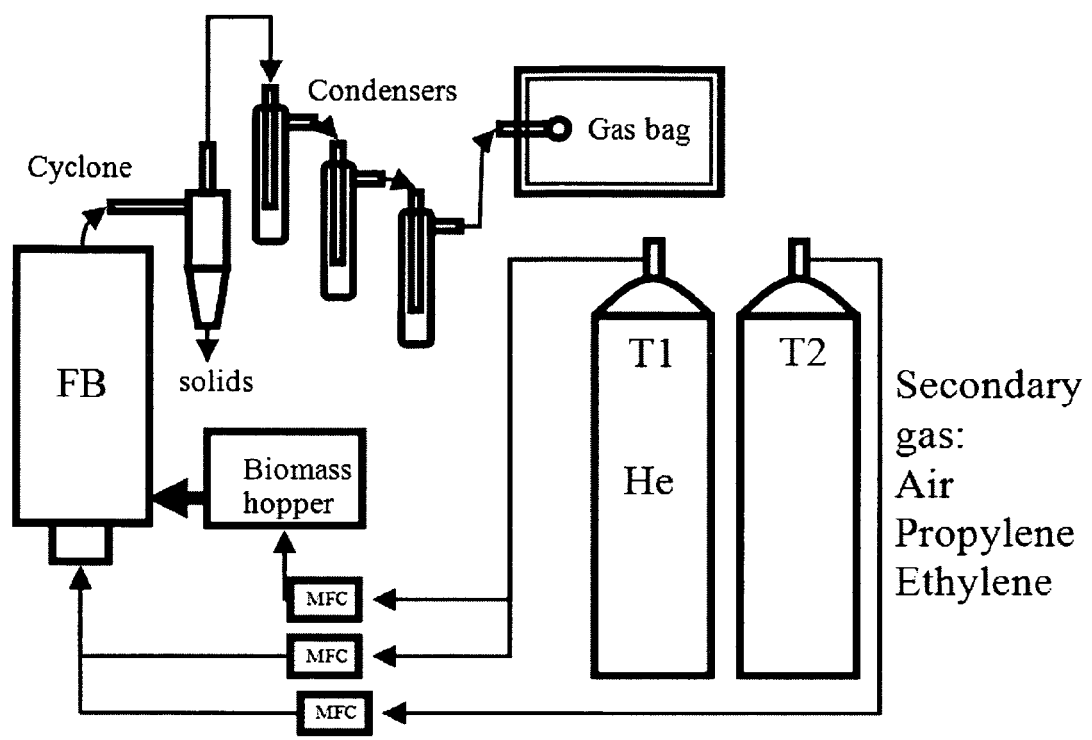
FIG. 19 includes an exemplary schematic diagram of a reactor system setup.

This example describes the use of a fluidized bed reactor to test the effects of feeding olefins on the types and amounts of products formed during the catalytic pyrolysis of a hydrocarbonaceous feed material. The fluidized bed reactor setup is illustrated in FIG. 19. The fluidized bed reactor comprised a 2-inch diameter, 10-inch tall, 316 stainless steel tube. Solid biomass feedstocks were injected into the side of the reactor from a sealed biomass hopper using a stainless steel auger. To maintain an inert environment in the reactor the hopper was swept with helium at a rate of 200 mL The catalyst bed was supported by a distributor plate made from stacked 316 stainless steel mesh (300 mesh). During the reaction, the catalyst was fluidized via a helium gas stream controlled by a mass flow controller. Both the reactor and the inlet gas stream were resistively heated to the reaction temperature.

During operation, product gases exited the top of the reactor and passed through a cyclone where entrained solids were removed and collected. The vapor was then passed through a condenser train. The first three condensers were operated at 0° C. in an ice bath, and the following three condensers were operated at −55° C. in a dry ice/acetone bath. The non-condensed vapors exiting the condenser train were collected in a Tedlar® gas sampling bag for gas chromatography/mass spectrometry (GC/MS) and GC/FID analysis. Liquids collected in the condensers were quantitatively removed after reaction with ethanol and analyzed using GC/MS and GC/FID. ZSM-5 catalyst (Grace) was calcined in the reactor for 4 hours at 600° C. in 1200 mL min$^{-1}$ flowing air prior to reaction.

For the olefin co-feed experiments, the secondary gas (T2 in FIG. 19) was switched to either ethylene or propylene and controlled at a desired flow rate. The helium fluidization gas flow rate was adjusted to hold the total inlet gas flow rate constant at 1200 mL min$^{-1}$.

After reaction, the secondary gas was switched to air to regenerate the catalyst. The combustion effluent during regeneration was passed over a copper catalyst held at 150° C. to convert carbon monoxide to carbon dioxide. The carbon dioxide stream was then passed over a dryrite trap to remove water vapor. The dry carbon dioxide was collected by a pre-weighted ascarite trap. The total moles of carbon dioxide collected in the trap were assumed to be substantially equal to the moles of carbon in the coke on the catalyst bed.

Olefin co-feed experiments were conducted using the reaction parameters outlined in Table 10. All reactor parameters were held constant except for the concentration of olefin in the inlet fluidization gas. As shown in Table 10, the moles of olefins exiting the reactor, in the case of propylene, were about half of the feed amount. This indicated that propylene was consumed during the reaction. When ethylene was used as the co-feed, there was a net production of ethylene during the reaction, which suggested that ethylene was a stable product and was non-reactive.

TABLE 10

Reaction parameters & olefin conversion for catalytic pyrolysis of wood

|  | Propylene Co-Feed | | Ethylene Co-Feed | | No Co-Feed |
|---|---|---|---|---|---|
| Run | 1 | 2 | 3 | 4 | 5 |
| Temperature (° C.) | 600 | 600 | 600 | 600 | 600 |
| Space velocity of wood (hr$^{-1}$) | 0.24 | 0.24 | 0.26 | 0.27 | 0.21 |
| g propylene/g wood | 0.16 | 0.04 | 0.08 | 0.02 | 0.00 |
| Propylene/wood (carbon amount) | 0.30 | 0.09 | 0.15 | 0.05 | 0.00 |
| Moles olefin out/in | 0.50 | 0.45 | 0.96 | 1.33 | N/A |

Figure 20A:
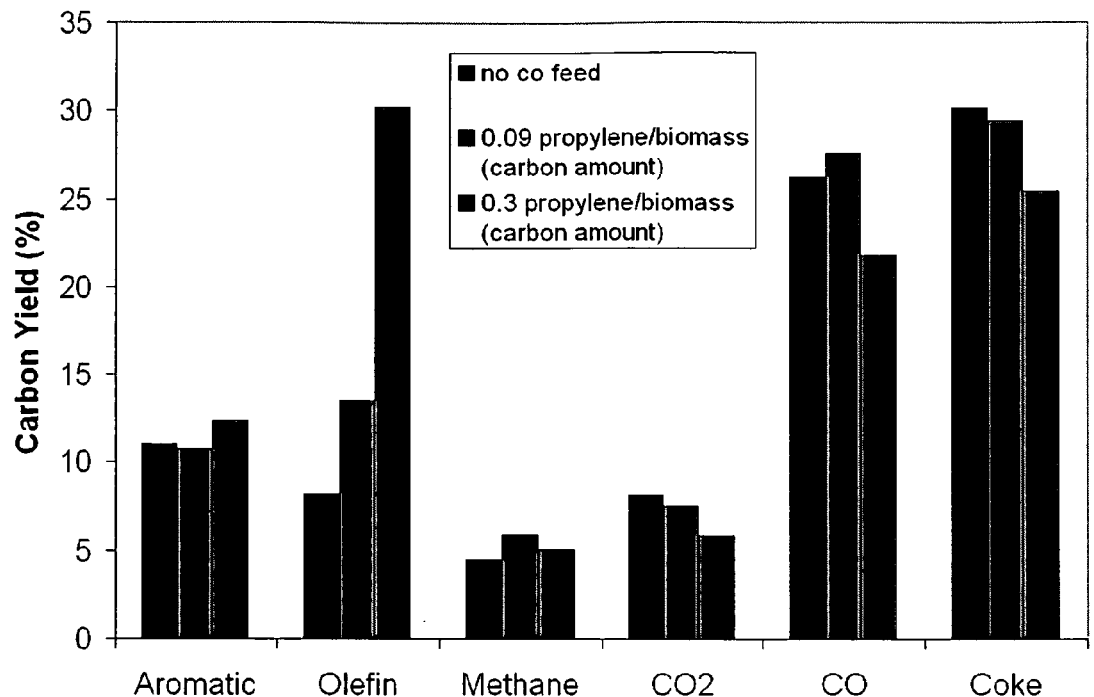
FIGS. 20A-20B include plots of carbon yield for various reaction products and reaction feed compositions, according to one set of embodiments.
Figure 20B:
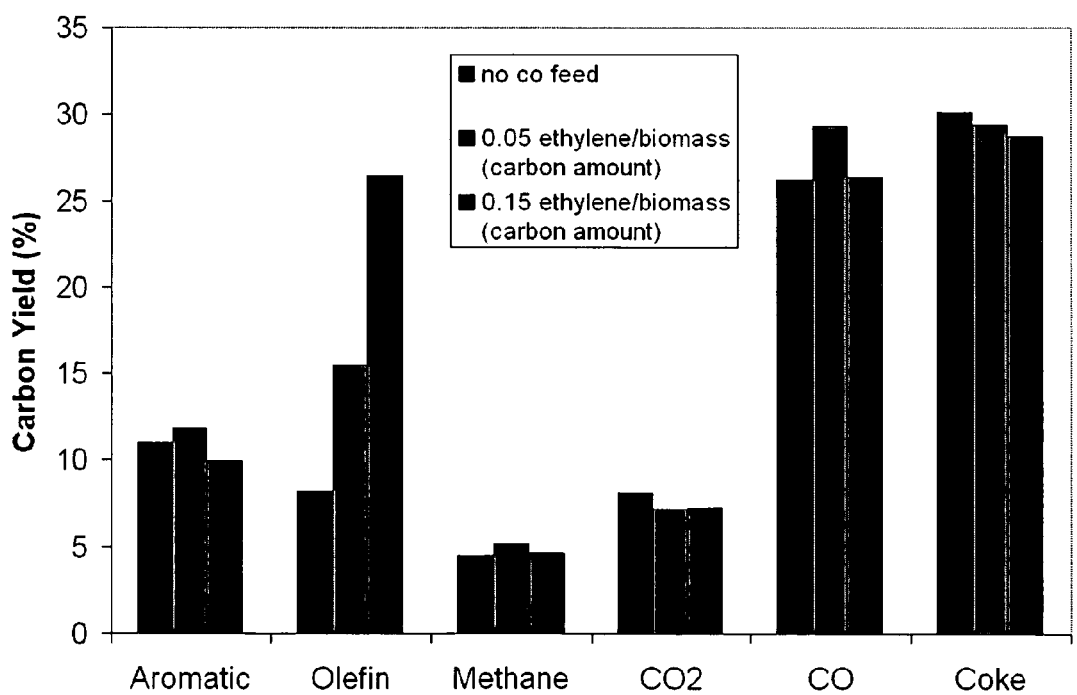

FIGS. 20A-20B include plots of product yields for the catalytic pyrolysis (CP) of wood with A) a propylene co-feed, and B) an ethylene co-feed. The aromatics quantified included benzene, toluene, xylene, ethyl-benzene, styrene, indene, phenol and naphthalene. The olefins quantified included ethylene, propylene, butene and butadiene. The carbon yields were calculated as the amount of carbon in the given product divided by the total amount of carbon in the feed (wood and olefin). As shown in FIG. 20A, the aromatic yield increased slightly while the coke yield decreased significantly from 30 to 25% when propylene was used as a co-feed. The yield of carbon dioxide and carbon monoxide also decreased at higher propylene feed concentrations. For ethylene co-feed, there was a decrease in aromatic yield with increasing feed concentration (FIG. 20B). The coke yield also decreased slightly with increasing ethylene concentration; however, this observed change was less pronounced that that observed when propylene was co-fed.

Figure 21A:
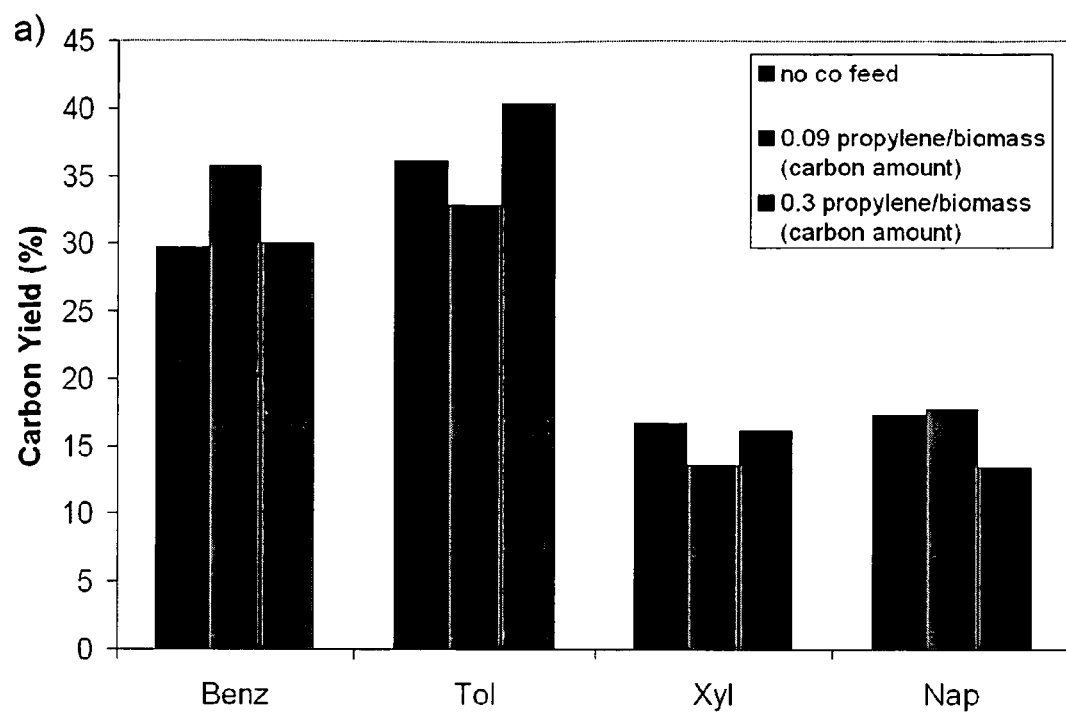
FIGS. 21A-21B include plots of (A) carbon yield and (B) aromatic selectivity for various reaction products and reaction feed compositions, according to one set of embodiments.
Figure 21B:
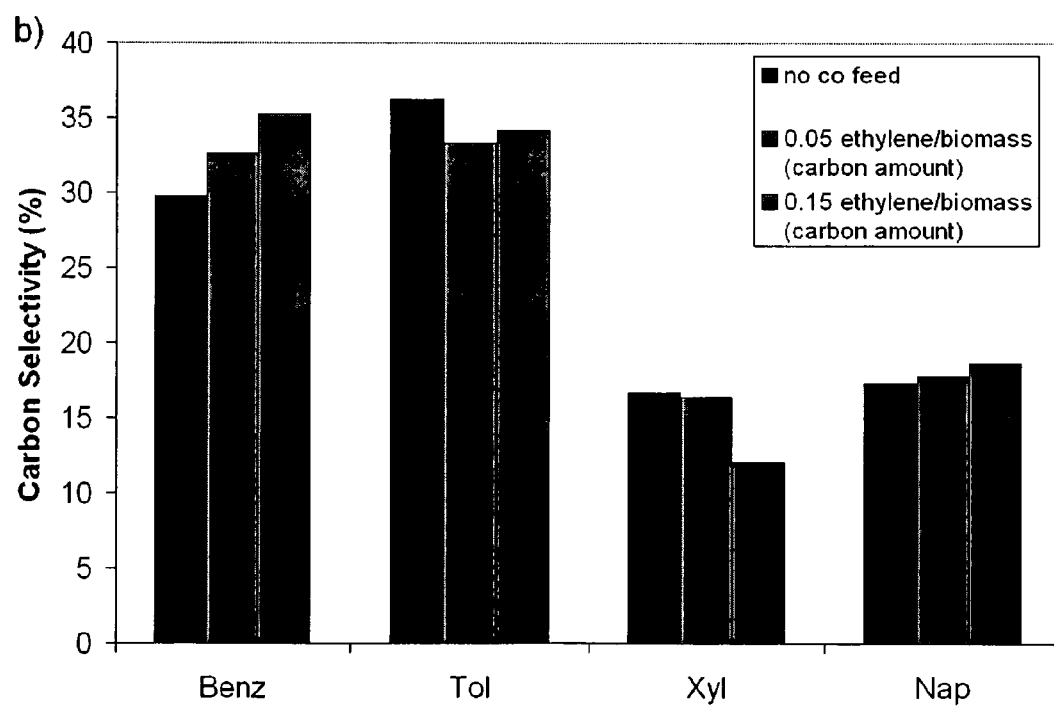

FIGS. 21A-21B include plots of product selectivity for various aromatics for the catalytic pyrolysis of wood with a) propylene co-feed, and b) ethylene co-feed. As shown in FIGS. 21A-21B, the selectivity for benzene, toluene, xylene and naphthalene changed with different olefin co-feeds. Propylene had little effect on the selectivity for benzene and xylene. However, propylene did affect the selectivity for toluene and naphthalene. The selectivity for toluene increased from 36% to 40%, while that for naphthalene decreased from 17% to 13%. Ethylene exhibited an opposite trend, as it affected the selectivity for benzene and xylene and did not have a significant effect on toluene or naphthalene. The selectivity for benzene increased from 30% to 35%, while that for xylene decreased from 17 to 12%.

Example 15

This example outlines the effects of varying the sizes of the particles within catalyst objects (i.e. in the form of catalyst particle agglomerates) on the types and amounts of compounds produced during the catalytic pyrolysis of hydrocarbonaceous material. Catalytic pyrolysis experiments were conducted using a model 2000 pyroprobe analytical pyrolizer (CDS Analytical Inc.). The probe included a computer-controlled resistively heated element which held an open ended quartz tube. Powdered samples were held in the tube with loose quartz wool packing. During pyrolysis, vapors flowed from the open ends of the quartz tube into a larger cavity (the pyrolysis interface) with a helium carrier gas stream. The carrier gas stream was routed to a model 5890 gas chromatograph (GC) interfaced with a Hewlett Packard model 5972A mass spectrometer (MS). The pyrolysis interface was held at 100° C., and the GC injector was held at a temperature of 275° C. Helium was used as an inert pyrolysis gas as well as the carrier gas for the GCMS system. A 0.5 ml min$^{-1}$ constant flow program was used for the GC capillary column (Restek Rtx-5sil MS). The GC oven was programmed with the following temperature regime: hold at 50° C. for 1 min, ramp to 270° C. at 10° C. min$^{-1}$, hold at 270° C. for 15 min. Products were quantified by injecting calibration standards into the GC/MS system. All yields were reported in terms of molar carbon yield, calculated as the moles of carbon in the product divided by the moles of carbon in the feed. The aromatic selectivity reported was defined as the moles of carbon in an aromatic species divided by the total moles of aromatic species carbon.

Powdered reactants were prepared by physically mixing a D-glucose (Fisher) feed and the catalyst. For a typical run, about 8-15 mg of reactant-catalyst mixture was used. Both the feed and the catalyst were sifted to <140 mesh before mixing. The physical mixtures of glucose were prepared with a ZSM-5 to glucose ratio of 19. ZSM-5 was calcined at 500° C. in air for 5 hours prior to reaction. In all experiments, a heating rate of 1000° C./s and a reaction temperature of 600° C. were used.

Figure 26A:
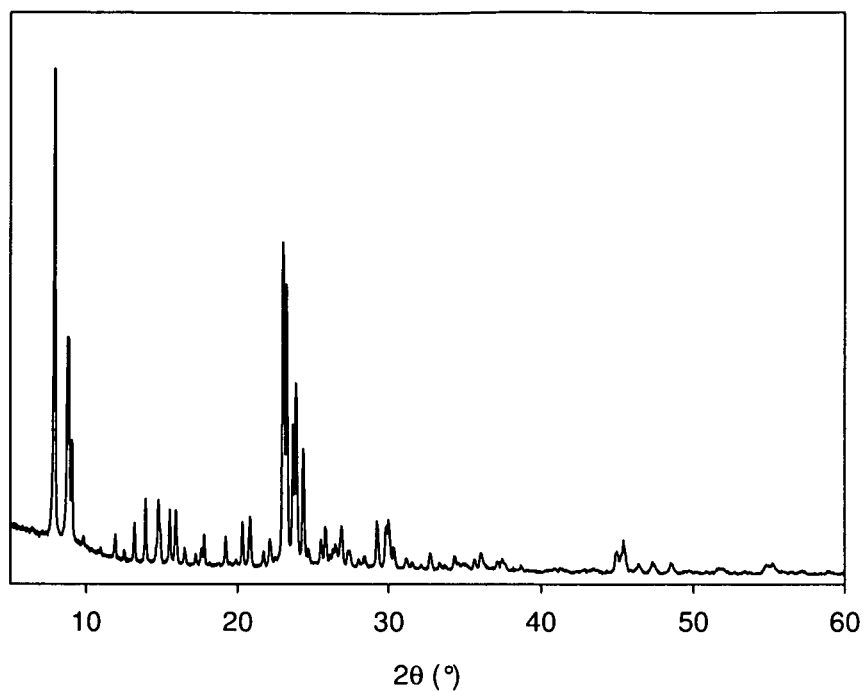
FIGS. 26A-26C include powder x-ray diffraction (PXRD) patterns for various ZSM-5 catalysts, according to one set of embodiments.

In order to investigate the effect of particle size on catalytic activity, three different particle sizes of ZSM-5 were prepared. The first ZSM-5 catalyst sample, designated as AG101, was prepared as follows. 0.93 g of NaOH was dissolved in 9 mL deionized water, and 12 g of Ludox AS-40 was added to the solution and stirred to form a synthesis mixture. A gel was formed, and the stirring was continued for 15 min. 0.233 g of NaAlO$_2$ was dissolved in 2 mL of deionized water. The NaAlO$_2$ solution was added to the synthesis mixture and stirred for 10 min. Next, 8.0 g of TPAOH solution (40%) was added dropwise to the synthesis mixture, and stirring was continued for 1 h. The final pH of the synthesis mixture was measured to be about 13. The synthesis mixture was then transferred to a Teflon lined autoclave (internal volume 45 mL). The hydrothermal synthesis was carried out at static conditions at 170° C. for 72 h under autogeneous pressure. The contents of the autoclave qwew centrifuged and washed 5 times, each time with 50 mL of deionized water, and dried overnight at 100° C. The resulting material was calcined in air at 300° C. for 3 h, followed by calcining at 550° C. for 6 h, with a temperature ramp of 1° C./min. FIG. 26A includes a PXRD pattern for the AG101 catalyst material.

Figure 26B:
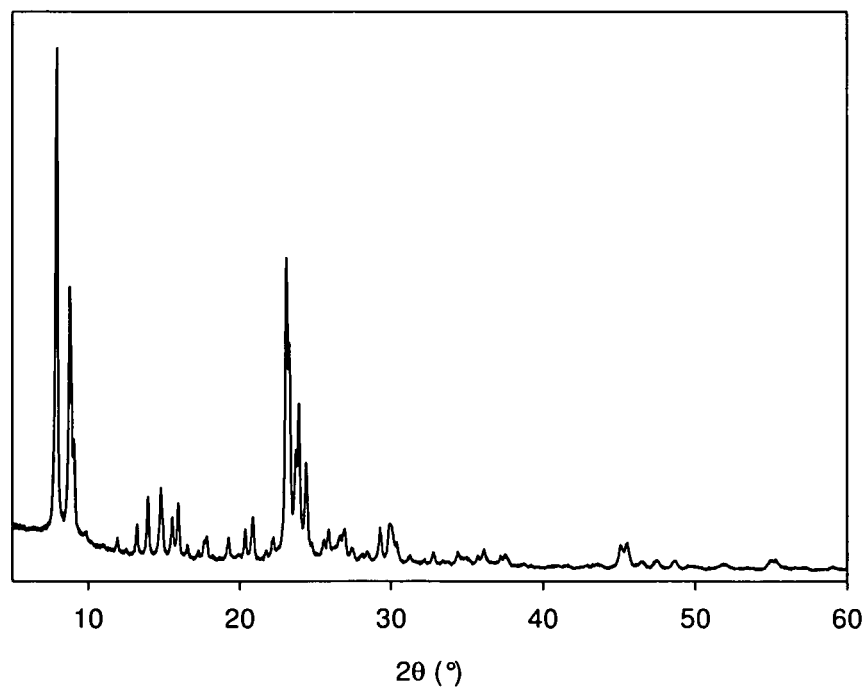

The process for producing the second ZSM-5 catalyst sample (designated as AG102) was similar to the process for producing AG101, except a solution of 1.8 g of acetic acid in 1.8 mL of deionized water was added dropwise after the dropwise addition of TPAOH solution. After stirring for 10 minutes, the final pH of the synthesis mixture was measured to be about 10. This synthesis mixture was then transferred to a Teflon lined autoclave and processed in a similar fashion as the AG101 sample. FIG. 26B includes a PXRD pattern for the AG102 catalyst material.

Figure 26C:
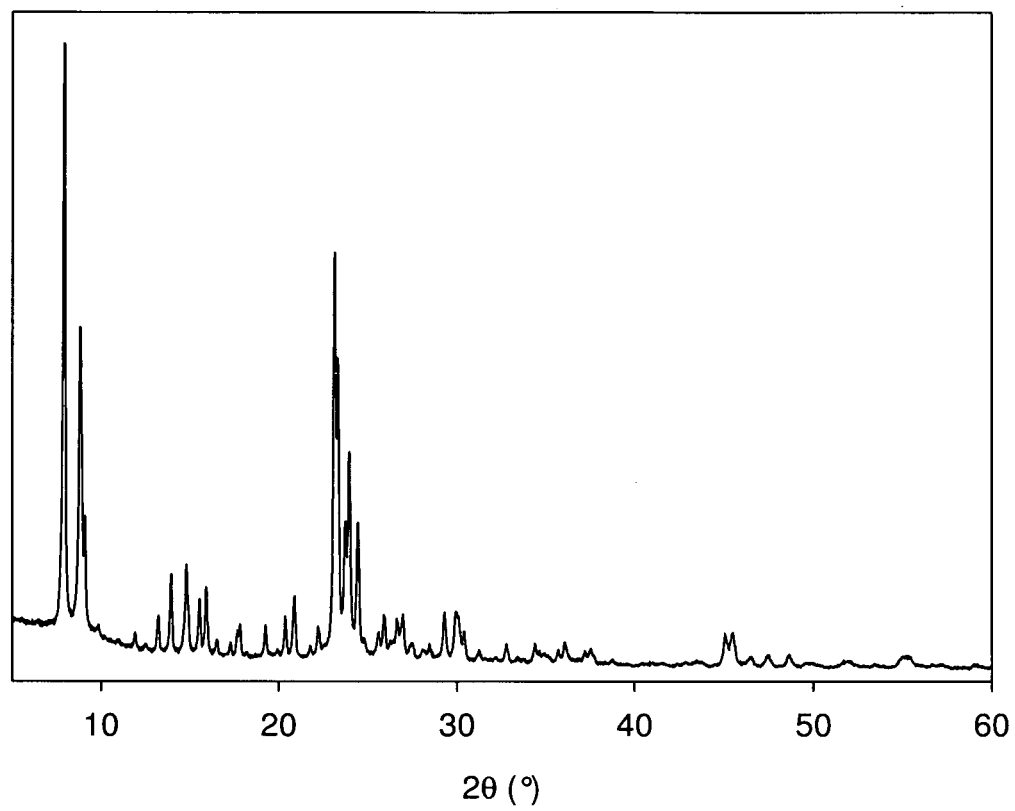

The process for producing the third ZSM-5 catalyst sample (designated as AG103) was similar to the process for producing AG102 (i.e., including dropwise addition of the acetic acid solution to produce a final pH of about 10), except the hydrothermal synthesis was carried out at static conditions at 170° C. for 168 hours (as opposed to 72 hours for the AG101 and AG102 catalysts) under autogeneous pressure. FIG. 26C includes a PXRD pattern for the AG103 catalyst material.

Figure 22A:
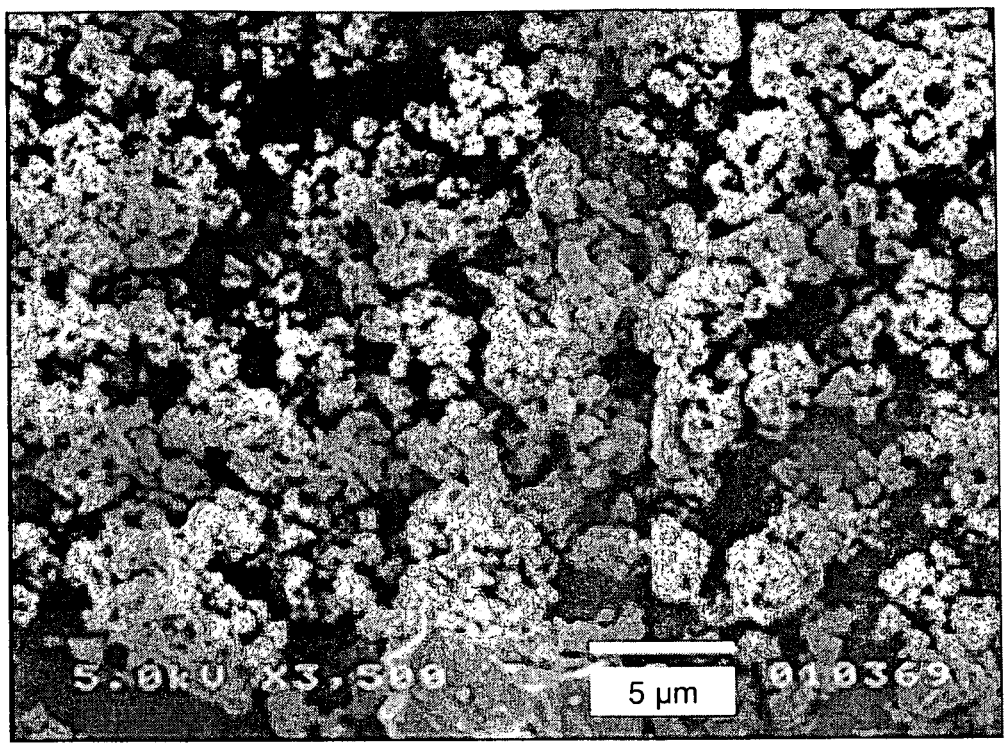
FIGS. 22A-22F include exemplary SEM images of catalysts.
Figure 22B:
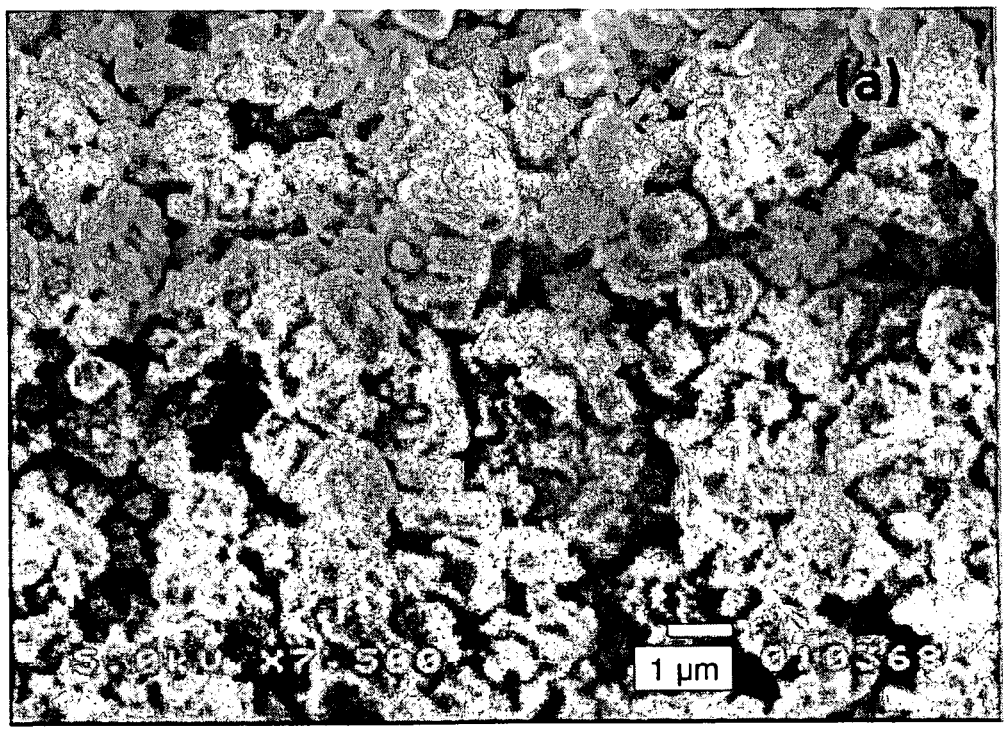
Figure 22C:
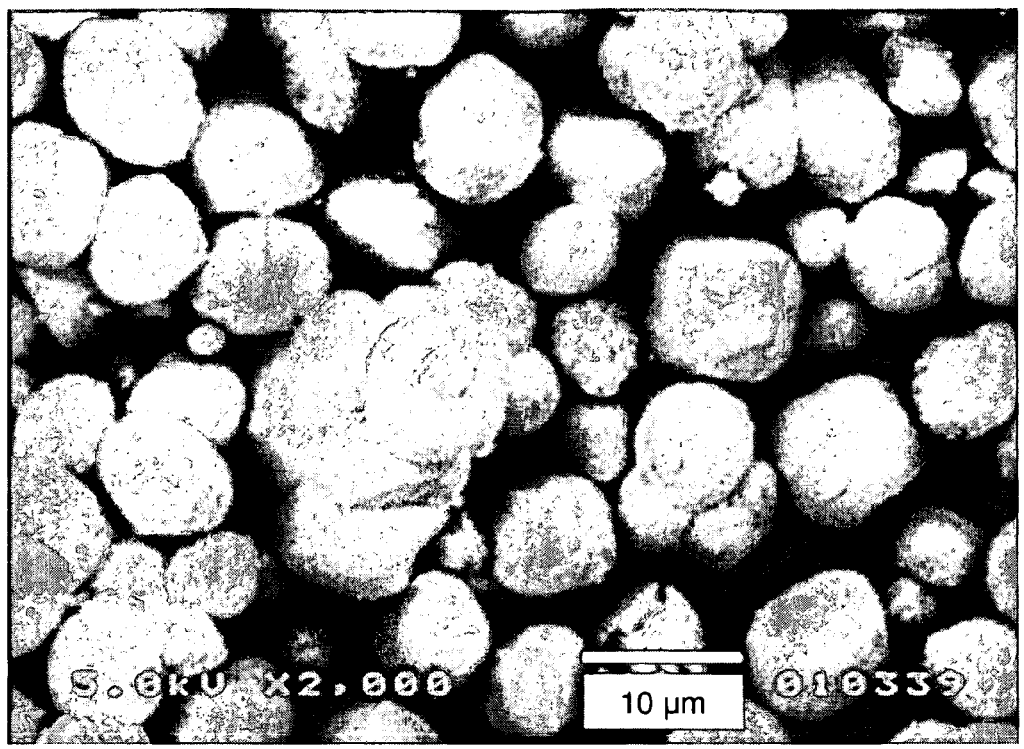
Figure 22D:
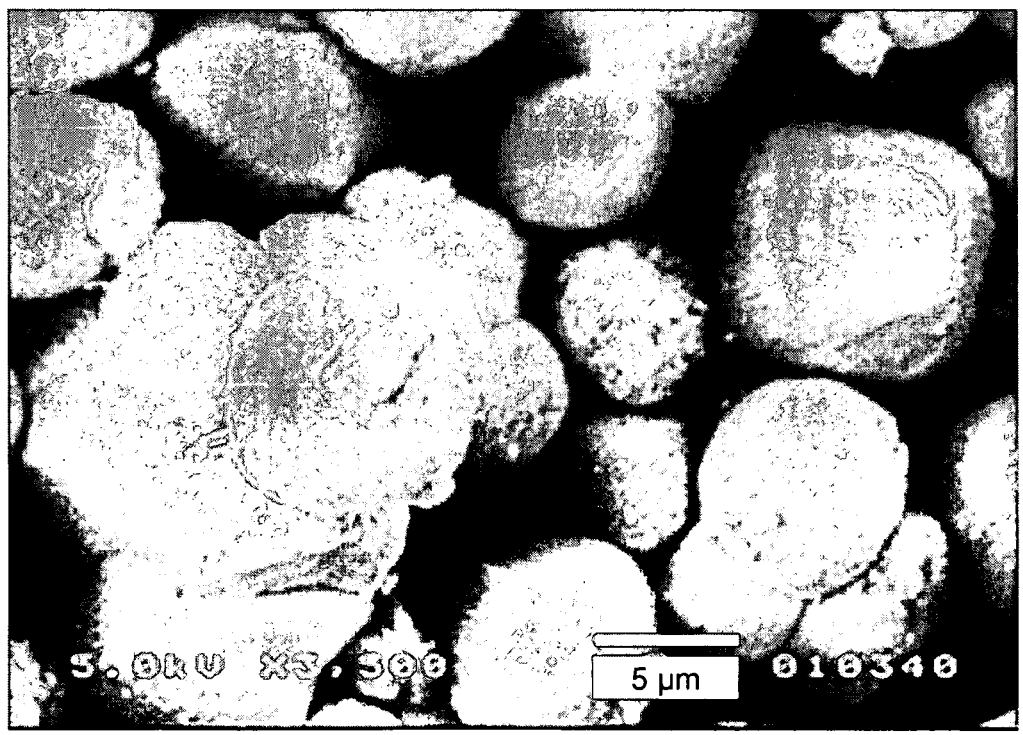
Figure 22E:
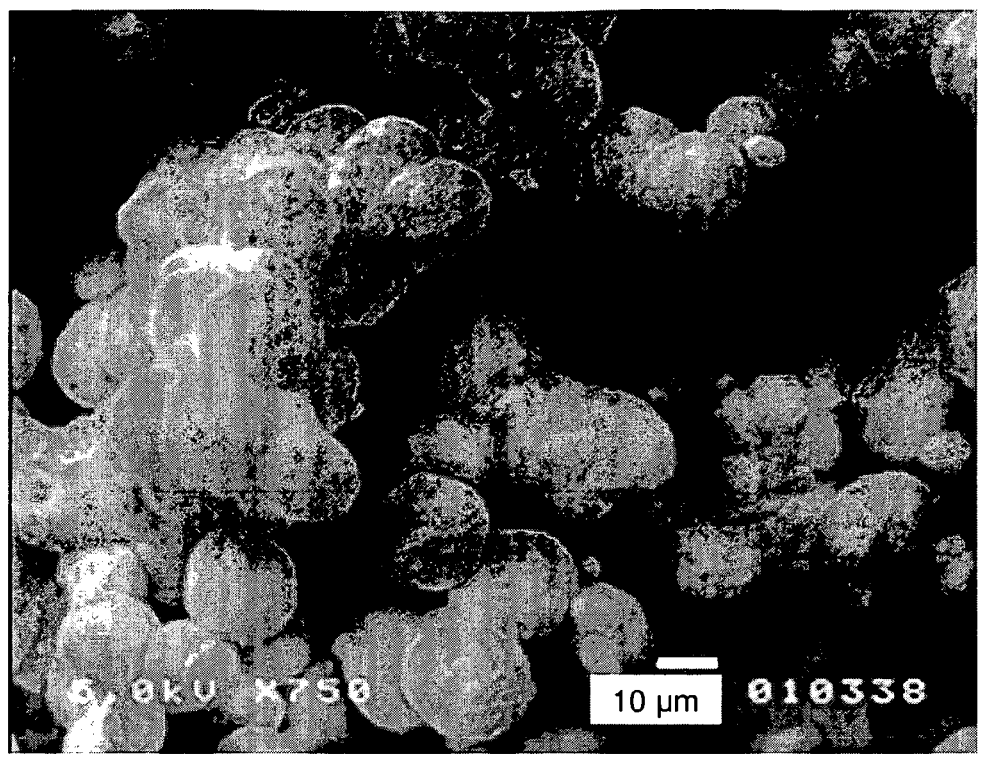
Figure 22F:
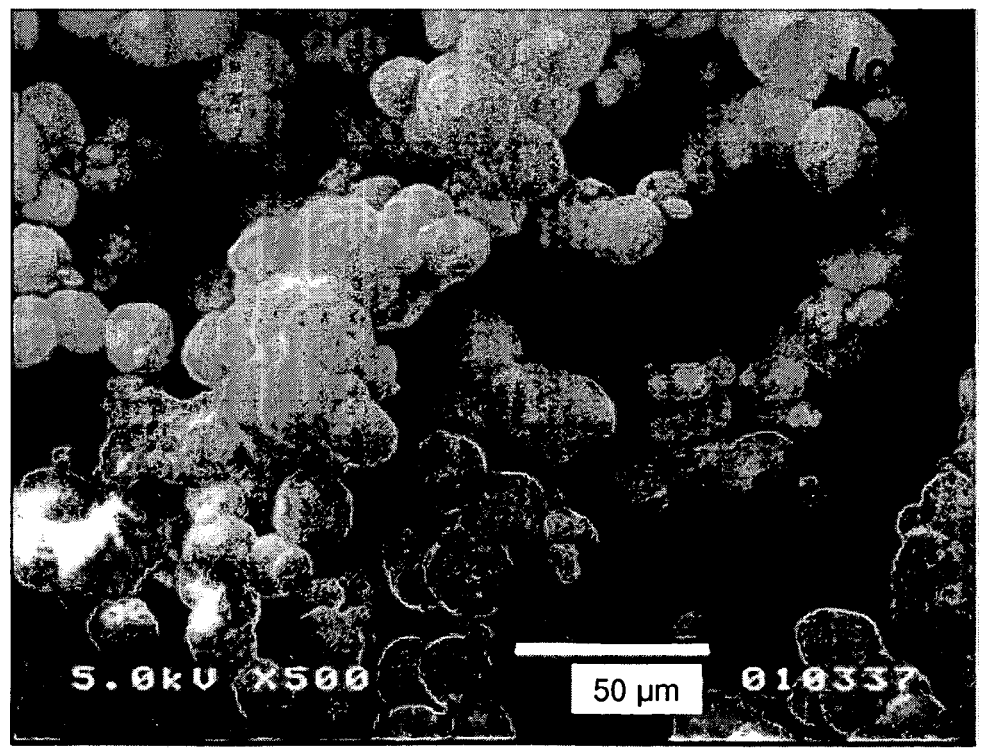
Figure 23A:
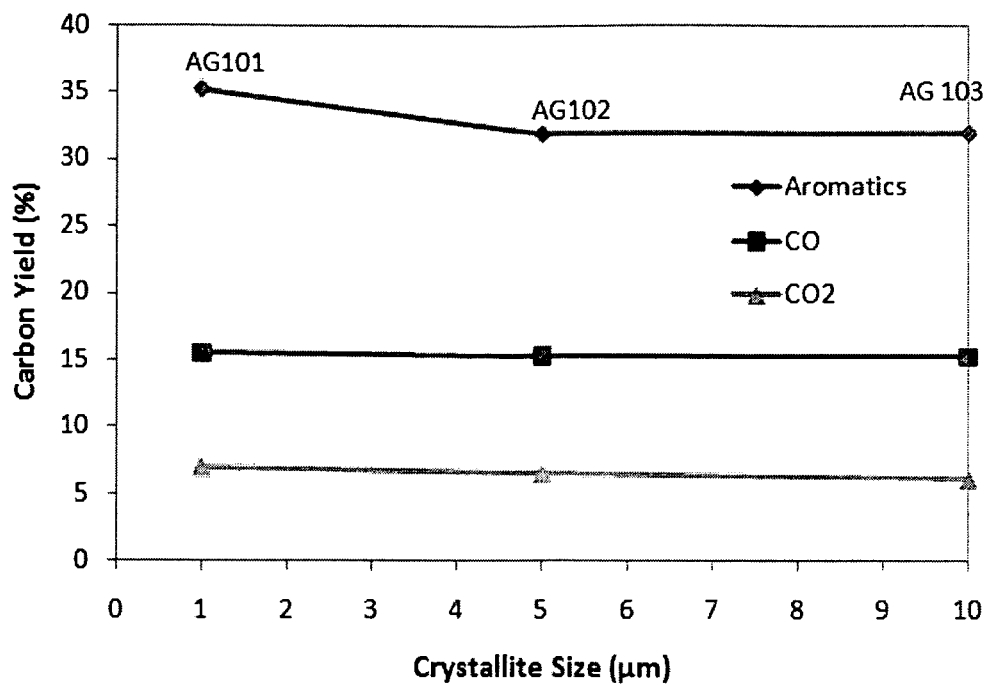
FIGS. 23A-23B include plots of (A) carbon yield and (B) aromatic selectivity for various reaction products as a function of particle size, according to one set of embodiments.
Figure 23B:
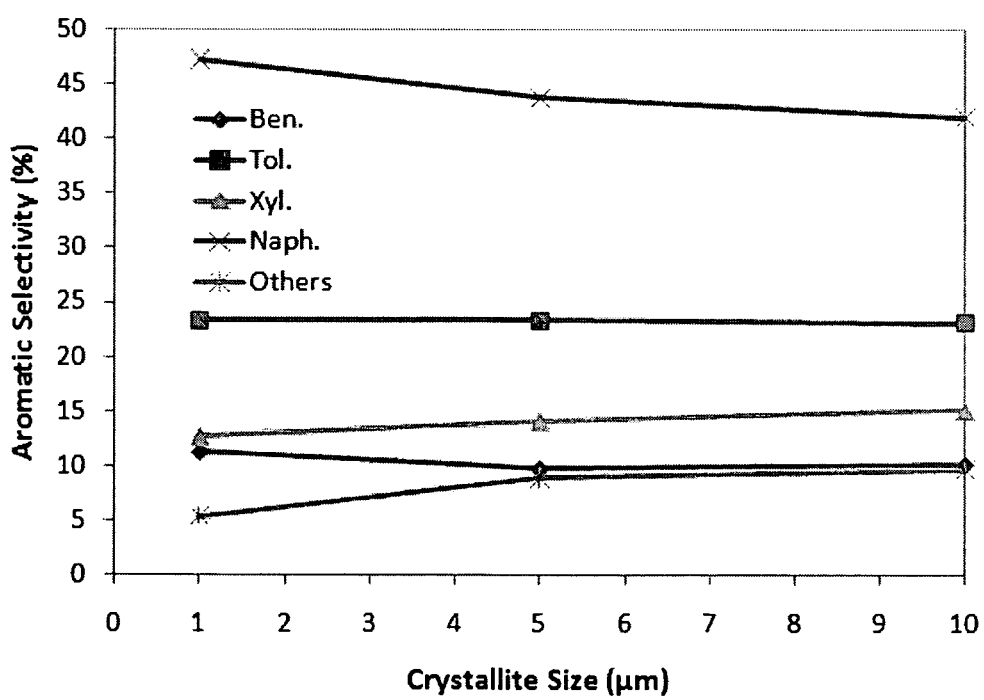

The chemical composition of the catalysts was determined using X-ray fluorescence (XRF). As shown in Table 11, all three catalysts had Si to Al ratios of about 30:1 (corresponding to silica to alumina ratios of about 60:1). The particle size was determined using scanning electron microscopy (SEM, JEOL X-Vision 6320FXV FESEM) coupled with ImageJ software. About 10 to 20 particles in each SEM image were chosen to calculate an average particle size. As shown in FIGS. 22A-22F, all three samples had different particle sizes. FIGS. 22A-22B include SEM images of AG 101 catalyst, FIGS. 22C-22D include SEM images of AG 102 catalyst, and FIGS. 22E-22F include SEM images of AG 103 catalyst. The AG101 catalyst included particle sizes of about 1 micron, the AG102 catalyst included particle sizes of about 10 microns, and the AG 103 catalyst included particle sizes of about 20 microns. FIG. 23A includes a plot of the carbon yields of aromatic compounds, CO, and $CO_2$ as a function of particle size for the catalytic pyrolysis of glucose. FIG. 23B outlines the aromatic selectivity of several aromatic compounds, including benzene, toluene, xylete, naphthalene, and "others" (which included ethyl-methyl-benzene, trimethyl-benzene, indane, and indene) as a function of particle size for the catalytic pyrolysis of glucose. Generally, aromatic yield increased as particle size decreased. For example, catalytic pyrolysis using AG 101 yielded 35.2% aromatics, while the use of AG 103 yielded 31.9%.

Figure 24A:
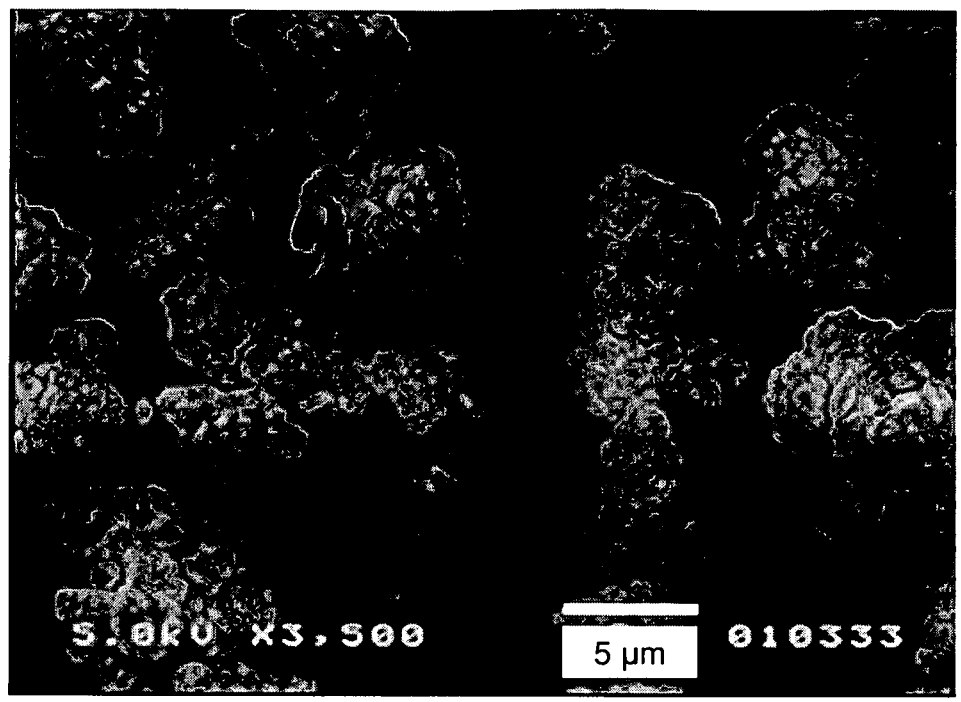
FIGS. 24A-24D include exemplary SEM images of catalysts.
Figure 24B:
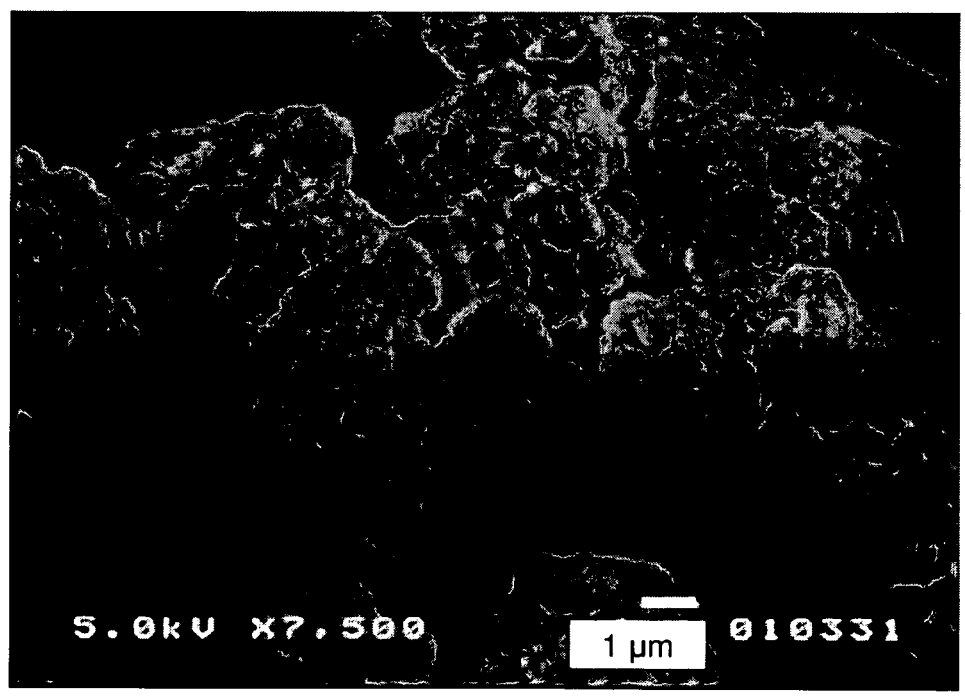
Figure 24C:
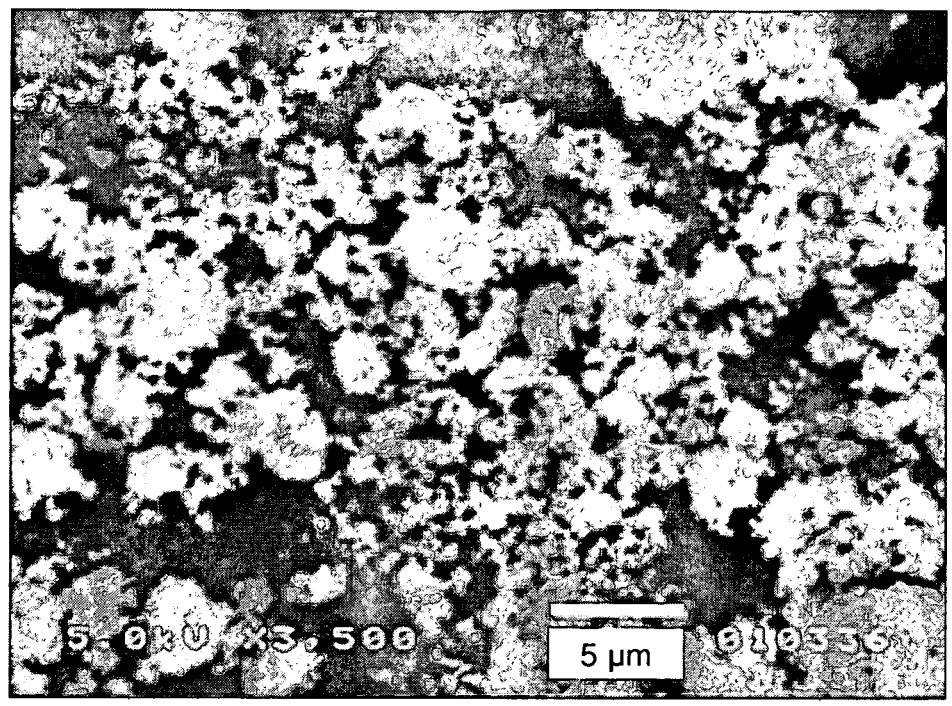
Figure 24D:
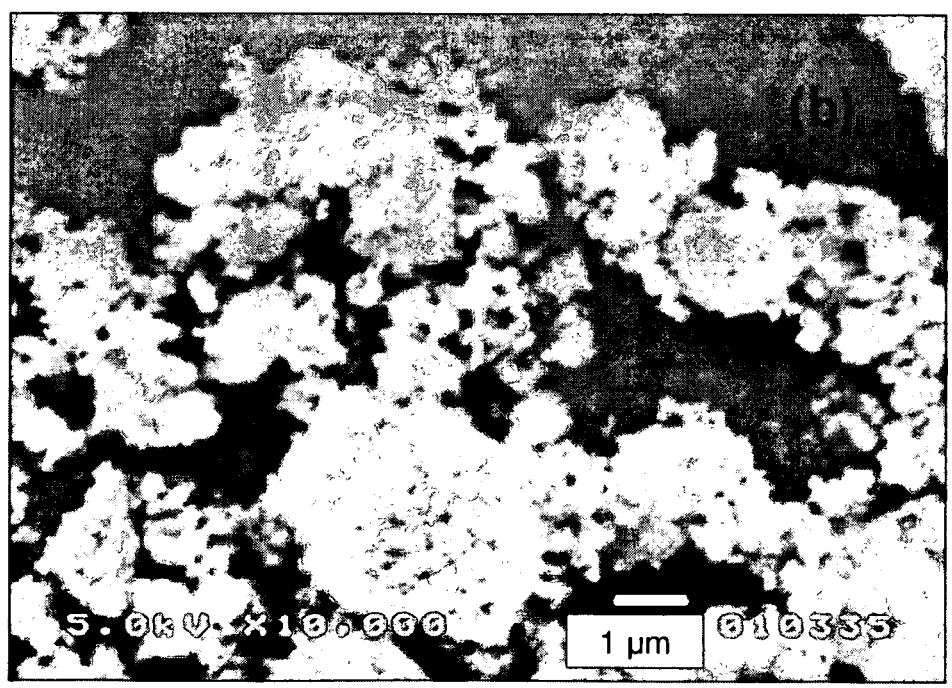
Figure 25:
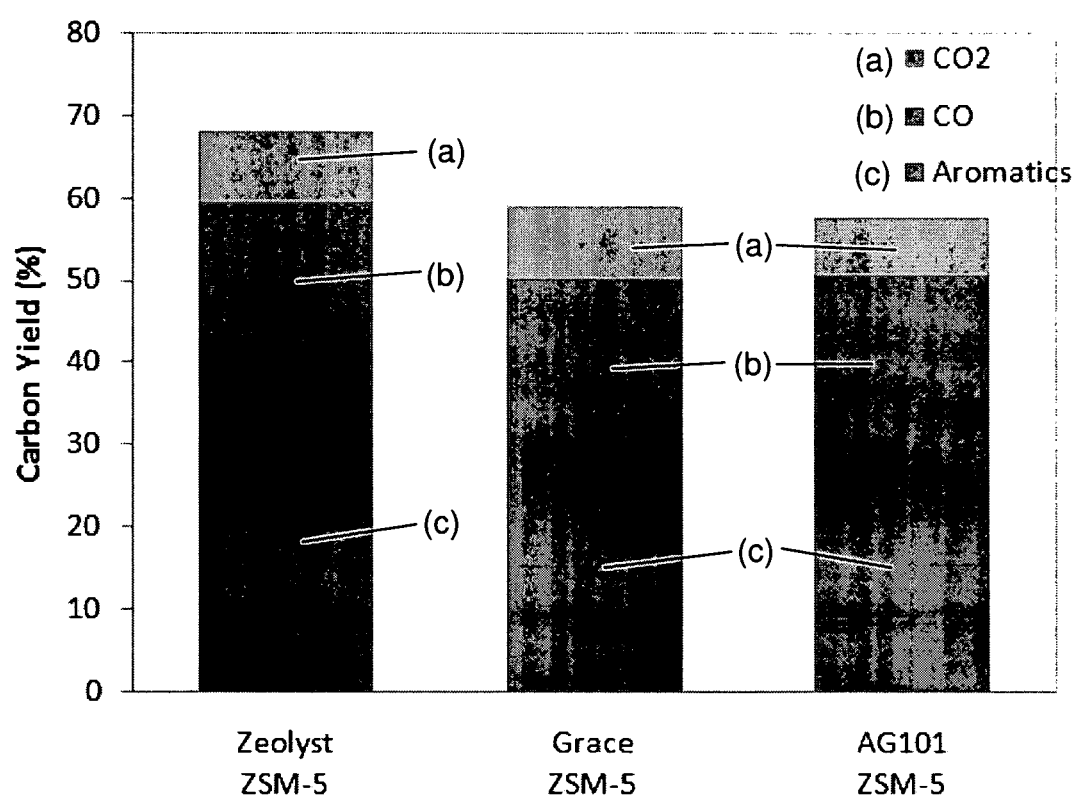
FIG. 25 includes a plot of carbon yield of various reaction products for several catalysts, according to one set of embodiments.

Additionally, two commercial ZSM-5 catalysts from WR Grace and Zeolyst were tested. The commercial catalysts had the same chemical composition (Si/Al=15), but different particle sizes. FIGS. 24A-24B include SEM images of the WR Grace ZSM-5 catalyst, showing a particle size of about 6 microns. FIGS. 24C-24D include SEM images of the Zeolyst ZSM-5 catalyst, including a broad range of catalyst particle sizes from less than 1 micron to a maximum of 3 microns. FIG. 25 includes a plot of the carbon yields of various products for the catalytic pyrolysis of glucose using the Zeolyst ZSM-5 and WR Grace ZSM-5 (with the AG101 ZSM-5 catalyst results included as a reference). As before, these experiments employed a catalyst to feed ratio or 19, a heating rate of 1000° C./s, and a reaction temperature of 600° C. From FIG. 25, it is clear that the Zeolyst ZSM-5 produced about 10% more aromatics than WR Grace ZSM-5.

TABLE 11

Elemental analyses of the AG catalysts by XRF

| Sample | Na (wt %) | Si (wt %) | Al (wt %) |
|---|---|---|---|
| AG 101 | 1.667 | 43.56 | 2.66 |
| AG 102 | 0.938 | 45.26 | 1.46 |
| AG 103 | 0.625 | 45.31 | 1.39 |

Example 16

Figure 27:
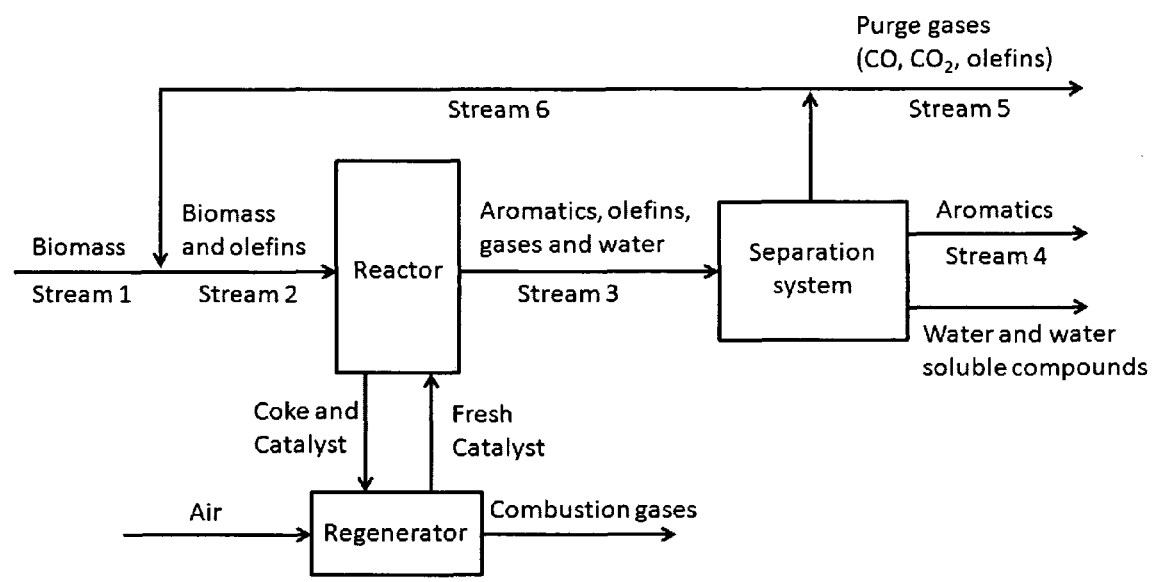
FIG. 27 includes an exemplary schematic illustration of a catalytic pyrolysis process, according to one set of embodiments.

This example includes a description of a theoretical calculation outlining the effects of feeding olefins on the types and amounts of products formed during the catalytic pyrolysis of a hydrocarbonaceous feed material. The feasibly of recycling olefins to a reactor can be assessed using a simple mass balance on the model system illustrated in FIG. 27. In the set of embodiments illustrated in FIG. 27, wood (labeled biomass in Stream 1) is mixed with a recycle stream (Stream 3) containing olefins, CO, and $CO_2$. The mixture is fed into a fluidized bed reactor. Inside the reactor, the wood (dry basis) can react to form aromatics and olefins by Reactions (4) and (5), respectively.

$$C_{3.8}H_{5.8}O_{2.7} \rightarrow 0.36 C_7H_8 + 1.45 H_2O + 1.25 CO \quad (4)$$

$$C_{3.8}H_{5.8}O_{2.7} \rightarrow 0.67 C_3H_6 + 0.9 H_2O + 1.8 CO \quad (5)$$

The olefins in the reactor can be converted to additional aromatics by Reaction (6).

$$C_3H_6 \rightarrow 3/7 C_7H_8 + 9/7 H_2 \quad (6)$$

For this exemplary calculation, it was assumed that the balance of biomass not converted into aromatics or olefins is converted into coke and gasses. In the set of embodiments illustrated in FIG. 27, the spent coked catalyst is then sent to a regenerator and regenerated by burning the coke in a secondary regeneration reactor. Most likely the catalyst recirculation would be adjusted to control the temperature of the reactor and regenerator. For this example, it was assumed that the coke yield would be relatively high, and heat removal from the regenerator might be necessary to avoid high temperatures in the regenerator. The excess heat could be utilized elsewhere in the process. In this example, the product stream from the reactor (Stream 3) is separated into the condensable aromatic product (Stream 4), water and water soluble compounds, and non-condensable olefins and gases. The separation system would include a condenser system that removes condensable compounds from the recyclable gases. The liquified product would contain a mixture of water, aromatics and water soluble compounds. The aromatic product would be decanted and further refined. The water and water soluble products would go to waste water treatment. From the separation system the olefins are then recycled to the reactor with a molar recycle ratio defined as moles of olefin in the recycle (Stream 6) divided by moles of olefin in the purge stream (Stream 5). The purge stream can be used to remove the CO and $CO_2$ and/or to avoid accumulation of any other non-reactive species in the system.

Figure 28:
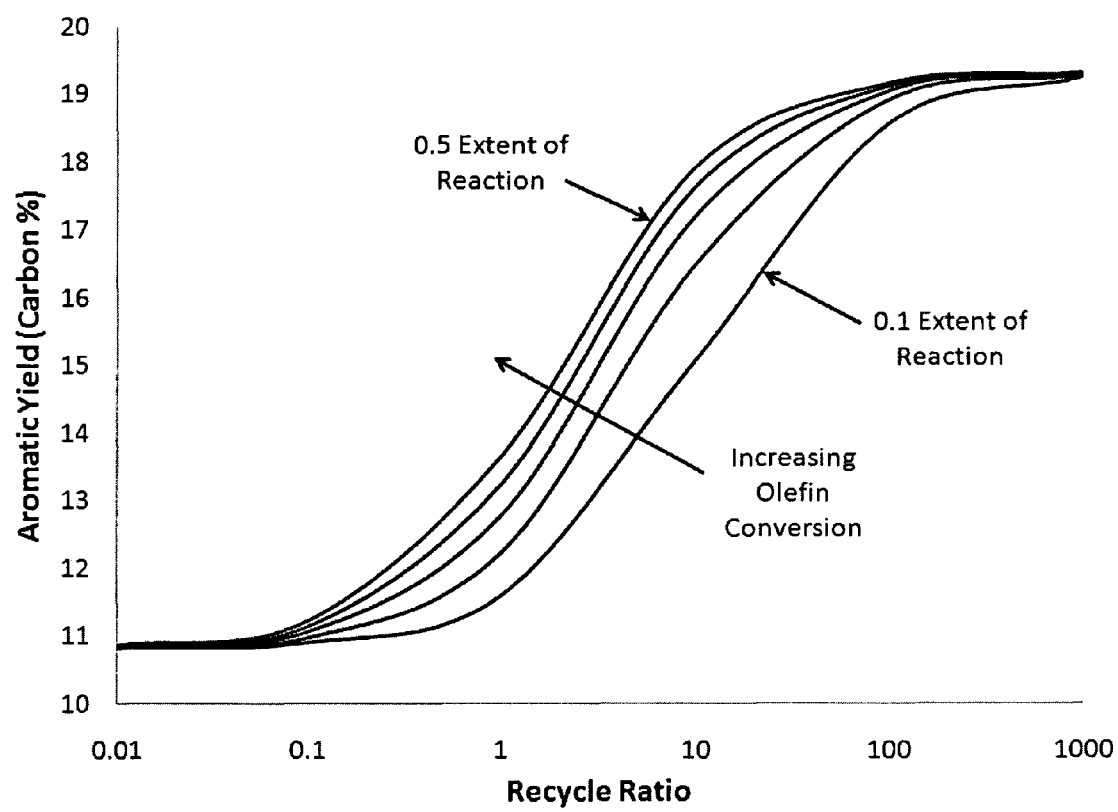
FIG. 28 includes, according to some embodiments, an exemplary plot of aromatic yield as a function of recycle ratio.

FIG. 28 includes an exemplary plot of the aromatic yield as a function of the recycle ratio. Solid lines are drawn for extents of olefin reaction (according to Equation 6 above) of 0.1, 0.2, 0.3, 0.4, and 0.5. Accordingly, FIG. 28 illustrates the effect of adjusting the olefin conversion and recycle ratio on the aromatic yield. The extent of reactions for Equations 4 and 5 were both fixed at 0.17 to match the experimental yield for olefins and aromatics at zero olefin co-feed in the fluidized bed reactor. As shown in FIG. 28, the yield of aromatics increases with both an increasing recycle ratio and an increasing extent of reaction for Reaction 6. The recycle ratio is defined as the mass of carbon within the hydrocarbonaceous material within the feed to the mass of carbon in the olefins in the recycle stream. Using recycle ratios in excess of 2:1 (or in excess of 3:1, or in excess of 4:1), and having high extents of reaction for Reaction 6 could produce a two-fold increase in aromatic yield for the system. In some cases in which fluidized bed reactors are employed, it can be advantageous to employ recycle ratios of less than 20:1, less than 10:1, or less than 5:1, which can be useful in maintaining a well-fluidized bed.

Example 17

This example describes the use of a synthesized zeolite catalyst comprising gallium (GaAlMFI) in the catalytic fast pyrolysis of furan in a flow, fixed-bed reactor.

H—GaAlMFI was synthesized using the methods described by Choudhary et al. in "H-Gallosilicate (MFI) Propane Aromatization Catalyst: Influence of Si/Ga Ratio on Acidity, Activity and Deactivation Due to Coking," *J. Catal.* 158 (1996) pages 34-50. H—GaAlMFI precursor solutions were prepared using N-brand silicate (SiO/NaO=3.22, PQ Corp.), Ga-nitrate (Sigma-Aldrich), Al-nitrate (BDH), tetra-propylammonium bromide (TPA-Br, Aldrich), deionized water, and sulfuric acid (which is used for adjusting pH). The composition of the final reaction mixture in molar oxide ratios was: $2.5 Al_2O_3:0.8 Ga_2O_3:100 SiO_2:12.5 TPA-Br:5020 H_2O$. The Si/(Al+Ga), Si/Ga, and Si/Al ratios in the mixture were 15, 60, and 20, respectively. The reaction mixture was crystallized at 180° C. under autogenous pressure for 72 hours in the autoclave. After synthesis, zeolite samples were washed with water and dried at 80° C. Samples were then calcined in air at 550° C. for 6 hours to remove occluded organic molecules. Zeolite samples were ion-exchanged to the H form by treatment in 0.1M $NH_4NO_3$ at 70° C. for 4 hours followed by filtration, drying at 80° C., overnight, and calcination under air at 550° C.

The GaAlMFI type catalyst was synthesized to have a MFI structure including a mixture of $SiO_2$, $Al_2O_3$, and $Ga_2O_3$. The catalyst was similar to a conventional ZSM-5 catalyst, with gallium atoms added to the MFI structure in the location of a portion of the aluminum sites. This type of substitution is often referred to as an isomorphic substitution (e.g., in this case, an isopmorphic substitution of Al into Ga).

Without being bound by any particular theory, it is believed that both Ga and Al generate bronsted acid sites, which can balance the negative charge in the catalyst. It is believed that the Ga and Al bronsted acid sites will have different acid strength, and therefore, the nature of acid sites is similar, but the strength of the acid sites is different. This mixture of acid site types might produce a relative increase in catalyst activity, relative to catalysts that do not include a mixture of acid sites.

For the purposes of this example, the catalyst was not analyzed to verify whether Ga is inside the zeolite framework or not. While it is expected that the Ga species are preferentially located inside the framework as a integrated structure, it is possible that some of the Ga can be located outside the framework as a gallium oxide form. In such case, the Ga outside the framework can also promote the reaction, but not as an acid site.

A flow, fixed-bed reactor system was constructed for biomass conversion. During reaction, helium (Airgas CO.) was used as a carrier gas, and its flow rate was controlled by a mass flow controller (controller: Brooks, SLA5850S1BAB1-C2A1; controlling box: Brooks, 0154CFD2B31A). Liquid feedstock was introduced into the carrier gas using a syringe pump (KD Scientific, KDS100), and was vaporized immediately. The vapor feedstock was then carried into a quartz tubular reactor. The quartz reactor was held in a temperature-controlled furnace (furnace: Lindberg, 55035A; temperature controller: Omega, CN96211TR). The fixed catalyst bed in the reactor was supported by a quartz frit. The temperature of the reactor was monitored by a thermocouple inserted through a quartz inner tube to the top surface of the packed bed. Products from the reactor flowed through an air-bathed condenser to condense heavy products (<0.05% carbon yield). Gas products were collected in gas-sampling bags. Liquid and gas products were analyzed by GC-FID (Shimadzu 2014). After reaction, the spent catalyst was regenerated by heating in air at 600° C. During regeneration, the effluent was passed through a copper converter (CuO, Sigma Aldrich) followed by a $CO_2$ trap (Ascarite, Sigma Aldrich). CO was oxidized to $CO_2$ in the copper converter. $CO_2$ was trapped by the $CO_2$ trap. Coke yield was obtained by measuring the change in weight of the $CO_2$ trap.

ZSM-5 (ZEOLYST, CBV 3024E, $SiO_2/Al_2O_3$=30) and GaAlMFI zeolite catalysts were used to react furan (Sigma-Aldrich, 99%) under a helium atmosphere in the flow reactor. The reaction conditions were as follows: furan partial pressure 6 torr, weight hourly space velocity (WHSV) 10.4 $h^{-1}$, and temperature 600° C. Table 12 summarizes the carbon yield and carbon selectivity of the major products, which contributed over 90% carbon yield. Table 13 shows the carbon selectivity of each aromatic product along aromatics. The carbon yield was defined as the moles of carbon in a given product type divided by the moles of a carbon fed to the reactor. The carbon selectivity was defined as moles of carbon in a product divided by the sum of the moles of carbon in all of the products.

As shown in Table 12, the choice of catalyst impacted the types of aromatics produced and their carbon selectivity. The carbon yield of aromatics increased from 11.84% for ZSM-5 to 18.15% for GaAlMFI. The carbon selectivity of aromatics increased from 30.30% for ZSM-5 to 39.11% for GaAlMFI. Moreover, the furan conversion increased from 0.48 for ZSM-5 to 0.54 for GaAlMFI. The carbon yield of olefins did not change significantly, but the carbon selectivity decreased due to an increase in the amount of aromatics produced. Coke yield also decreased when using GaAlMFI as the catalyst.

TABLE 12

Carbon yield (%) and carbon selectivity (%) for catalytic pyrolysis of furan

| Products | Carbon Yield (%) | | Carbon Selectivity (%) | |
|---|---|---|---|---|
| | ZSM-5 | GaAlMFI | ZSM-5 | GaAlMFI |
| Benzene | 3.43 | 7.38 | 8.77 | 15.91 |
| Toluene | 3.13 | 3.22 | 8.00 | 6.94 |
| Ethylbenzene | 0.16 | 0.07 | 0.40 | 0.16 |
| Xylene | 0.58 | 0.51 | 1.47 | 1.10 |
| Styrene | 1.08 | 1.49 | 2.76 | 3.22 |
| Benzofuran | 0.79 | 0.93 | 2.01 | 1.99 |
| Indene | 1.77 | 2.46 | 4.52 | 5.31 |

TABLE 12-continued

Carbon yield (%) and carbon selectivity (%) for catalytic pyrolysis of furan

| Products | Carbon Yield (%) | | Carbon Selectivity (%) | |
|---|---|---|---|---|
| | ZSM-5 | GaAlMFI | ZSM-5 | GaAlMFI |
| Naphthalene | 0.92 | 2.08 | 2.36 | 4.49 |
| CO | 5.94 | 9.15 | 15.21 | 19.73 |
| $CO_2$ | 0.48 | 0.45 | 1.23 | 0.96 |
| Ethylene | 3.16 | 2.33 | 8.09 | 5.03 |
| Propylene | 2.87 | 3.38 | 7.33 | 7.28 |
| $C_4$ olefins | 0.35 | 0.41 | 0.90 | 0.88 |
| coke | 14.44 | 12.54 | 36.94 | 27.02 |
| Aromatics | 11.84 | 18.15 | 30.30 | 39.11 |
| Olefins | 6.38 | 6.12 | 16.32 | 13.19 |

The selectivity toward various types of aromatics varied. As shown in Table 13, the selectivity toward benzene increased from 29% when ZSM-5 was used as the catalyst to 40% when GaAlMFI was used as the catalyst. Its selectivity among aromatics increased from 29% to 41%.

TABLE 13

Carbon selectivity (%) of aromatics

| Products | ZSM-5 | GaAlMFI |
|---|---|---|
| Benzene | 28.95 | 40.67 |
| Toluene | 26.42 | 17.76 |
| Ethylbenzene | 1.32 | 0.40 |
| Xylene | 4.86 | 2.80 |
| Styrene | 9.12 | 8.22 |
| Benzofuran | 6.63 | 5.10 |
| Indene | 14.91 | 13.57 |
| Naphthalene | 7.79 | 11.48 |
| Total | 100.0 | 100.0 |

While several embodiments of this invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of this invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. This invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of this invention.

The indefinite articles "a" and "an," as used herein in the specification and in the claims, unless clearly indicated to the contrary, should be understood to mean "at least one."

What is claimed is:

1. A method for producing one or more fluid hydrocarbon products from a solid hydrocarbonaceous material comprising:
   feeding the solid hydrocarbonaceous material to a reactor, wherein the solid hydrocarbonaceous material comprises lignocellulosic biomass;
   pyrolyzing within the reactor at least a portion of the solid hydrocarbonaceous material under reaction conditions sufficient to produce one or more pyrolysis products;
   reacting within the reactor in the presence of a catalyst at least a portion of the one or more pyrolysis products under reaction conditions sufficient to produce the one or more fluid hydrocarbon products, wherein the one or more fluid hydrocarbon products comprise olefins and aromatics, and wherein the catalyst comprises particles having a pore size of less than about 100 Angstroms;
   flowing the one or more fluid hydrocarbon products out of the reactor;
   separating at least a portion of the olefins from the one or more fluid hydrocarbon products to produce a recycle stream comprising the separated olefins and a product stream comprising a remainder of the one or more fluid hydrocarbon products;
   recovering said product stream; and
   recycling at least a portion of the recycle stream to the reactor to increase the amount of aromatic compounds in the one or more fluid hydrocarbon products; wherein the ratio of the mass of carbon within the solid hydrocarbonaceous material fed to the reactor to the mass of carbon in the olefins in the recycle stream is at least about 2:1, the aromatics in the one or more fluid hydrocarbon products comprise benzene, toluene, xylene, naphthalene or a mixture of two or more thereof, an amount of benzene, toluene, xylene, naphthalene or a mixture of two or more thereof in the one or more fluid hydrocarbon products is at least about 10% by weight based on the weight of the hydrocarbonaceous material used in forming the one or more pyrolysis products.

2. A method as in claim 1, wherein:
   the catalyst comprises silica and alumina and pores with a pore size in the range from about 5 to about 100 Angstroms.

3. A method as in claim 1, wherein the ratio of the mass of carbon within the solid hydrocarbonaceous material to the mass of carbon in the olefins in the recycle stream is between about 2:1 and about 20:1.

4. A method as in claim 1, wherein the ratio of the mass of carbon within the solid hydrocarbonaceous material to the mass of carbon in the olefins in the recycle stream is between about 3:1 and about 10:1.

5. A method as in claim 1, wherein the ratio of the mass of carbon within the solid hydrocarbonaceous material to the mass of carbon in the olefins in the recycle stream is between about 4:1 and about 5:1.

6. A method as in claim 1, wherein the reactor is a fluidized bed reactor.

7. A method as in claim 1, wherein the reactor is a circulating fluidized bed reactor or a turbulent fluidized bed reactor.

8. A method as in claim 1, wherein the solid hydrocarbonaceous material is fed to the reactor at a mass-normalized space velocity of between about 0.01 hour$^{-1}$ and about 10 hour$^{-1}$.

9. A method as in claim 8, further comprising varying the mass-normalized space velocity of the solid hydrocarbonaceous material to selectively produce different fluid hydrocarbon products.

10. A method as in claim 1, wherein the solid hydrocarbonaceous material comprises sugar cane bagasse, glucose, wood, corn stover, or a combination of two or more thereof.

11. A method as in claim 6, further comprising introducing a fluidization fluid into the fluidized bed reactor, the fluidization fluid having an average fluidization fluid residence time of at least about 10 seconds in the reactor.

12. A method as in claim 1, wherein the temperature in the reactor is between about 500° C. and about 1000° C.

13. A method as in claim 1, wherein the temperature in the reactor is at least about 700° C.

14. A method as in claim 1, wherein the one or more fluid hydrocarbon products comprise an amount of benzene, toluene, xylene, naphthalene, or a mixture of two or more thereof that is at least 15 wt % of the one or more fluid hydrocarbon products.

15. A method as in claim 1, wherein the reactor has a volume of at least about 1 liter.

16. A method as in claim 1, wherein the solid hydrocarbonaceous material and the catalyst are fed in one or more feed streams to the reactor such that the mass ratio of the catalyst to the solid hydrocarbonaceous material in the one or more feed streams is from about 0.5:1 to about 20:1.

17. A method as in claim 1, wherein a residence time of the solid hydrocarbonaceous material in the reactor is at least about 10 seconds.

18. A method as in claim 1, wherein the solid hydrocarbonaceous material comprises a first component and a second component, wherein the first and second components are different; and further comprising:
   providing a first and a second catalyst to the reactor, wherein the first catalyst is selective for catalytically reacting the first component or a derivative thereof to produce a fluid hydrocarbon product, and the second catalyst is selective for catalytically reacting the second component or a derivative thereof to produce a fluid hydrocarbon product.

19. A method as in claim 1, wherein the contents of the reactor in which the pyrolyzing step occurs are heated at a heating rate of greater than about 50° C./s.

20. A method as in claim 1, wherein the contents of the reactor in which the catalytic reaction step occurs are heated at a heating rate of greater than about 50° C./s.

21. A method as in claim 1, wherein the one or more fluid hydrocarbon products are produced from the pyrolysis products by dehydration, decarbonylation, decarboxylation, isomerization, oligomerization and/or dehydrogenation catalytic reactions.

22. The method of claim 1 wherein the catalyst comprises silica and alumina, in a silica to alumina molar ratio of at least about 30:1.

23. The method of claim 1 wherein the catalyst comprises silica and alumina, in a silica to alumina molar ratio of at least about 150:1.

24. The method of claim 1 wherein the catalyst comprises silica and alumina, in a silica to alumina molar ratio in the range from about 30:1 to about 200:1.

25. A method as in claim 1, wherein the catalyst comprises one or more of a zeolite catalyst, a non-zeolite catalyst, a metal catalyst and/or a metal oxide catalyst.

26. A method as in claim 1, wherein the catalyst comprises a zeolite catalyst.

27. A method as in claim 1, wherein the catalyst comprises ZSM-5.

28. A method as in claim 1, wherein the catalyst comprises silica and alumina in a silica to alumina molar ratio of from about 30:1 to about 200:1.

29. A method for producing one or more fluid hydrocarbon products from a solid hydrocarbonaceous material comprising:
feeding the solid hydrocarbonaceous material to a fluidized bed reactor and contacting a catalyst with the solid hydrocarbonaceous material in the reactor, wherein the solid hydrocarbonaceous material comprises lignocellulosic biomass, the catalyst particles having a pore size of less than about 100 Angstroms, the catalyst comprises silica and alumina in a silica to alumina molar ratio of at least about 30:1;
pyrolyzing within the reactor at least a portion of the solid hydrocarbonaceous material under reaction conditions sufficient to produce one or more pyrolysis products;
catalytically reacting within the reactor at least a portion of the one or more pyrolysis products under reaction conditions sufficient to produce the one or more fluid hydrocarbon products, wherein the one or more fluid hydrocarbon products comprise olefins and aromatics;
flowing a product stream comprising the one or more fluid hydrocarbon products out of the reactor;
separating at least a portion of the olefins from the one or more fluid hydrocarbon products to produce a recycle stream comprising the separated olefins and a product stream comprising a remainder of the one or more fluid hydrocarbon products;
recovering said product stream; and
recycling at least a portion of the recycle stream to the reactor to increase the amount of aromatic compounds in the one or more fluid hydrocarbon products; wherein the ratio of the mass of carbon within the solid hydrocarbonaceous material fed to the reactor to the mass of carbon in the olefins in the recycle stream is from about 2:1 to about 20:1[N], the aromatics in the one or more fluid hydrocarbon products comprise benzene, toluene, xylene, naphthalene or a mixture of two or more thereof, an amount of benzene, toluene, xylene, naphthalene or a mixture of two or more thereof in the one or more fluid hydrocarbon is at least about 15% by weight based on the weight of the hydrocarbonaceous material used in forming the one or more pyrolysis products; and
wherein a residence time of the solid hydrocarbonaceous material in the reactor is at least about 10 seconds, the residence time being calculated by dividing the volume of the reactor with the volumetric flow rate of hydrocarbonaceous material and the one or more fluid hydrocarbon products exiting the reactor.

30. A method as in claim 29, wherein the silica to alumina molar ratio is at least about 50:1.

31. A method as in claim 29, wherein the silica to alumina molar ratio is at least about 150:1.

32. A method as in claim 29, wherein the silica to alumina molar ratio is in the range from about 30:1 to about 150:1.

33. A method as in claim 29 wherein the catalyst comprises a zeolite catalyst having a bimodal distribution of pore sizes.

34. A method as in claim 29, wherein the catalyst comprises a plurality of pores;
at least about 95% of the pores of the one or more catalysts have smallest cross-sectional diameters that lie within a first size distribution or a second size distribution;
at least about 5% of the pores of the one or more catalysts have smallest cross-sectional diameters that lie within the first size distribution;
at least about 5% of the pores of the one or more catalysts have smallest cross-sectional diameters that lie within the second size distribution; and
the first and second size distributions do not overlap.

35. A method as in claim 29, wherein the the catalyst comprises pores with a pore size in the range from about 5.5 Angstroms to about 6.5 Angstroms.

36. A method as in claim 29, wherein the catalyst comprises pores with a pore size in the range from about 5.9 to about 6.3 angstroms.

37. A method as in claim 29, wherein the catalyst comprises a zeolite catalyst with a biomodal distribution of pore sizes.

38. A method for producing one or more fluid hydrocarbon products from a solid hydrocarbonaceous material comprising:
providing the solid hydrocarbonaceous material and one or more catalysts to a fluidized bed reactor, wherein the one or more catalysts comprise silica and alumina in a silica to alumina molar ratio of at least about 30:1, the one or more catalysts comprise pores with a pore size in the range from about 5 to about 100 Angstroms, and the solid hydrocarbonaceous material comprises lignocellulosic biomass;
pyrolyzing at least a portion of the hydrocarbonaceous material under reaction conditions sufficient to produce one or more pyrolysis products; and
catalytically reacting at least a portion of the pyrolysis products with the one or more catalysts to produce the one or more fluid hydrocarbon products, wherein the fluid hydrocarbon products comprise olefins and aromatics; and
recovering a product stream comprising the one or more fluid hydrocarbon products from the reactor, wherein the aromatics in the one or more fluid hydrocarbon products comprise benzene, toluene, xylene, naphthalene or a mixture of two or more thereof, an amount of benzene, toluene, xylene, naphthalene or a mixture of two or more thereof in the one or more fluid hydrocarbon products is at least about 10% by weight based on the weight of the hydrocarbonaceous material used in forming the one or more pyrolysis products;
wherein a residence time of the solid hydrocarbonaceous material in the reactor is at least about 10 seconds, the residence time being calculated by dividing the volume of the reactor with the volumetric flow rate of hydrocarbonaceous material and the one or more fluid hydrocarbon products exiting the reactor.

39. A method as in claim 38, further comprising separating the one or more fluid hydrocarbon products from the catalyst by passing the catalyst and the one or more fluid hydrocarbon products through a solids separator at a solids separator residence time of at least about 1 second and at a solids separator temperature of greater than about 500° C.

40. A method as in claim 38, wherein the one or more catalysts comprise a silica to alumina molar ratio of from about 30:1 to about 200:1.

41. A method as in claim 38, wherein the one or more catalysts comprise a silica to alumina ratio of from about 30:1 to about 150:1.

42. A method as in claim 38, wherein the one or more catalysts further comprise a metal or an oxide of said metal, wherein the metal comprises nickel, platinum, vanadium, palladium, manganese, cobalt, zinc, copper and/or gallium.

43. A method as in claim 38, wherein the one or more catalysts comprise pores having a pore size between about 5.9 and about 6.3 Angstroms.

44. A method as in claim 38, wherein the one or more catalysts comprise pores having a pore size between about 5.5 and about 6.5 Angstroms.

45. A method as in claim 38, wherein the one or more catalysts have a biomodal distribution of pore sizes.

46. A method as in claim 38, wherein:
the one or more catalysts comprise a plurality of pores;
at least about 95% of the pores of the one or more catalysts have smallest cross-sectional diameters that lie within a first size distribution or a second size distribution;
at least about 5% of the pores of the one or more catalysts have smallest cross-sectional diameters that lie within the first size distribution;
at least about 5% of the pores of the one or more catalysts have smallest cross-sectional diameters that lie within the second size distribution; and
the first and second size distributions do not overlap.

47. A method as in claim 38, wherein:
the one or more catalysts comprise a plurality of pores;
at least about 95% of the pores of the one or more catalysts have smallest cross-sectional diameters that lie within a first distribution and a second distribution, wherein the first distribution is between about 5.9 Angstroms and about 6.3 Angstroms and the second distribution is different from and does not overlap with the first distribution;
at least about 5% of the pores of the one or more catalysts have smallest cross-sectional diameters between about 5.9 Angstroms and about 6.3 Angstroms; and
at least about 5% of the pores of the one or more catalysts have smallest cross-sectional diameters that lie within the second distribution.

48. A method as in claim 38, wherein: the one or more catalysts comprise a plurality of pores;
at least about 95% of the pores of the one or more catalysts have smallest cross-sectional diameters between about 5.9 Angstroms and about 6.3 Angstroms or between about 7 Angstroms and about 100 Angstroms;
at least about 5% of the pores of the one or more catalysts have smallest cross-sectional diameters between about 5.9 Angstroms and about 6.3 Angstroms; and
at least about 5% of the pores of the one or more zeolite catalysts have smallest cross-sectional diameters between about 7 Angstroms and about 2-90100 Angstroms.

49. A method as in claim 38, wherein the one or more catalysts have one or more metals incorporated therein.

50. The method of claim 38 wherein the silica to alumina molar ratio is at least about 50:1.

51. The method of claim 38 wherein the silica to alumina molar ratio is at least about 150:1.

52. The method of claim 38 wherein the silica to alumina molar ratio is in the range from about 30:1 to about 200:1.

53. The method of claim 38 wherein the silica to alumina molar ratio is in the range from about 50:1 to about 160:1.

54. A method for producing one or more fluid hydrocarbon products from a solid hydrocarbonaceous material comprising:
providing the solid hydrocarbonaceous material to a fluidized bed reactor and contacting the solid hydrocarbonaceous material with a zeolite catalyst comprising gallium, wherein the zeolite catalyst comprises pores with a pore size in the range from about 5 to about 100 Angstroms, the zeolite catalyst comprises Si, Al and Ga, a ratio of moles of Si to the sum of moles of Ga and Al in the catalyst is at least about 15:1, and the solid hydrocarbonaceous material comprises lignocellulosic biomass;
pyrolyzing at least a portion of the solid hydrocarbonaceous material in the reactor under reaction conditions sufficient to produce one or more pyrolysis products;
catalytically reacting in the reactor at least a portion of the one or more pyrolysis products with the zeolite catalyst to produce the one or more fluid hydrocarbon products, wherein the one or more fluid hydrocarbon products comprise one or more aromatic compounds, the aromatic compounds in the one or more fluid hydrocarbon products comprise benzene, toluene, xylene, naphthalene or a mixture of two or more thereof, an amount of benzene, toluene, xylene, naphthalene or a mixture of two or more thereof in the one or more fluid hydrocarbon products is at least about 10% by weight based on the weight of the hydrocarbonaceous material used in forming the one or more pyrolysis products; and
recovering a product stream comprising the one or more fluid hydrocarbon products from the reactor;
wherein a residence time of the solid hydrocarbonaceous material in the reactor is at least about 10 seconds, the residence time being calculated by dividing the volume of the reactor with the volumetric flow rate of hydrocarbonaceous material and the one or more fluid hydrocarbon products exiting the reactor.

55. A method for producing one or more fluid hydrocarbon products from a solid hydrocarbonaceous material comprising:
providing a solid hydrocarbonaceous material to a fluidized bed reactor and contacting the solid hydrocarbonaceous material with a catalyst comprising a galloaluminosilicate Mordenite Framework Inverted zeolite, wherein the catalyst comprises pores with a pore size in the range from about 5 to about 100 Angstroms and the solid hydrocarbonaceous material comprises lignocellulosic biomass;
pyrolyzing at least a portion of the hydrocarbonaceous material in the reactor under reaction conditions sufficient to produce one or more pyrolysis products;
catalytically reacting in the reactor at least a portion of the pyrolysis products with the catalyst to produce the one or more fluid hydrocarbon products, wherein the one or more fluid hydrocarbon products comprise one or more aromatic compounds, the one or more aromatic compounds comprise benzene, toluene, xylene, naphthalene or a mixture of two or more thereof, an amount of benzene, toluene, xylene, naphthalene or a mixture of two or more thereof in the one or more fluid hydrocarbon products is at least about 10% by weight based on the weight of the hydrocarbonaceous material used in forming the one or more pyrolysis products; and
recovering a product stream comprising the one or more fluid hydrocarbon products from the reactor;
wherein a residence time of the solid hydrocarbonaceous material in the fluidized bed reactor is at least about 10 seconds, the residence time being calculated by dividing the volume of the reactor with the volumetric flow rate of hydrocarbonaceous material and the one or more fluid hydrocarbon products exiting the reactor.

56. A method as in claim 55, wherein the galloaluminosilicate Mordenite Framework Inverted zeolite is in the hydrogen form.

57. A method as in claim 55, wherein a ratio of moles of Si in the galloaluminosilicate zeolite catalyst to the sum of the moles of Ga and Al in the galloaluminosilicate zeolite catalyst is at least about 20:1.

58. A method as in claim 55, wherein a ratio of moles of Si in the galloaluminosilicate zeolite catalyst to the moles of Al in the galloaluminosilicate zeolite catalyst is at least about 10:1.

59. A method as in claim 55, wherein:
the catalyst comprises a plurality of catalyst particles, and
at least about 50% of the sum of the total volume of catalyst is occupied by particles having maximum cross-sectional dimensions of less than about 1 micron.

60. A method as in claim 55, wherein the one or more fluid hydrocarbon products contain more aromatic compounds than olefinic compounds.

61. A method as in claim 55, wherein the solid hydrocarbonaceous material comprises sugar cane bagasse, glucose, wood, corn stover, or a combination of two or more thereof.

62. A method as in claim 55, wherein the temperature in the reactor is between about 500° C. and about 1000° C.

63. A method as in claim 55, wherein the temperature in the reactor is at least about 700° C.

64. A method as in claim 55, wherein the fluid hydrocarbon product comprises an amount of aromatic compounds that is at least about 15 wt %.

65. A method as in claim 55, wherein the reactor has a volume of at least about 1 liter.

66. A method as in claim 55, wherein the catalyst comprises pores having a pore size from about 5.5 Angstroms to about 6.5 Angstroms.

67. A method as in claim 55, wherein the catalyst comprises pores having a pore size between about 5.9 and about 6.3 Angstroms.

68. A method as in claim 55, wherein the catalyst has a bimodal distribution of pore sizes.

69. A method as in claim 55, wherein:
the catalyst comprises a plurality of pores;
at least about 95% of the pores of the one or more catalysts have smallest cross-sectional diameters that lie within a first size distribution or a second size distribution;
at least about 5% of the pores of the one or more catalysts have smallest cross-sectional diameters that lie within the first size distribution;
at least about 5% of the pores of the one or more catalysts have smallest cross-sectional diameters that lie within the second size distribution; and
the first and second size distributions do not overlap.

70. A method for producing one or more fluid hydrocarbon products from a solid hydrocarbonaceous material comprising:
providing a solid hydrocarbonaceous material to a fluidized bed reactor and contacting a catalyst, wherein the catalyst comprises silica and alumina in a silica to alumina molar ratio of at least about 30:1, the catalyst comprises pores with a pore size in the range from about 5 to about 100 Angstroms, and the solid hydrocarbonaceous material comprises lignocellulosic biomass;
pyrolyzing within the reactor at least a portion of the solid hydrocarbonaceous material under reaction conditions sufficient to produce one or more pyrolysis products;
catalytically reacting in the reactor at least a portion of the one or more pyrolysis products using the catalyst under reaction conditions sufficient to produce the one or more fluid hydrocarbon products, wherein the one or more fluid hydrocarbon products comprise an amount of aromatic compounds that is at least 35 wt % of the total amount of the hydrocarbonaceous material used in forming the one or more pyrolysis products and which is calculated as the weight of the aromatic compounds present in the one or more fluid hydrocarbon products divided by the weight of the hydrocarbonaceous material used in forming the one or more pyrolysis products, and the aromatic compounds comprise benzene, toluene, xylene, naphthalene or a mixture of two or more thereof; and
recovering a product stream comprising the one or more fluid hydrocarbon products from the reactor;
wherein a residence time of the solid hydrocarbonaceous material in the fluidized bed reactor is at least about 10 seconds, the residence time being calculated by dividing the volume of the reactor with the volumetric flow rate of hydrocarbonaceous material and the one or more fluid hydrocarbon products exiting the reactor.

71. A method as in claim 70, wherein the catalyst comprises a silica to alumina molar ratio of about 30:1 to about 200:1.

72. A method as in claim 70, wherein the catalyst comprises a galloaluminosilicate Mordenite Framework Inverted zeolite.

73. A method for producing one or more fluid hydrocarbon products from a solid hydrocarbonaceous material comprising:
feeding a solid hydrocarbonaceous material to a fluidized bed reactor and contacting a catalyst with the solid hydrocarbonaceous material in the reactor, wherein the catalyst comprises porous particles and said particles have a pore size of less than about 100 Angstroms;
flowing a fluidization fluid into the reactor;
pyrolyzing within the reactor at least a portion of the solid hydrocarbonaceous material to produce one or more pyrolysis products;
reacting within the reactor in the presence of the catalyst at least a portion of the one or more pyrolysis products to produce the one or more fluid hydrocarbon products, wherein the one or more fluid hydrocarbon products comprise olefins and aromatics;
separating at least a portion of the olefins from the one or more fluid hydrocarbon products to produce a recycle stream comprising the separated olefins and a product stream comprising a remainder of the one or more fluid hydrocarbon products;
recovering said product stream; and
recycling at least a portion of the recycle stream to the reactor to increase the amount of aromatic compounds in the one or more fluid hydrocarbon products, wherein the aromatics in the one or more fluid hydrocarbon products comprise benzene, toluene, xylene, naphthalene or a mixture of two or more thereof, an amount of benzene, toluene, xylene, naphthalene or a mixture of two or more thereof in the one or more fluid hydrocarbon products is at least about 10% by weight based on the weight of the hydrocarbonaceous material used in forming the one or more pyrolysis products;
wherein a residence time of the fluidization fluid in the reactor is at least about 10 seconds, the residence time being calculated by dividing the volume of the reactor with the volumetric flow rate of the fluidization fluid.

\* \* \* \* \*